(12) United States Patent
Taatjes et al.

(10) Patent No.: US 6,677,309 B1
(45) Date of Patent: Jan. 13, 2004

(54) ANTI-CANCER DRUG ALDEHYDE CONJUGATE DRUGS WITH ENHANCED CYTOTOXICITY COMPOUNDS, COMPOSITIONS AND METHODS

(75) Inventors: Dylan J. Taatjes, Boulder, CO (US); David J. Fenick, Washington, DC (US); Tad H. Koch, Boulder, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/032,424

(22) Filed: Feb. 27, 1998

Related U.S. Application Data

(60) Provisional application No. 60/043,465, filed on Apr. 11, 1997.

(51) Int. Cl.$^7$ .................. A61K 31/70; C07H 15/24
(52) U.S. Cl. .................. 514/35; 514/25; 514/34; 536/6.4; 536/6.5
(58) Field of Search .................. 514/34, 25, 35; 536/6.4, 6.5

(56) References Cited

U.S. PATENT DOCUMENTS

| | | | |
|---|---|---|---|
| 4,948,880 A | 8/1990 | Hermentin et al. | 536/6.4 |
| 4,965,352 A | 10/1990 | Kolar et al. | 536/6.4 |
| 5,124,441 A | 6/1992 | Carlsson et al. | 536/6.1 |
| 5,196,522 A | 3/1993 | Farquhar et al. | 536/6.4 |
| 5,593,970 A | 1/1997 | Attardo et al. | 514/34 |

FOREIGN PATENT DOCUMENTS

| | | | |
|---|---|---|---|
| DE | 3913759 | 10/1990 | A61K/31/70 |
| JP | 60089466 A | 5/1985 | A61K/39/39 |

OTHER PUBLICATIONS

Fenick et al., J. Med. Chem., vol. 40, pp. 2452–2461, Aug. 1997.*
Abdella, B.R.J. and Fisher, J.A. (1985) "A chemical perspective on the anthracycline antitumor antibiotics" *Envir. Health Perspect.* 64:3–18.
Acton, E.M. (1980) "N–alkylation of anthracyclines", *Anthracyclines: Current Status and New Developments*, (Eds. Crooke, S.T. and Reich, S.D.), Academic Press, New York, Ch. 3, pp. 15–25.
Acton, E. and Tong, G. (1981) "Synthesis and preliminary antitumor evaluation of 5–Iminodoxorubicin" *J. Med. Chem.* 24(6):669–673.
Batist, G. et al. (1986) "Overexpression of a novel anionic glutathione transferase in multi–drug–resistant human breast cancer cells" *J. Biol. Chem.* 261(33):15544–15549.
Bird, D. et al. (1987) "A kinetic rationale for the inefficiency of 5–Iminodaunomycin as a redox catalyst" *J. Am. Chem. Soc.* 109(13):4046–4053.
Black, S.M. and Wolf, C.R. (1991) "The role of glutathione–dependent enzymes in drug resistance" *Pharmac. Ther.* 51:139–154.

Blair, S.L. (1997) "Glutathione metabolism in patients with non–small cell lung cancers" *Cancer Res.* 57:152–155.
Brown, J.R. (1978) "Adriamycin and related anthracycline antibiotics" *Prog. Med. Chem.* 15:125–164.
Brown, J.R. and Iman, S.H. (1984) "Recent studies on doxorubicin and its analogues" *Prog. Med. Chem.* 21:170–236.
Cantoni, O. et al. (1990) "*Comparative effects of doxorubicin and 4'–epi–doxorubicin on nucleic acid metabolism and cytotoxicity in a human tumor cell line*" *Cancer Chemother. Pharmacol.* 27:47–51.
Casazza, A.M. et al. (1980) "Effects of modifications in position 4 of the chromophore or in position 4' of the aminosugar, on the antitumor activity and toxicity of daunorubicin and doxorubicin", *Anthracyclines: Current Status and New Developments*, (Eds. Crooke, S.T. and Reich, S.D.), Academic Press, New York, Ch. 23, pp. 403–430.
Chaires, J.B. et al. (1996) "Parsing the free energy of anthracycline antibiotic binding to DNA" *Biochemistry* 35:2047–2053.
Coley, H.M. et al. (1993) "Examination by laser scanning confocal fluorescence imaging microscopy of the subcellular localisation of anthracyclines in parent and multidrug resistnt cell lines" *Br. J. Cancer* 67:1316–1323.
Cowan, K.H. et al. (1986) "Similar biochemical changes associated with multidrug resistance in human breast cancer cells and carcinogen–induced resistance to xenobiotics in rats" *Proc. Natl. Acad. Sci. USA* 83:9328–9332.
Cullinane, C.R. et al. (1994) "Formation of adriamycin–DNA adducts in vitro" *Nucl. Acids Res.* 22(12):2296–2303.
Cullinane, C.R. (1994) "Does adriamycin induce interstrand cross–links in DNA?" *Biochemistry* 33:4632–4638.
Cutts, S.M. and Phillips, D.R. (1995) "Use of oligonucleotides to define the site of interstrand cross–links induced by Adriamycin" *Nucl. Acids Res.* 23(13):2450–2456.
Cutts, S.M. (1996) "Adriamycin–induced DNA adducts inhibit the DNA interactions of transcription factors and RNA polymerase" *J. Biol. Chem.* 271(10):5422–5429.

(List continued on next page.)

Primary Examiner—Johann Richter
Assistant Examiner—Howard V. Owens, Jr.
(74) Attorney, Agent, or Firm—Greenlee, Winner & Sullivan, PC

(57) ABSTRACT

Monomeric and dimeric anti-cancer drug aldehyde conjugate compounds and pharmaceutically acceptable salts thereof. Specifically, monomeric and dimeric aldehyde conjugates of 1-2, dihetero-substituted anti-cancer drugs, including monomeric and dimeric aldehyde conjugates of anthracyclines, are provided. Also provided are pro-drugs which, after administration, release monomeric aldehyde conjugates. Further provided are pharmaceutical and therapeutic compositions containing anti-cancer drug aldehyde conjugates and methods of treating cancer using the aldehyde conjugates.

49 Claims, 3 Drawing Sheets

OTHER PUBLICATIONS

Davies, J. et al. (1983) "Mitochondrial NADH dehydrogenase–catalyzed oxygen radical production by adriamycin, and the relative inactivity of 5–iminodaunorubicin" 153(1):227–230.

d'Estaintot, B.L. et al. (1992) "The molecular structure of a 4'–epiadriamycin complex with d(TGATCA) at 1.7 Å resolution: comparasion with the structure of 4'–epiadriamycin d(TGTACA) and d(CGATCG) complexes" *Nucleic Acids Res.* 20(14):3561–3566.

Doroshow, J.H. (1983) "Anthracycline Antibiotic–stimulated superoxide, hydrogen peroxide, and hydroxyl radical production by NADH dehydrogenase" *Cancer Res.* 43:4543–4551.

Doyle, T.W. (1980) "Anthracycline Oligosaccharides", *Anthracyclines, Current Status and New Developments*, (Eds. Crooke, S.T. and Reich, S.D.), Academic Press, New York, Ch. 4, pp. 27–41.

Durand, R.E. and Olive, P.L. (1981) "Flow cytometry studies of intracellular adriamycin in single cells in vitro" *Cancer Res.* 41:3489–3494.

Egorin, M.J. et al. (1974) "Cytofluorescence localization of adriamycin and daunorubicin" *Cancer Res.* 34:2243–2245.

Fairchild, C.R. et al. (1987) "Isolation of amplified and overexpressed DNA sequences from adriamycin–resistant human breast cancer cells" *Cancer Res.* 47:5141–5148.

Fenick et al. (1997) "Doxoform and Daunoform: anthracycline–formaldehyde conjugate toxic to resistant tumor cells" *J. Med. Chem.* 40:2452–2461.

Frederick, C.A. et al. (1990) "Structural comparison of anticancer drug–DNA complexes: adriamycin and daunomycin" *Biochemistry* 29:2538–2549.

Gabizon, A. et al. (1994) "Prolonged circulation time and enhanced accumulation in malignant exudates of doxorubicin encapsulated in polyethylene–glycol coated liposomes" *Cancer Res.* 54:987–992.

Gaudiano, G. et al. (1994) "Reaction of anthracycline antitumor drugs with reduced glutathione. Formation of aglycon conjugates" *J. Am. Chem. Soc.* 116:6537–6544.

Gao, Y–G. et al. (1991) "Facile formation of a crosslinked adduct between DNA and the daunorubicin derivative MAR70 mediated by formaldehyde: Molecular structure of the MAR70–d(CGT ACG) covalent adduct" *Proc. Natl. Acad. Sci. USA* 88:4845–4849.

Giai, M. et al. (1991) "Chemoresistance in breast tumors" *Eur. J. Gynaecol. Oncol.* 12:359–73.

Gilles, R.J. et al. (1986) "Determination of cell number in monolayer cultures" *Anal. Biochem.* 159:109–113.

Guaglianone, P. et al. "Phase I and pharmacologic study of liposomal daunorubicin (DaunoXome)" *Investigational New Drugs* 12:103–110.

Gudas, J.M. et al. (1996) "Drug–resistant breast cancer cells frequently retain expression of a functional wild–type p53 protein" *Carcinogenesis* 17:1417–1427.

Hannun, Y.A. et al. (1985) "Activation of protein kinase C by triton X–100 mixed micelles containing diacylglycerol and phosphatidylserine" *J. Biol. Chem.* 260(18):10039–10043.

Hannun, Y.A. et al. (1989) "The adriamycin–iron (III) complex is a potent inhibitor of protein kinase C" *J. Biol. Chem.* 264(17):9960–9966.

Hartwell, L.H. and Kastan, M.B. (1994) "Cell cycle control and cancer" *Science* 266:1821–1828.

Inouye, S. (1968) "On the prediction of $pK_\alpha$ values of amino sugars" *Chem. Pharm. Bull.* 16:1134–1137.

Johnston, J. et al. (1983) "Overview of enzyme systems involved in bio–reduction of drugs and in redox cycling" *Biochem. Pharmac.* 32(14):2255–2258.

Kappus, H. (1986) "Comparison of DNA scission and cytotoxicity produced by adriamycin and 5–iminodaunorubicin in human colon carcinoma cells" *Biochem. Pharmacol.* 35:1–6.

Kleyer, D. and Koch, T.H. (1984) "Mechanistic investigation of reduction of daunomycin and 7–deoxydaunomycinone with Bi(3,5,5–trimethyl–2–oxomorpholin–3–yl)" *J. Am. Chem. Soc.* 106:2380–2387.

Lampidis, T.J. et al. (1997) "Circumvention of P–GP MDR as a function of anthracycline lipophilicity and charge" *Biochem.* 36:2679–2685.

Lasic, C.C. and Papahadjopoulos, D. (1995) "Liposomes revisited" *Science* 267:1275–1276.

Leng, F. et al. (1996) "Base specific and regioselective chemical cross–linking of daunorubicin to DNA" *J. Am. Chem. Soc.* 118(20):4731–4738.

Linn, S.C. et al. (1996) "p53 and P–glycoprotein are often co–expressed and are associated with poor prognosis in breast cancer" *Br.J. Cancer* 74:63–68.

Liu, L.F. (1989) "DNA topoisomerase poisons as antitumor drugs" *Annu Rev. Biochem.* 58:351–375.

Lown, W.J. et al. (1982) "Further studies on the generation of reactive oxygen species from activated anthracyclines and the relationship to cytotoxic action and cardiotoxic effects" *Biochem. Pharmacol.* 31:575–581.

Lown, W.J. et al. (1979) "Diminished superoxide anion generation by reduced 5–iminodaunorubicin relative to daunorubicin and the relationship to cardiotoxicity of the anthracycline antitumor agents" *Biochem. Pharmac*, 28:2563–2568.

Mahler, C. and Denis, L. (1992) "Management of relapsing disease in prostate cancer" *Cancer* 70:329–334.

Mimnaugh, E.G. et al. (1991) "Biochemical and pharmacologi8cal characterization of MCF–7 drug–sensitive and $Adr^R$ multidrug–resistant human breast tumor xenografts in athymic nude mice" *Biochem. Pharmacol.* 42:391–402.

Moore, H.W. and Czerniak, R. (1981) "Naturally occurring quinones as potential bioreductive alkylating agents" *Med. Res. Rev.* 1:249–280.

Myers, C.E. (1982) "Oxidative destruction of erythrocyte ghost membranes catalyzed by the Doxorubicin–iron complex" *Biochemistry* 21(8):1707–1712.

Pan, S. et al. (1981) "Comparative flavoprotein catalysis of anthracycline antibiotic" *Mol. Pharmacol.* 19:184–186.

Pollakis, G. et al. (1983) "Role of the quinone structure in the mitochondrial damage induced by antitumor anthracyclines" *FEBS Letters* 153(1):267–282.

Powis, G. (1987) "Metabolism and reactions of quinoid anticancer agents" *Pharmac. Ther.* 35:57–162.

Reile, H. et al. (1990) "Computerized determination of growth kinetic curves and doubling times from cells in microcultures" *Anal. Biochem.* 187:262–267.

Schreiber, J. et al. (1987) "One–electron reduction of daunomycin, daunomycinone, and 7–deoxydaunomycinone by the xanthine/xanthine oxidase system: Detection of semiquinone free radicals by electron spin resonance" *J. Am. Chem. Soc.* 109:348–351.

Schweitzer, B. and Koch, T. (1993) "Synthesis and redox chemistry of 5–deoxydaunomycin. A long–lived hydroquinone tautomer" *J. Am. Chem. Soc.* 115:5440–5446.

Serafino, A. et al. (1998) "Cytoplasmic localization of anthracycline antitumor drugs conjugated with reduced glutathione: a possible correlation with multidrug resistance mechanisms" *Anticancer Res.* 18:1159–1166.

Silverberg, E. et al. (1990) "Cancer Statistics, 1990" *Cancer J. Clin.* 40(1):9–26.

Sinha, B.K. (1989) "Free radicals in anticancer drug pharmacology" *Chem. Biol. Interact.* 69:293–317.

Sinha, B.K. and Mimnaugh, E.G. (1990) "Freeradicals and anticancer drug resistance: Oxygen free radicals in the mechanisms of drug cytotoxicity and resistance by certain tumors" *Free Radicals Biol. Med.* 8:567–581.

Skladanowski, A. and Konopa, J. (1994) "Interstrand DNA crosslinking induced by anthracyclines in tumour cells" *Biochem. Pharmacol.* 47(12):2269–2278.

Skladanowski, A. and Konopa, J. (1994) "Relevance of interstrand DNA crosslinking induced by anthracyclines for their biological activity" *Biochem. Pharmacol.* 47(12):2279–2287.

Skladanowski, A. and Kanopa, J. (1993) "Adriamycin and daunomycin induce programmed cell death (Apoptosis) in tumour cells" *Biochem. Pharmacol.* 46:375–382.

Slack, N.H. and Murphy, G.P. (1983) "A decade of experience with chemotherapy for prostate cancer" *Urology* 22:1–7.

Sweatman, T.W. and Israel, M. (1997) "Anthracyclines: Introduction to daunorubicin and doxorubicin, prototypical anthracyclines" *Cancer Therapeutics, Experimental and Clinical Agents*, (Ed., Teicher B.A.) Humana Press, Totowa, NJ, pp. 113–135.

Taatjes, D.J. et al. (1997) "Production of formaldehyde and DNA–adriamycin or DNA–daunomycin adducts, initiated through redox chemistry of dithiothreitol/iron, xanthine oxidase/NADH/iron, or glutathione/iron" *Chem. Res. Toxicol.* 10:953–961.

Taatjes, D.J. et al. (1996) "Alkylation of DNA by the anthracycline, antitumor drugs adriamycin and daunomycin" *J. Med. Chem.* 39:4135–4138.

Taatjes, D.J. et al. (1997) "Redox pahtway leading to the alkylation of DNA by the anthracycline, antitumor drugs adriamycin and daunomycin" *J. Med. Chem.* 40(8):1276–1286.

Theyer, G. et al. (1993) "Role of the MDR–1–encoded multiple drug resistance phenotype in prostate cancer cell lines" *J. Urology* 150:1544–1547.

Tritton, T.R. (1991) "Cell surface actions of adriamycin" *Pharmac. Ther.* 49:293–301.

van Rosmalen, A. (1995) "Stability of adriamycin–induced DNA adducts and interstrand crosslinks" *Nucl. Acids Res.* 23:42–50.

Volm, M. (1991) "Overexpression of P–glycoprotein and glutathione S–transferase–$\pi$ in resistant non–small cell lung carcinomas of smokers" *Br. J. Cancer* 64:700–704.

Wang, J.Y–T. et al. (1995) "Adducts of DNA and anthracycline antibiotics", *Anthracycline Antibiotics*, Ch. 11, pp. 164–182.

Wang, A.H–J. et al. (1991) "Formaldehyde cross–links daunorubicin and DNA efficiently: HPLC and X–ray diffraction studies" *Biochemistry* 30:3812–3815.

Weenen, H. et al. (1984) "Metabolism of 4'–modified analogs of doxorubicin. Unique glucuronidation pathway for 4'–epidoxorubicin" *Eur. J. Cancer Clin. Oncol.* 20:919–926.

Young, R.C., et al. (1981) "The anthracycline antineoplastic drugs" *New Engl. J. Med.* 305:139–153.

Zhang, H. et al. (1993) "Simultaneous incorporations of two anticancer drugs into DNA" *J. Biol. Chem.* 268(14):10095–10101.

\* cited by examiner

ANTI-CANCER DRUG ALDEHYDE CONJUGATE DRUGS WITH ENHANCED CYTOTOXICITY COMPOUNDS, COMPOSITIONS AND METHODS

CROSS-REFERENCE TO RELATED APPLICATIONS

This application claims priority under U.S.C. 119(e) to U.S. provisional application serial No. 60/043,465, filed under 35 U.S.C. 111(b) on Apr. 11, 1997, which is incorporated by reference in its entirety herein.

ACKNOWLEDGEMENT OF FEDERAL RESEARCH SUPPORT

The present invention was made, at least in part, with funding from the National Cancer Institute of the National Institutes of Health, grant number CA24665. Accordingly, the United States Government may have certain rights in this invention.

FIELD OF THE INVENTION

This invention relates to compounds useful in the treatment of cancer. Particularly, this invention relates to anti-cancer drugs comprising an amino alcohol functionality, e.g. anthracyclines. More particularly, this invention relates to anthracycline aldehyde conjugates formed by reaction of an anthracycline with an aldehyde, e.g. formaldehyde.

BACKGROUND OF THE INVENTION

Doxorubicin (adriamycin) continues to be one of the most important anti-cancer drugs available. It is a broad spectrum drug particularly useful in the treatment of Hodgkin's disease, non-Hodgkin lymphomas, acute leukemias, sarcomas, and solid tumors of the breast, lung, and ovary (young, R. C. et al. (1981) New Engl. J. Med. 305:139–153). The closely related drug daunorubicin (daunomycin) is used primarily for the treatment of acute leukemia. A major problem associated with doxorubicin and daunorubicin chemotherapy is multi-drug resistance. Multi-drug resistance is characterized by resistance to several drugs developed by tumor cells upon treatment with one drug. Mechanisms proposed for tumor cell multi-drug resistance include overexpression of cell membrane proteins which enhance efflux of the drug, and overexpression of glutathione transferase which transforms xenobiotics to glutathione conjugates for excretion (Volm, M. (1991) Br. J. Cancer 64:700–704; Giai, M. et al. (1991) Eur. J. Gynaecol. Oncol. 12:359–73; Black, S. M. and Wolf (1991) Pharmac. Ther. 51:139–154; Serafino, A. et al. (1998) Anticancer Res. in press). Glutathione itself is also thought to be involved in resistance in a variety of tumors (Blair, S. L. (1997) Cancer Res. 57:152–155). Resistance to anthracycline anti-cancer antibiotics has been shown to involve a lower concentration of drug-produced reactive oxygen species, presumably resulting from overexpression of enzymes which destroy superoxide and hydrogen peroxide (Sinha, B. K. and Mimnaugh, E. G. (1990) Free Radicals Biol. Med.8:567–581).

In spite of intensive investigation of the mode of action of doxorubicin and daunorubicin, the events leading to cell death and differential cytotoxicity are not totally understood. This has hindered the development of new analogs which are both more effective and which overcome multi-drug resistance. Both drugs are excellent DNA intercalators, and have been shown to concentrate in the cell nucleus (Chaires, J. B. et al. (1996) Biochemistry 35:2047–2053; Egorin, M. J. et al. (1974) Cancer Res. 34:2243–2245; Coley, H. M. et al. (1993) Br. J. Cancer 67:1316–1323). Crystallographic data have established specific sequences as the sites of drug intercalation (Wang, A. H.-J. et al. (1987) Biochemistry 26:1152–1163; Frederick, C. A. et al. (1990) Biochemistry 29:2538–2549). The drugs are redox active through the quinone functionality and are substrates for one-electron redox enzymes such as xanthine oxidase, cytochrome P450 reductase, and mitochondrial NADH dehydrogenase (Pan, S. et al. (1981) Mol. Pharmacol. 19:184–186; Schreiber, J. et al. (1987) J. Am. Chem. Soc. 109:348–351; Schreiber, J. et al. (1987) J. Am. Chem. Soc. 109:348–351; Kappus, H. (1986) Biochem. Pharmacol. 35:1–6). Furthermore, reduction in the presence of molecular oxygen results in catalytic production of superoxide and hydrogen peroxide (Lown, W. J. et al. (1982) Biochem. Pharmacol. 31:575–581; Doroshow, J. H. (1983) Cancer Res.43:4543–4551; Sinha, B. K. (1989) Chem. Biol. Interact. 69:293–317). In an anaerobic environment, reduction leads to glycosidic cleavage to produce a quinone methide transient, long thought to be an alkylating agent for DNA (Kleyer, D. and Koch, T. H. (1984) J. Am. Chem. Soc. 106:2380–2387; Abdella, B. R. J. and Fisher, J. A. (1985) Envir. Health Perspect. 64:3–18; Gaudiano, G. et al. (1994) J. Am. Chem. Soc. 116:6537–6544; Moore, H. W. and Czerniak, R. (1981), Med. Res. Rev. 1:249–280). Currently, the most popular explanation for cytotoxicity is induction of topoisomerase-mediated DNA strand breaks through intercalation, with modulation through a signaling cascade involving a cell membrane receptor for doxorubicin (Liu, L. F. (1989) 58:351–375; Tritton, T. R. (1991) Pharmac. Ther. 49:293–301).

Recent reports from several laboratories have rekindled interest in the concept of drug alkylation of DNA via a redox pathway as an important cytotoxic event. Phillips and co-workers reported in a series of papers that in vitro reductive activation of doxorubicin and daunorubicin in the presence of DNA led to transcription blockages (Cullinane, C. R. (1994) Biochemistry 33:4632–8; Cullinane, C. (1994) Nucl. Acids Res. 22:2296–2303; van Rosmalen, A. (1995) Nucl. Acids Res. 23:42–50; Cutts, S. M. and Phillips, D. R. (1995) Nucl. Acids Res. 23:2450–6; Cutts, S. M. (1996)3J. Biol. Chem. 271:5422–9). These transcription blockages were attributed to the alkylation and crosslinking of DNA by reductively activated drug, possibly involving a quinone methide transient. The site of alkylation and crosslinking was proposed to be the 2-amino substituents of 2'-deoxyguanosines at the location. 5'-GpC-3' in DNA. At about the same time, Skladanowski and Konopa established crosslinking of DNA by doxorubicin in HeLa S3 cells using a mild DNA denaturation-renaturation assay (Skladanowski, A. and Konopa, J. (1994) Biochem. Pharmacol. 47:2279–2287; Skladanowski, A. and Konopa, J. (1994) Biochem. Pharmacol. 47:2269–2278). They concluded that DNA crosslinks, although unstable to isolation, induced tumor cell apoptosis (Skladanowski, A. and Konopa, J. (1993) Biochem. Pharmacol. 46:375–382). We have recently demonstrated that the reported DNA alkylation and crosslinking does not involve the intermediacy of the quinone methide. The primary purpose of reductive activation of doxorubicin and daunorubicin is the production of superoxide and hydrogen peroxide (Taatjes, D. J. et al. (1996) J. Med. Chem. 39:4135–4138; Taatjes, D. J. et al. (1997) J. Med. Chem. 40, 1276–1286). These two reduced dioxygen species oxidize constituents in the medium to formaldehyde via Fenton chemistry (Taatjes, D. J. et al. (1997) Chem. Res. Toxicol. 10, 953–961). The resulting formaldehyde couples the 3'-amino group of intercalated doxorubicin or daunorubicin to the 2-amino group of deoxyguanosine via Schiff base chemistry. Thus, what Phillips and co-workers call a DNA "crosslink" by drug at 5'-GpC-3', we describe as a "virtual crosslink" involving one covalent bond from formaldehyde and one intercalative-hydrogen bonding interaction with the opposing strand (Cullinane, C. R. (1994) Biochemistry 33:4632–8). This virtual crosslink is shown in Formula I for the DNA sequence 5'-CpGpC-3' (Taatjes, D. J. et al. (1997) J. Med. Chem. 40, 1276–1286).

-continued

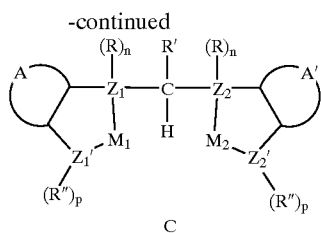

C

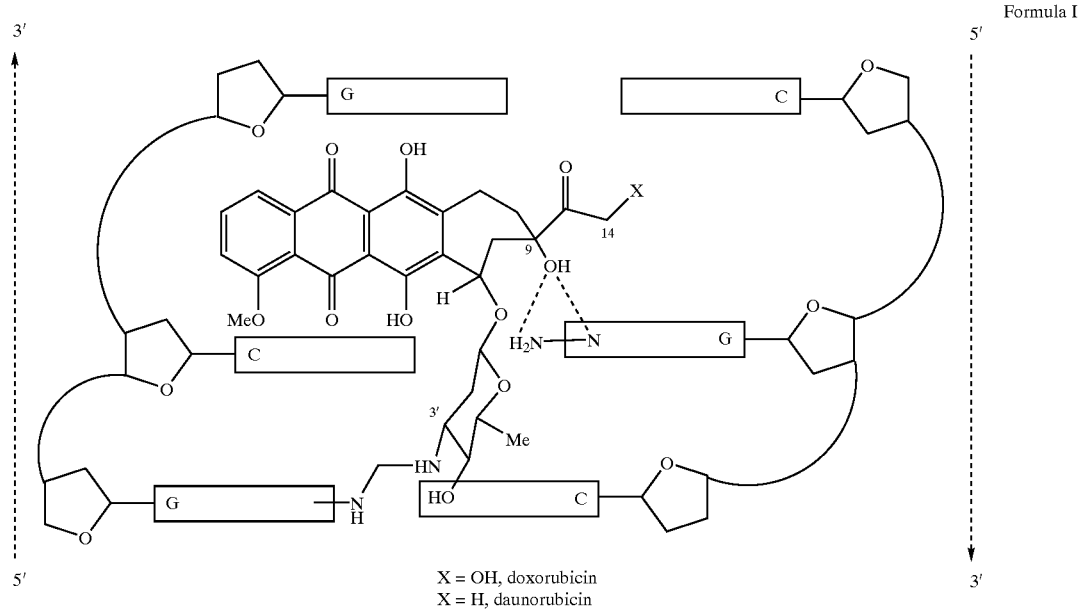

Formula I

X = OH, doxorubicin
X = H, daunorubicin

There is a long-felt need in the art for improved anti-cancer drugs, particularly those with greater efficacy against resistant cancers. This invention provides such drugs.

-continued

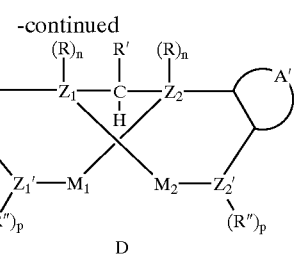

D

SUMMARY OF THE INVENTION

This invention provides dimeric drug aldehyde conjugate compounds which are anti-cancer drugs, and pharmaceutically acceptable salts thereof, of Formula II:

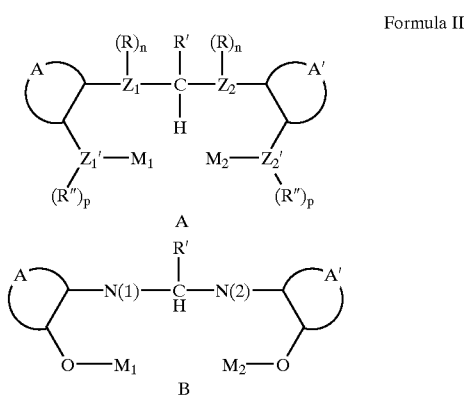

Formula II

Formula B illustrates Formula A when $Z_1$ is N(1) and $Z_2$ is N(2). (The use of the numerals 1 and 2 inside parentheses is to distinguish one nitrogen atom from the other.) $Z_1$, $Z_2$, are the same or different heteroatoms, selected from the group consisting of N, S, P, Si, Se, and Ge. More preferably, $Z_1$, $Z_2$, are the same or different heteroatoms selected from the group consisting of N or S. $Z_1'$ and $Z_2'$, are the same or different heteroatoms selected from the group consisting of N, O, S, P, Si, Se, and Ge. Preferably, $Z_1'$ and $Z_2'$ are the same or different heteroatoms selected from the group consisting of N, S and O. Most preferably $Z_1$ is N of an amino group and $Z_1'$ is an N of an amino group or O of an alcohol group, and $Z_2$ is N of an amino group and $Z_2'$ is an N of an amino group or O of an alcohol group. If $Z_1'$ is N, then preferably it is N of an amino group which is substituted with a non-hydrogen substituent, e.g., $C_{1-20}$ alkyl or $C_{1-20}$ acyl. If $Z_2'$ is N, then preferably it is N of an amino group which is substituted with a non-hydrogen substituent.

Only the 1,2-dihetero substituted portion of the anti-cancer drug is shown in Formula II; the remainder of the drug is represented with are lines connected to a letter A or A'. A and A' indicate that the remainder of the 1,2-dihetero-substituted portion of the anti-cancer drug may or may not be the same. In Formula II an example of A or A' is the 7-deoxyaglycon portion of an anthtacycline attached at its 7-position to the remainder of the sugar.

Each R and R" is, independent of each other R and R", selected from the group consisting of —H, —OH, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, or aminocarbonyl.

Each n is 0 or 1, depending on the identity of $Z_1$ and $Z_2'$. Each p is 0, 1 or 2 depending on the identity of $Z_1'$ and $Z_2'$. One of skill in the art will understand that n and p are determined in part by the valence state of the heteroatom to which the substitutent is bonded. The valence state of the heteroatom is satisfied depending on the value of n and/or p. For example, of $Z_1'$ is O (oxygen), then p is 0 (zero) as the valence state of oxygen calls for only two bonds to oxygen; hence, oxygen would not be substituted with an R".

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, or aminocarbonyl.

All R, R', and R" can be optionally substituted, e.g. with halogens, hydroxyl groups, amines, amino groups, etc.

For all the formulas herein wherein there is more than one R, each R is selected independently of each other R. The same is true for R' and for R".

Those of ordinary skill in the art recognize can choose without undue experimentation acceptable and preferred R, R' and R" based on fundamental rules of organic chemistry. For example, if $Z_1'$ is O (oxygen), then the R" bonded to $Z_1'$ is preferably not —OH because this substitution would change the oxidation state of $Z_1'$ and the resulting compound would be a hydroperoxide, which is unstable.

$M_1$ and $M_2$ are each a methylene, either or both of which can be substituted with —OH, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, or aminocarbonyl.

In Formula IIA, each of $M_1$ and $M_2$ is bonded to one of $Z_1$ or $Z_2$.

In Formula IIB each of $M_1$ and $M_2$ is bonded to one of N(1) or N(2).

Formula IIC illustrates that if $M_1$ is bonded to $Z_1$, then $M_2$ is bonded to $Z_2$. Formula IID illustrates that if $M_1$ is bonded to $Z_2$, then $M_2$ is bonded to $Z_1$.

More particularly, this invention provides dimeric drug aldehyde conjugates of the general structure shown in Formulas III A and B.

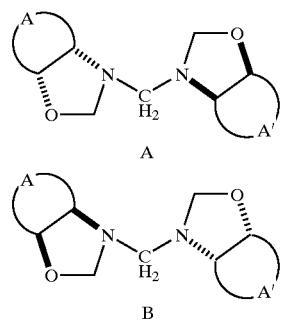

Formula III

The compounds of Formula III are preferably formed from drugs wherein the heteroatoms in the 1,2-Dihetero-substituted anti-cancer drug molecule are cis with respect to each other.

More particularly, this invention provides dimeric drug formaldehyde conjugates of the general structure shown in Formulas IV A and B.

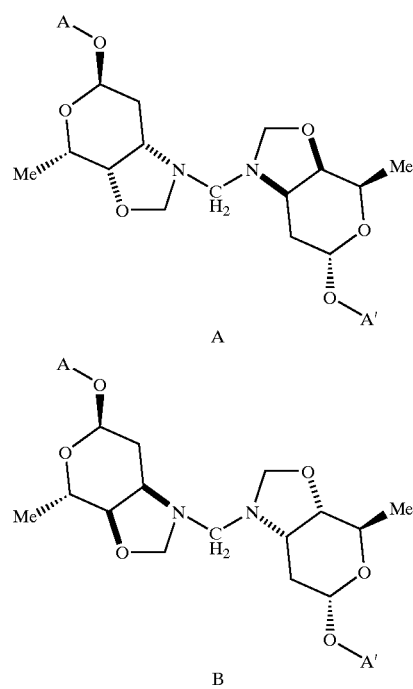

Formula IV

In Formula IV, A and A' are as defined above. Formula IVB differs from Formula IVA in the stereochemistry of the bonds connecting the oxazolidine rings to the 6-membered glycosidic ring. Formulas IVA and B illustrate the two oxazolidine rings bound to each other via a methylene.

Also particularly provided are dimeric formaldehyde conjugates of Formulae VA, B, and C, wherein two drug cores are bound to each other via a diazadioxabicyclic ring.

Formula V

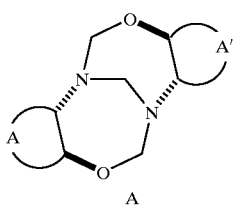
A

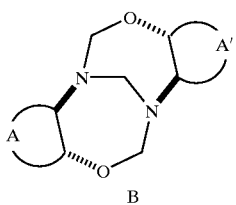
B

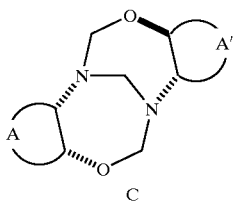
C

The compounds of Formula V are preferably formed from drugs wherein the heteroatoms in the 1,2-dihetero-substituted anti-cancer drug molecule are trans with respect to each other.

In Formula V, the regiochemistry of the heteroatoms can be changed, e.g., the O can be in the position of the N and vice versa. Furthermore, both heteroatoms can be N, such that each structure in Formula V would include 4 nitrogens. The difference between VA and VB is in the possible symmetry of the drug core of the 1,2-dihetero-substituted anti-cancer drug, represented by the A and A'.

Also particularly provided are formaldehyde conjugates of Formulas VIA, B, and C, wherein two drug cores are bound to each other via a diazadioxabicyclic ring. The letters A and A' are as defined above and can be the same or different drug cores. In Formula VI an example of A and A' is a 7-deoxyaglycon of an anthracycline attaced at its 7-position. Formulas VIA, B, and C differ among each other in the stereochemistry of the bonds attaching the diazadioxabicyclic ring to the 6-membered glycosidic rings.

Formula VI

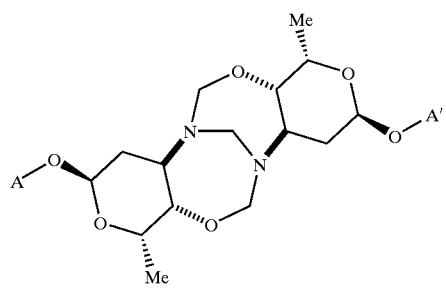
A

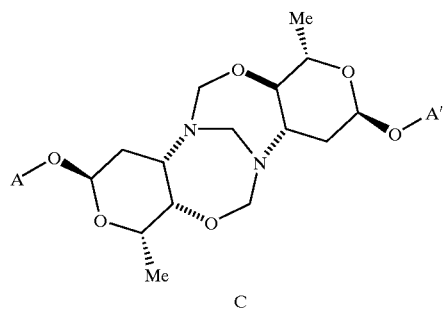
B

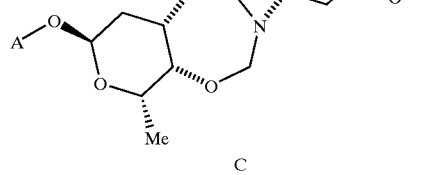
C

As in Formula V, the regiochemistry of the heteroatoms in Formula VI can be changed; e.g., the O can be in the position of the N and vice versa. Furthermore, three or all four heteroatoms can be N.

Formulas II through VI indicate that the dimeric drug aldehyde conjugates of this invention can comprise drug cores which are different from each other. For example, in Formula IV, A can be 7-deoxydaunorubicinon-7-yl and A' can be 7-deoxydoxorubicinon-7-yl or A can be 7-deoxydoxorubicinon-7-yl and A' can be 7-deoxydaunorubicinon-7-yl. Analogously, in Formula VI, A can be 7-deoxydaunorubicinon-7-yl and A' can be 7-deoxydoxorubicinon-7-yl.

More particularly, this invention provides the compounds bis(3'-N-(3'-N,4'-O-methylenedoxorubicinyl))methane (the dimeric formaldehyde conjugate of doxorubicin) and bis(3'-N-(3'-N,4'-O-methylenedaunorubicinyl))methane (the dimeric formaldehyde conjugate of daunorubicin) which are dimeric oxazolidines, formaldehyde conjugates of the parent drugs, formed by reaction of formaldehyde with doxorubicin and daunorubicin, respectively. See Formula VII A and B, respectively. The dimeric formaldehyde conjugate of doxorubicin is much more cytotoxic to sensitive and resistant tumor cells than is the parent drug doxorubicin, and the dimeric formaldehyde conjugate of daunorubicin is much more cytotoxic to resistant tumor cells than is the parent drug daunorubicin. Also provided is the dimeric formaldehyde conjugate of epidoxorubicin, which consists of two molecules of epidoxorubicin bonded together with three methylene groups at the amino sugar in a 1,6-diaza-4,9-dioxabicyclo[4.4.]undecane ring system. See Formula VII C.

Formula VII A, B, and C
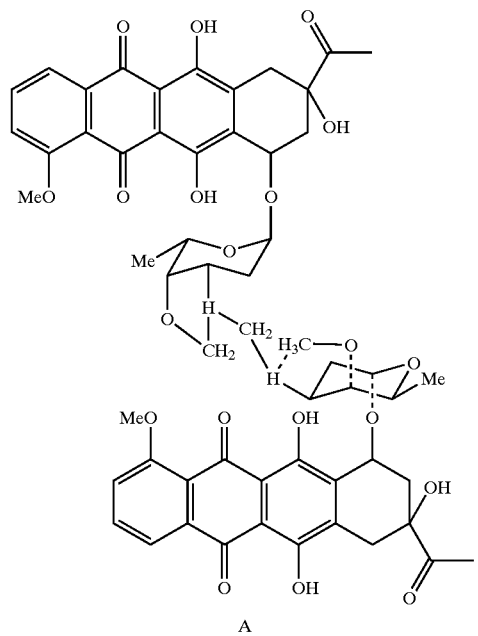
A
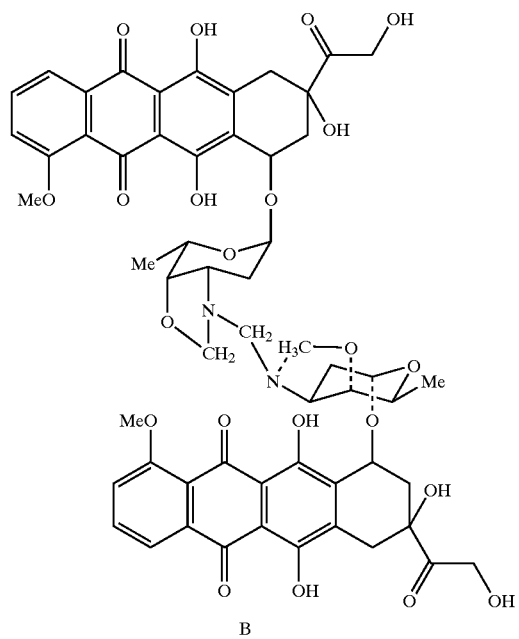
B
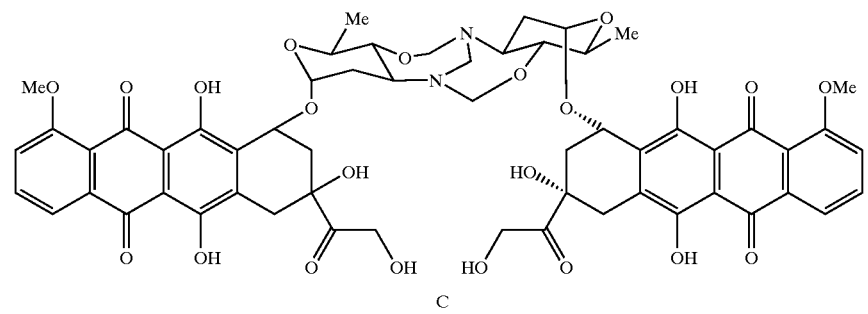
C

Drug aldehyde conjugates and particularly drug formaldehyde conjugates of anthracyclines besides doxorubicin, daunorubicin and epidoxorubicin are also disclosed. Methods for making drug aldehyde conjugates and drug formaldehyde conjugates are disclosed.

The aldehyde conjugates as described in Formulas II–VII show dimeric aldehyde conjugates, i.e., two 1,2-diheterosubstituted anti-cancer drug molecules are bonded by carbons derived from aldehydes. This invention also provides monomeric aldehyde conjugates, i.e., one 1,2-diheterosubstitued anti-cancer drug molecule is bonded by carbon derived from an aldehyde.

Monomeric drug aldehyde conjugates of 1,2-diheterosubstitued anti-cancer drugs of Formula VIII are provided:

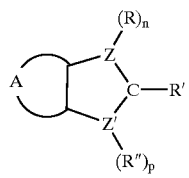

Formula VIII

In Formula VIII R, R" and R' are as defined in Formula II. Each n is 0, 1 or 2. Each p is 0, 1 or 2. Z and Z' are the same or different heteroatoms of an anti-cancer drug and are selected from the group consisting of N, S, O, P, Si, Se, and Ge. More preferably, Z and Z' are, independently of each other, selected from the group consisting of N, S and O. Most preferably, one of Z and Z' is N of an amino group and one of Z and Z' is an O of an alcohol group. If both Z and Z' are N, then preferably at least one of Z and Z' is N of an amino group which is substituted with a non-hydrogen substituent, e.g., $C_{1-20}$ alkyl or $C_{1-20}$ acyl.

Monomeric drug aldehyde conjugates of Formula VIII are preferably formed by reaction of an aldehyde with a 1,2-dihetero substituted anti-cancer drug in which the 1,2-diheteroatoms are cis to each other.

1,2-dihetero substituted anti-cancer drugs in which the heteroatoms are trans to each other preferably undergo reaction to form a monomeric drug aldehyde conjugate of Formula IX.

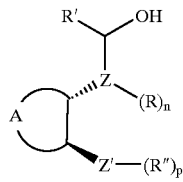

Formula IX

In Formula IX, R, R', R" are as defined above in Formula II. Z and Z' are as defined above in Formula VIII. Each n is 0, 1 or 2. Each p is 0, 1, 2 or 3.

If the 1,2-dihetero substituted anti-cancer drug is an amino alcohol containing anti-cancer drug, and the heteroatoms are trans with respect to each other, then a monomeric drug aldehyde conjugate of Formula X is preferably formed.

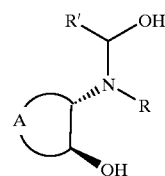

Formula X

R and R' are as defined above.

This invention further provides pro-drugs which, after administration, release the monomeric aldehyde conjugates, e.g. the mono-oxazolidine or hydroxylmethylene compounds of this invention. The pro-drugs of 3'-N,4'-O-methylenedoxorubicin and 3'-N,4'-O-methylenedaunorubicin are more hydrolytically stable than the unfunctionalized/unprotected respective mono-oxazolidines as well as the dimeric formaldehyde conjugate of doxorubicin and the dimeric formaldehyde conjugate of daunorubicin, respectively. The pro-drugs of this invention include the mono-okazolidine compounds which have had functional groups added to them. These pro-drugs include but are not limited to compounds wherein the 3'-amino group of the mono-oxazolidine is functionalized/protected. This is accomplished, for example, by acylation or ethoxyformylation of the 3'-amino group. The resulting functional groups, e.g., amide and carbamate groups, are susceptible to hyrolysis in vivo, thereby releasing the mono-oxazolidine. Further, the functional groups can contain substituents which provide the compounds with desirable properties. For example, a carbamate functional group containing a t-butyl group or a hydrocarbon chain can be added to the drug to increase its lipophilicity, thereby facilitating incorporation of the drugs into a liposomal delivery system. Similarly, the hydroxylmethylene compounds (monomeric drug formaldehyde conjugates) of this invention, such as those formed by hydrolysis of the dimeric formaldehyde conjugate of epidoxorubicin, can be functionalized to form pro-drugs.

The compounds of this invention are useful in treating cancer. They are effective in inhibiting survival and/or growth of cancer cells and/or for inhibiting undesirable cell growth in general.

This invention further provides compositions and methods for clinical administration of aldehyde conjugates of this invention. In particular, compositions and methods of administering the dimeric formaldehyde conjugate of daunorubicin and the dimeric formaldehyde conjugate of doxorubicin in a liposomal delivery system are disclosed. A liposomal delivery system can be used to stabilize the formaldehyde conjugates of this invention, particularly the dimeric formaldehyde conjugate of doxorubicin, the dimeric formaldehyde conjugate of daunorubicin, and the respective mono-oxazolidines. Liposomes protect the drugs from undesirably premature hydrolysis of the formaldehyde derived conjugates and oxazolidine rings. Protection against premature hydrolysis is less of a concern with more hydrolytically stable conjugates, e.g. the dimeric formaldehyde conjugate of epidoxorubicin.

This invention further provides pharmaceutical and therapeutic compositions which contain a pharmaceutically or therapeutically effective amount of these conjugates and therapeutic methods and methods of treatment employing such methods. In particular, this invention relates to methods of treating cancer by administration of the anthracycline formaldehyde conjugates disclosed herein. A method of treatment of cancer when multidrug resistance has occurred by administration of the conjugates and compositions containing such conjugates is also provided.

This invention further provides for methods of treating cancer employing the compounds of this invention and pharmaceutical and therapeutic compositions and liposomal delivery systems.

DETAILED DESCRIPTION OF THE INVENTION

Figure 1:
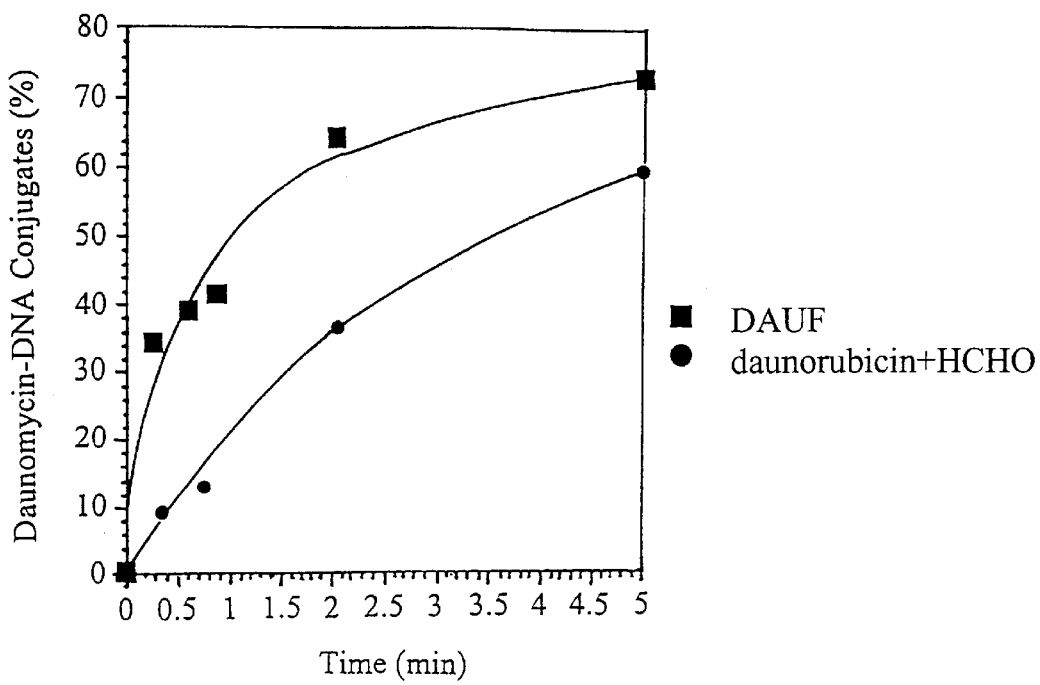
FIG. 1 is a graph showing formation of drug-DNA conjugates (containing virtual cross-links) from reaction of 33 $\mu$M $(GC)_4$ with either 55 $\mu$M of the dimeric formaldehyde conjugate of daunorubicin or 110 $\mu$M daunorubicin plus 165 $\mu$M formaldehyde in pH 7.4 phosphate buffer at 25° C. as a function of time. Drug-DNA conjugate formation represents the sum of the individual drug-DNA conjugates A–D and is shown as a percent of the initial $(GC)_4$ concentration.

The term "1,2-dihetero-substituted anti-cancer drug" refers to an anti-cancer drug with two heteroatoris on adjacent carbons. The term "amino alcohol containing anti-cancer drug" refers to an anti-cancer drug which contains a 1,2-amino alcohol functionality, i.e. contains an amino moiety and an alcohol moiety on adjacent carbons of a 1,2-dihetero-substituted anti-cancer drug. The term "amino alcohol containing anti-cancer aldehyde conjugate" as used herein refers to a compound formed by reaction of an aldehyde with an amino alcohol containing anti-cancer drug. The term "drug aldehyde. conjugate" as used herein refers to a compound formed by reaction of an aldehyde with a 1,2-dihetero-substituted anti-cancer drug and specifically includes dimeric drug aldehyde conjugates as well as monomeric drug aldehyde conjugates. The term "anthracycline aldehyde conjugate" as used herein refers to a compound formed by reaction of an aldehyde with an anthracycline and specifically includes dimeric drug aldehyde conjugates as well as monomeric drug aldehyde conjugates. The term "drug formaldehyde conjugate" as used herein refers to a compound formed by reaction of formaldehyde with a 1,2-dihetero-substituted anti-cancer drug and specifically includes dimeric drug formaldehyde conjugates as well as monomeric drug formaldehyde conjugates. The term "anthracycline formaldehyde conjugate" as used herein refers to a compound formed by reaction of formaldehyde with an anthracycline, and specifically includes dimeric drug formaldehyde conjugates as well as monomeric drug formaldehyde conjugates.

The "formaldehyde adduct derivatives" described in U.S. provisional application serial No. 60/043,465, filed Apr. 11, 1997 are termed "drug aldehyde conjugate" or "aldehyde conjugates" or more specifically, "drug formaldehyde conjugates" or "formaldehyde conjugates" in the present application.

The term "anti-cancer drug" refers to a compound effective in the treatment of cancer. Preferably, the anti-cancer drugs of this invention are those which affect cancer cells and/or are effective in treating cancer by reacting with an aldehyde to form a drug aldehyde conjugate. Preferred anti-cancer drugs are those which, in addition to the 1,2-diheteroatom-substitution, have the following general structural components: (1) a nucleic acid intercalating region and (2) a nucleic acid binding region, e.g. a "ring" or "arm", which is free to rotate out of the plane of the intercalating region. For example, the linear four-ring (3 of which are aromatic rings)portion (the aglycon portion) of an anthracycline is (1) a nucleic acid intercalating region, and the sugar of an anthracycline is a (2) nucleic acid binding region. Other linear, especially tetracyclic, ring systems with some, especially three, aromatic rings and a non-aromatic ring at the end, anti-cancer drugs are preferred. Anti-cancer drugs containing anthracene structures as the nucleic acid intercalating region are also preferred.

In general, this invention particularly includes A and A' having the structure of naturally derived, semi-synthetic, or synthetic anthracycline aglycons plus that portion of the sugar which may not be shown in the formula.

More preferred anti-cancer drugs of this invention are anthracyclines. Anthracyclines include naturally occurring, semi-synthetic, and synthetic anthracyclines.

The term "core structure" is that portion of a 1,2-dihetero-substituted anti-cancer drug to which are bonded the adjacent carbons bearing the 1,2-diheteroatom substituents.

Dimeric drug aldehyde conjugates are compounds wherein two 1,2-diheter-substituted anti-cancer drug, e.g. anthracycline, molecules are covalently bound to a carbon derived from an aldehyde. If the aldehyde is formaldehyde, then the conjugate is a dimeric drug formaldehyde conjugate. Dimeric drug formaldehyde conjugates include but are not limited to dimeric oxazolidines (bis-oxazolidinylmethanes, which contain two oxazolidine-drug units covalently bound by a methylene) and dimeric diaza-dioxabicyclic conjugates.

Monomeric drug aldehyde conjugates are compounds wherein one 1,2-dihetero-substituted anti-cancer drug, e.g. anthracycline, molecule is covalently bound to a carbon derived from an aldehyde. If the aldehyde is formaldehyde, then the conjugate is a monomeric drug formaldehyde conjugate. Monomeric drug formaldehyde conjugates include but are not limited to mono-oxazolidines and mono- and bis-hydroxylmethylene conjugates.

In this application we disclose the synthesis, characterization, and cytotoxicity of novel compounds which are drug aldehyde conjugates which result from reaction of an aldehyde with a 1,2-dihetero-substituted anti-cancer drug.

Scheme I

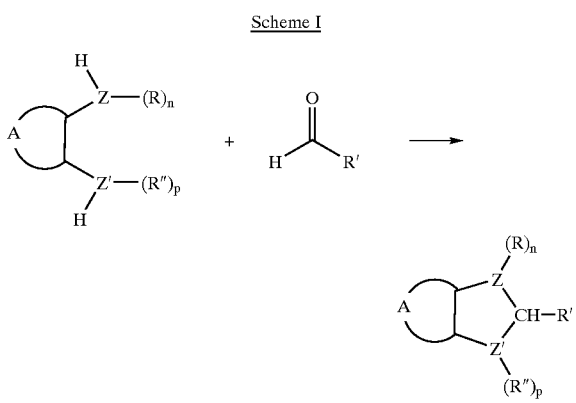

In Scheme I, Z and Z' are the same or different heteroatoms, selected from the group consisting of N, S, O, P, Si, Se, and Ge. More preferably, Z and Z' are, independently of each other, selected from the group consisting of N, S, and O. Most preferably, one of Z and Z' is N of an amino group and one of Z and Z' is O of an alcohol group. If both Z and Z' are N, then preferably at least one of Z and Z' is N of an amino group which is substituted with a non-hydrogen substituent, e.g., $C_{1-20}$ alkyl or $C_{1-20}$ acyl.

As discussed above, n and p are chosen to satisfy the valence of the heteroatom to which the substituent R or R" is bonded. Each n is 0, 1 or 2, depending on the identity of $Z_1$ Each p is 0, 1 or 2, depending on the identity of Z'. An example of how the valence state affects selection of and number of R, R' and R" is the following. If Z is O, then R is not present, because O bonds to only two atoms in general. Likewise, if Z' is then R" is not present. If Z is Si, n can be 2 because Si takes 4 bonds.

Only the 1,2-dihetero-substituted portion of the anti-cancer drug is shown in Scheme I. The remainder of the drug, the drug core, is represented with arc lines connected to a large letter A. For example, in this case, A can be the 7-deoxyaglycon portion of an anthracycline attached at its 7-position to the remainder of the sugar (the remainder of the sugar being that portion not specifically shown, i.e. the portion besides the 1,2-diheteroatoms and the carbons to which they are bound).

Each R and R" is, independent of each other R and R", selected from the group consisting of —H, —OH, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, or aminocarbonyl.

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, or aminocarbonyl.

Scheme I shows the preferred reaction of 1,2-dihetero-substituted anti-cancer drugs in which the heteroatoms are cis with respect to each other.

Non-limiting examples of R, R" and R' are as follows. Non-limiting examples of $C_{1-6}$ alkyl include methyl, ethyl, isopropyl, and the like. Non-limiting examples of $C_{1-6}$ alkenyl include ethenyl, isopropenyl, butenyl and the like. Non-limiting examples of $C_{1-20}$ alkyl include butyl, pentyl, hexyl, methyihexyl, octyl, dodecyl, halogenated methyl, halogenated isopropyl, and the like. Non-limiting examples of $C_{1-20}$ alkenyl include pentenyl, hexenyl, methylhexenyl, octenyl, dodecenyl, halogenated methyl, halogenated isopropyl, and the like. Non-limiting examples of $C_{1-20}$ acyl include formyl, acetyl, benzoyl, proprionyl, trifluoroacetyl and the like. Non-limiting examples of hydroxylated alkyl include hydroxymethyl, hydroxyethyl, hydroxyisopropyl, hydroxybutyl, and the like. Non-limiting examples of hydroxylated alkenyl include hydroxyisopropenyl, hydroxybutenyl, and the like. Non-limiting examples of halogenated alkyl include chloromethyl, 2-fluoroethyl, 2,2-difluoroisopropyl, 4-iodobutyl, 3-chloropentyl, and the like. Non-limiting examples of silyl include trimethylsilyl, dimethyl-t-butylsilyl and the like. Non-limiting examples of sulfonyl include mthylsulfonyl, phenylsulfonyl, p-toluenesulfonyl and the like. Non-limiting examples of sulfonatoalkyl include sulfonatomethyl, sulfonatoisopropyl, sulfonatophenyl and the like. Non-limiting examples of alkylaryl include toluyl, p-butylphenyl and the like. Non-limiting examples of aralkyl include benzyl, 2-phenylpropyl and the like. Non-limiting examples of alkoxyalkyl include 2-methoxyethyl, 2-ethoxypropyl and the like. Non-limiting examples of polyalkoxyalkyl include polyethylene glycol, polypropylene glycol and the like. Non-limiting examples of alkoxycarbonyl include methoxycarbonyl, phenoxycarbonyl and the like. Non-limiting examples of carboxyalkyl include carboxymethyl, carboxydodecyl, and the like, and particularly the salts thereof. Non-limiting examples of aminocarbonyl include methylaminocarbonyl, phenylamincarbonyl and the like.

Particularly disclosed are drug aldehyde conjugates which result from reaction of an aldehyde at the 1,2-amino alcohol functionality of anti-cancer drugs, e.g. the amino sugar groups of anthracyclines. See Scheme II.

Scheme II

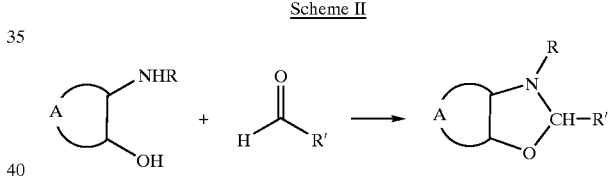

In Scheme II, R and R' are defined as above in Scheme I. Again, only the 1,2-dihetero substituted portion of the anti-cancer drug is shown in Scheme II. The remainder of the drug is represented with arc lines connected to a large letter A (drug core).

This invention further provides the monomeric drug aldehyde conjugates of anti-cancer drugs formed by reaction of anti-cancer drugs containing an amino alcohol functionality with an aldehyde, as shown in Scheme II.

Of particular importance are the monomeric formaldehyde conjugates of anthracyclines, which are mono-oxazolidine conjugates of anthracyclines. Particularly, this invention provides the mono-oxazolidines 3'-N,4'-O-methylenedoxorubicin and 3'-N,4'-O-methylenedaunorubicin (shown in Scheme III). The dimeric formaldehyde conjugate of doxorubicin and the dimeric formaldehyde conjugate of daunorubicin hydrolyze in aqueous medium back to the parent drugs (doxorubicin and daunorubicin, respectively) and formaldehyde. The mono-oxazolidines 3'-N,4'-O-methylenedoxorubicin and 3'-N,4'-O-methylenedaunorubicin are intermediates in the hydrolysis. These mono-oxazolidines are an important form of the drug useful in treating cancer. The mono-oxazolidines are believed to be the species which alkylate DNA, and other cellular structures such as proteins and lipids, leading to cell death.

Scheme III

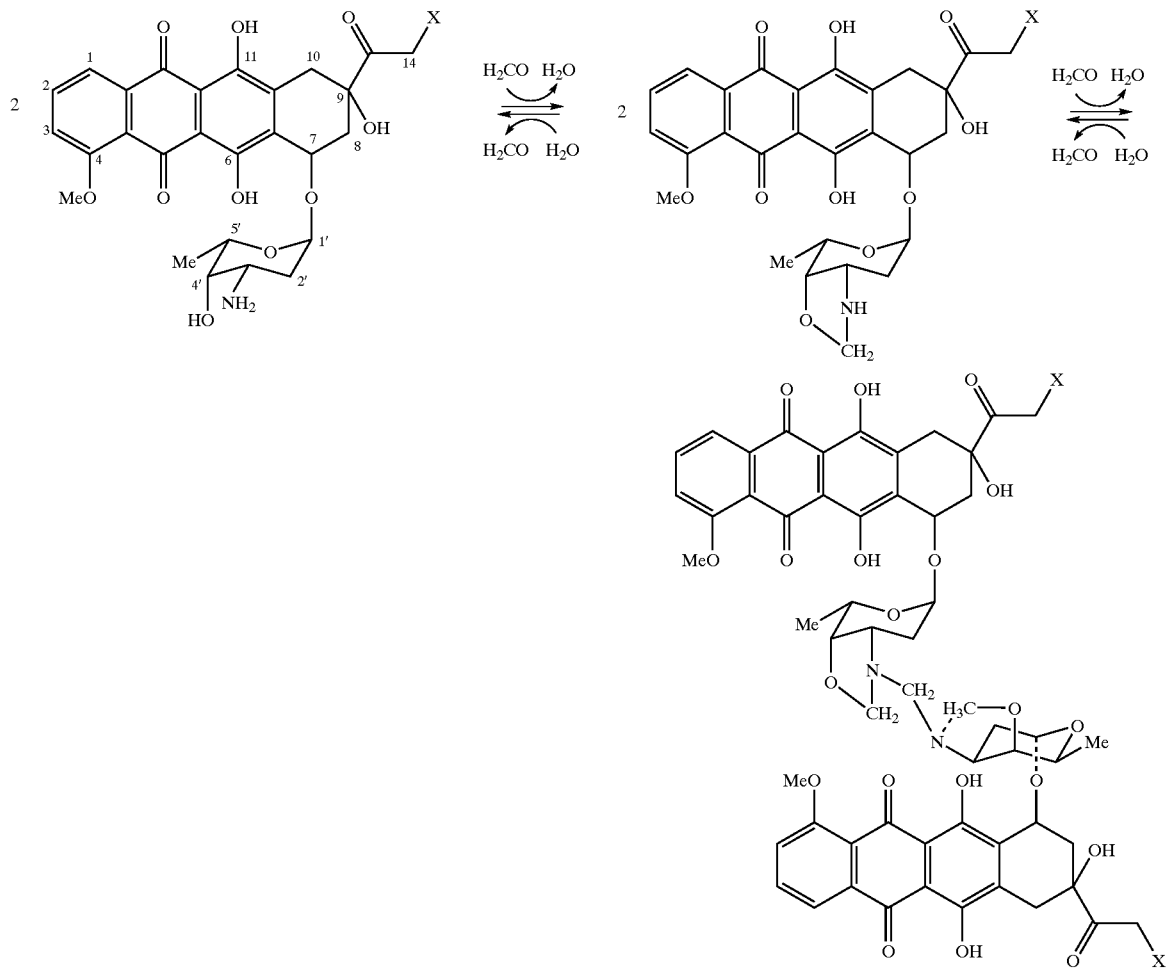

X = OH, doxorubicin
X = H, daunorubicin
X = H, daunorubicin mono-oxazolidine
X = OH, doxorubicin mono-oxazolidine This invention further provides the monomeric formaldehyde conjugates of 1,2-dihetero-substituted anti-cancer drugs, as taught in Scheme IV. 1,2-dihetero-substituted anti-cancer drugs in which the heteroatoms are trans to each other more preferably undergo reaction to form an aldehyde conjugate according to Scheme IV, as opposed to Scheme I, because of the greater distances between heteroatoms in trans 4, 5 or 6 membered ring compounds.

Scheme IV

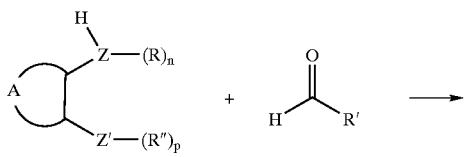

-continued

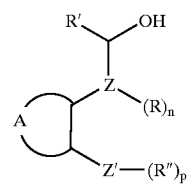

In Scheme IV, R, R', R", n, Z and Z' are as defined for Scheme I. However, p can be 0, 1, 2 or 3.

Scheme V shows reaction of a 1,2-dihetero substituted anti-cancer drug in which Z is an N of an amino group and Z' is an O of an alcohol group.

Scheme V

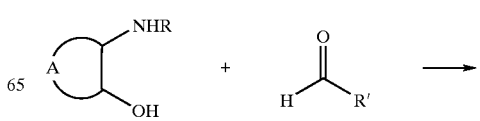

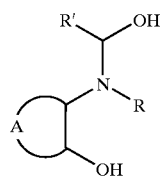

In Scheme V, R and R' are as defined in Scheme I.

For example, the dimeric formaldehyde conjugate of epidoxorubicin, which has a bridged bicyclic structure (Scheme VI, structure A), hydrolyzes in aqueous medium to an intermediate with a structure bearing a 10-membered ring (Scheme VI, Intermediate B). This fused intermediate then slowly hydrolyzes to two monomeric formaldehyde conjugates, a bishydroxylmethylene conjugate (Intermediate C) and a monohydroxylmethylene conjugate (Intermediate D).

SCHEME VI

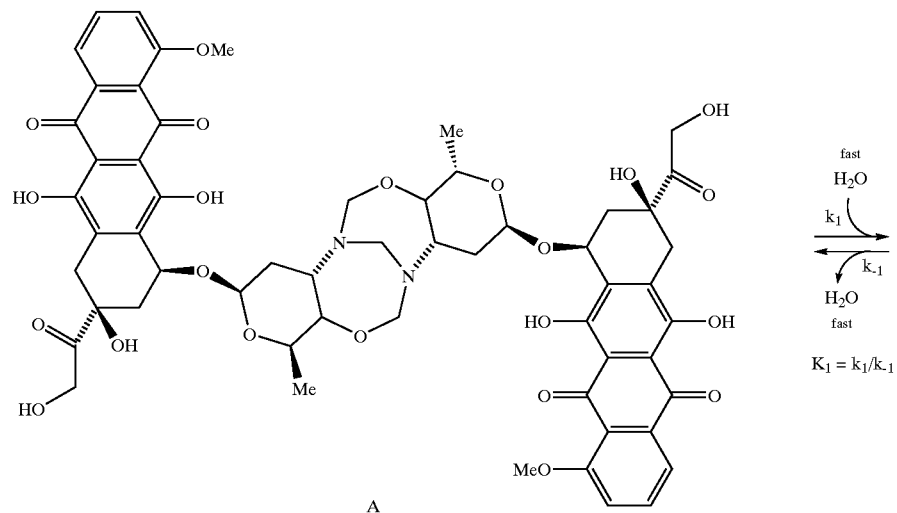

A

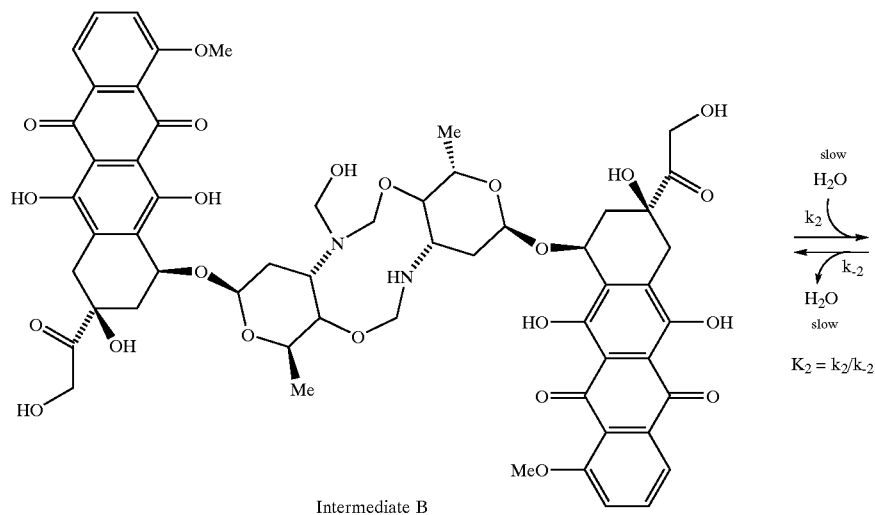

Intermediate B

-continued

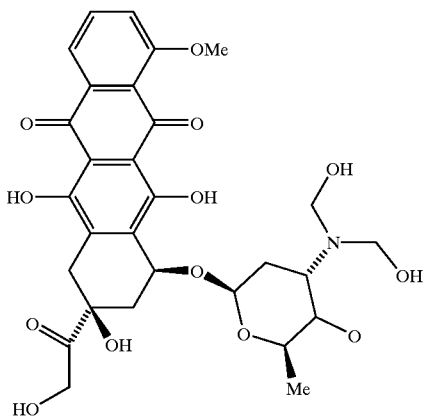

Intermediate C

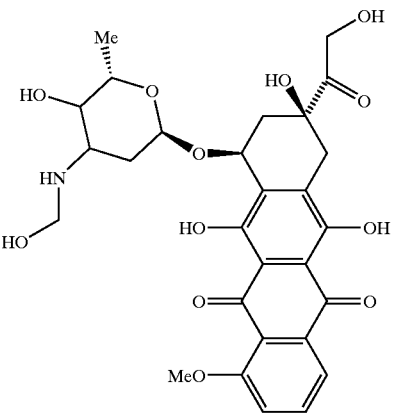

Intermediate D

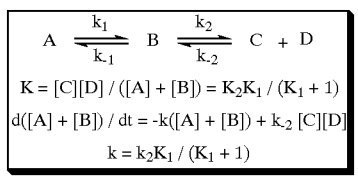

Of particular importance are the formaldehyde conjugates of anthracyclines, especially epidoxorubicin, doxorubicin and daunorubicin. The dimeric formaldehyde conjugate of doxorubicin and the dimeric formaldehyde conjugate of daunorubicin include dimeric oxazolidines which rapidly hydrolyze back to the parent drugs and formaldehyde in aqueous medium. Parent drugs are anti-cancer drugs before reaction with an aldehyde, e.g. doxorubicin and duanorubicin, respectively, in this case. In spite of this lability, the dimeric formaldehyde conjugate of doxorubicin and the dimeric formaldehyde conjugate of daunorubicin show enhanced cytotoxicity toward tumor cells, especially resistant tumor cells, over their respective parent drugs. The dimeric formaldehyde conjugate of epidoxorubicin, which has a dimeric diazadioxabicyclic structure, hydrolyzes more slowly to release formaldehyde than do the dimeric formaldehyde conjugate of doxorubicin and the dimeric formaldehyde conjugate of daunorubicin and its hydrolysis does not proceed to completion, but comes to an equilibrium of intermediates. The dimeric formaldehyde conjugate of epidoxorubicin is more toxic to tumor cells, especially resistant tumor cells, than its parent drug. It is believed that these conjugates exhibit enhanced cytotoxicity because they do not require drug-induced intracellular production of formaldehyde. Without wishing to be bound to any particular theory, the results of our work and that of others point to the following sequence of events for the cytotoxicity of doxorubicin (Taatjes, D. J. et al. (1996) J. Med. Chem. 39:4135–4.138; Taatjes, D. J. et al. (1997) J. Med. Chem. 40, 1276–1286; Cullinane, C. R. (1994) Biochemistry 33:4632–8; Skladanowski, A. and Konopa, J. (1994) Biochem. Pharmacol. 47:2279–2287). The drug catalyzes the production of superoxide and hydrogen peroxide through the redox machinery of the quinone functionality. These reactive oxygen species, through an iron catalyzed Fenton reaction, oxidize cellular constituents to produce aldehydes, e.g. acetaldehyde, malondialdehyde, and formaldehyde. Iron is available because of its strong association with the drug (Myers, C. E. (1982) Biochemistry 21:1707–12). The resulting aldehyde reacts with the drug to produce the dimeric formaldehyde conjugate of doxorubicin and/or the respective mono-oxazolidine, 3'-N,4'-O-methylenedoxorubicin. The dimeric formaldehyde conjugate of doxorubicin and/or the respective mono-oxazolidine reacts to form virtual cross-links at sites in DNA, which trigger apoptosis (Skladanowski, A. and Konopa, J. (1993) Biochem. Pharmacol. 46:375–382). A similar sequence of events is believed to result in the cytotoxicity of other anti-cancer drugs with 1,2-diheteroatom functionalities, e.g., 1,2-amino alcohol functionalities. Anti-cancer drug. aldehyde conjugates are believed to exert anti-cancer effect via a similar sequence of events, except that such conjugates do not need to catalyze superoxide and hydrogen peroxide production for the ultimate production of aldehydes, because they carry their own aldehyde equivalents in the conjugate molecule.

As discussed above, we believe that not only do anthracyclines, but also all other 1,2-dihetero-substituted anti-cancer drugs, exert their therapeutic effect via this mechanism.

The present invention provides novel compounds useful in' the treatment of cancer, methods for synthesizing such compounds, and methods of treating cancers, particularly resistant cancers, employing such compounds.

The present invention provides compounds formed by reaction of anti-cancer drugs with aldehydes, e.g. formaldehyde. Quinoid anti-cancer drugs, including many anthracycline derivatives as well as non-anthracycline drugs such as Mitomycin C, are well-known in the art (Powis, G. (1987) Pharmac. Ther. 35:57–162; Arcamone, F. (1981) in Medicinal Chemistry: A Series of Monographs, Vol. 17 Doxorubicin: Anticancer Antibiotics, Academic Press, NY; Lown, J. (1988), Anthracycline and Anthracenedione-based Anticancer Agents, Elsevier Science Publishing Co., Inc.)

Several thousands of anthracycline derivatives are known. They have been obtained from streptomyces biosynthesis or from semisynthetic modification of existing anthracyclines (Arcamone, F. (1980) Doxrubicin, Academic Press, New York; Thomson, R. H. (1987) Naturally Occurring Quinones III: Recent Advances, Chapman and Hall, New York; Anthracyclines: Current Status and New Developments, Academic Press, New York (1980); Brown, J. R. and Iman, S. H. (1984) Prog. Med. Chem. 21: 170–236; Brown, J. R. (1978) Prog. Med. Chem. 15: 125–164; U.S. Pat. No. 5,593,970 to Attardo et al.; U.S. Pat. No. 4,948,880 to Hermentin et al.; U.S. Pat. No. 4,965,352 to Kolar et al.; U.S. Pat. No. 5,124,441 to Carlsson et al.; PCT Publication WO 85/05030; and European. Patent Appl. No. EP 0457215A 1, inventor Animate et al.)

In general, anthracyclines include compounds of Formula XI.

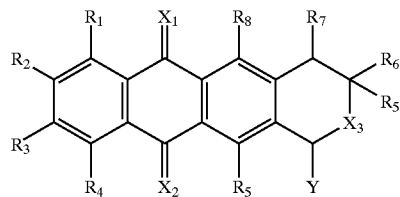

Formula XI

In general, the substitutents can be chosen as follows. $X_1$ and $X_2$, independent of one another, are O; S; or substituted or unsubstituted amino. $X_3$ is C (substituted or unsubstituted); O; S; SO; $SO_2$; or substituted or unsubstituted amnino. $R_1$, $R_2$, $R_3$, $R_4$, $R_5$ and $R_8$, in dependent of one another, are H; —OH; —SH; —O-alkyl; —O-acyl; $C_{1-20}$ alkyl; $C_{1-20}$ acyl; halogen; silyl; sulfonate; and unsubstituted or substituted amino. $R_6$ is H; $C_{1-20}$ alkyl or alkoxy; $C_{1-20}$ acyl or acyloxy; hydroxymethylcarbonyl; alkoxymethylcarbonyl; acyloxymethylcarbonyl; $C_{7-20}$ aryl or aryloxy; squaric acid and salts thereof; phosphonate; or a 5 or 6 membered heterocycle. R6' is H; halogen; $C_{1-20}$ alkyl or alkyloxy; unsubstituted or substituted amino; —OH; —SH; —CN; sulfide; and $C_{1-20}$ acyl or acyloxy. Y and $R_7$, independent of one another, are H; halogen; —OH; alkoxy; $C_{1-20}$ alkyl; —CN; amino; $C_{1-20}$ acyl or acyloxy; or a saccharide or modified saccharide. Tautomers, such as leuco isomers, are understood by those of ordinary skill in the art, to be included in the category of anthracyclines.

One of ordinary skill in the art recognizes that 1,2-dihetero-substituted anti-cancer drugs, and anthracyclines in particular, contain many stereocenters and that it is within the skill of one in the art using routine methods and materials to change the stereochemistry of the various stereocenters, yielding numerous isomers, include enantiomers and diastereomers. These isomers are within the scope of this invention, as are pharmaceutical compositions containing various, e.g. non-equal, amounts of various isomers. It is known to those in the art how to determine the optical purity of a mixture of isomers and to test whether such a mixture is pharmaceutically acceptable. Compositions containing racemic and non-racemic mixtures of the compounds are within the scope of this invention. Compositions having varying levels of optical purity are within the scope of this invention.

Within the anthracycline class of anti-cancer drugs are several families (Abdella, B. R. J. and Fisher, J. A. (1985) Envir. Health Perspect. 64:3–18). Formulas XII A, B and C show several families of anthracycline drugs. One family is the daunorubicin family, another is the aclacinomycin family, another is the nogalamycin family. Within each family are numerous derivatives.

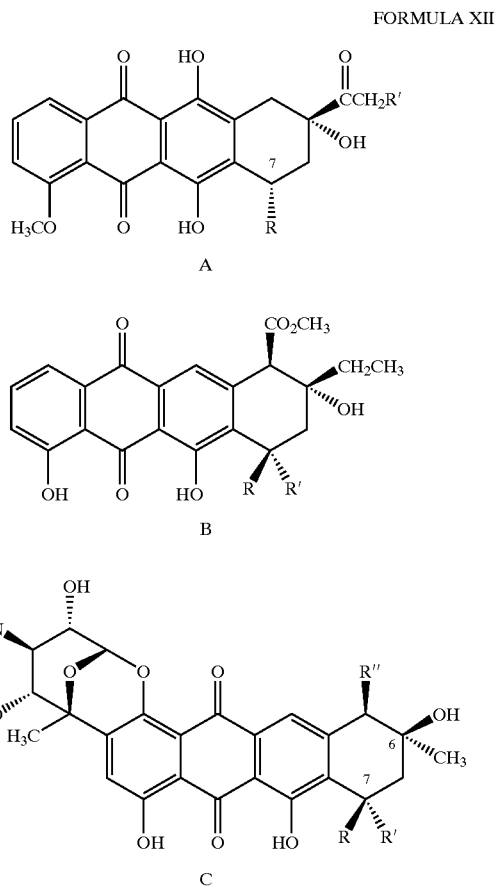

FORMULA XII

Anthracyclines, anthracylinones (aglycones) which have —OH in place of the glycoside) and 7-deoxyanthracylinones which have —H in place of the glycoside: (A) Daunorubicin family: (A1) daunorubicin (R=L-daunosamine, R'=H); (A2) 7-deoxydaunorubicinone (R=R'=H); (A3) daunrorubicinone=(R=OH, R'=H); (A4) doxorubicin (R=L-daunosamine, R'=OH); (A5) epidoxorubicin (R=4'-epi-L-daunosamine, R'=OH). (B) Aclacinomycin family: (B1) aclacinomycin A (R'=L-rhodosamine-2-deoxy-L-fucose-L-cinerulose A, R=H); (B2) 7-deoxyaklavinone (R=R'=H); (B3) aklavinone (R'=OH, R=H). (C) Nogalamycin family: (C1) nogalamycin (R=H, R'=nogalose, R"=$CO_2CH_3$); (C2) 7-deoxynogalarol (R=R'= H, R"=$CO_2CH_3$); (C3) 7R-nogamycin (R=nogalose, R'=R"= H); (C4) menogaril (R=$OCH_3$, R'=R"=H); (C5) epimenogaril (R'=$OCH_3$, R=R"=H); (C6) 7-deoxynogarol ((R=R'= R"=H).

This invention particularly provides formaldehyde conjugates made from anthracyclines having the general structure shown in Formula XIII.

Formula XIII

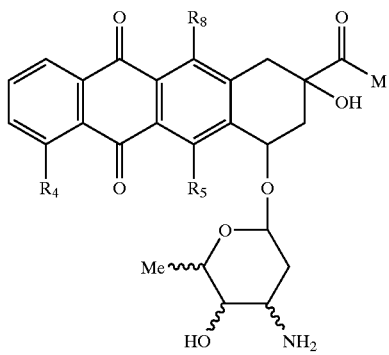

In Formula XIII, $R_4$, $R_5$, and $R_8$ are as described in Formula XI. M can be chosen from the following, non-limiting examples: alkyl or alykenyl, either having from 1 to about 20 carbons, or from 1 to about 8 carbons, preferably —$CH_3$; —$CH_2OH$; —$CH_2$—O—alkyl; —$CH_2$—O-acyl.

More particularly, this invention provides formaldehyde conjugates made from compounds of the general structure shown in Formulas XIVA, B, C, D, E and F.

Formula XIV

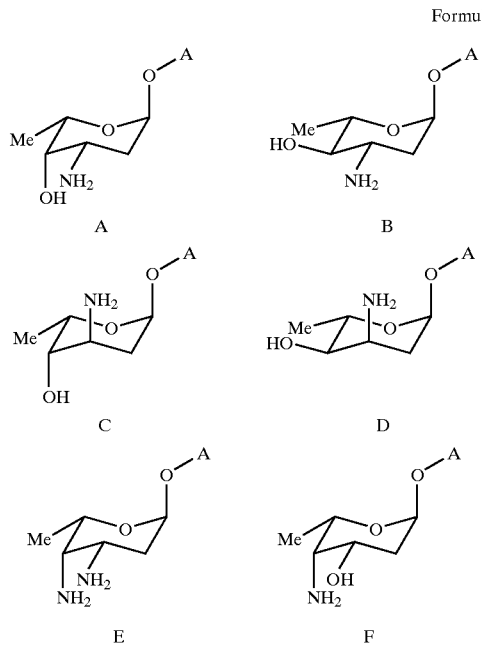

The letter A is as defined above, e.g., the 7-deoxyaglycon portion of an anthracycline attached at its 7-position. Formulas XIVA and XIVB differ from each other only in the epimerization of the carbon bearing the hydroxyl group. Formulas XIVC and XIVD differ from each other only in the epimerization of the carbon bearing the hydroxyl group. Formulas XIVA and XIVC differ from each other only in the epimerization of the carbon bearing the amino group. Formulas XIVB and XIVD differ from each other only in the epimerization of the carbon bearing the amino group. Formula XIVE shows a 1,2-diamino substituted anti-cancer drug. Formula XIVF shows a regioisomer of the drug in Formula XIVA. Formula XIV illustrates only a few of the possible anti-cancer drug structures. Those of ordinary skill in the art recognize that many more structures can be realized by changing stereochemistry, regiochemistry and substitution of the structures illustrated. The structures of Formula XIV represent non-limiting examples of anthracycline structures.

Also included in this invention are formaldehyde conjugates made from compounds of the general formula shown in Formulas XVA, B, C, D, E, and F.

Formula XV

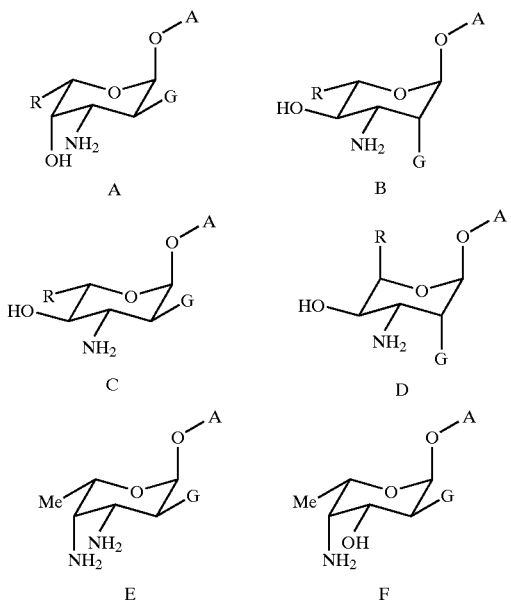

In Formula XV, A is defined as above. In these structures the sugar is substituted at the 2'-position. As is known to those of ordinary skill in the art, G can be chosen from the following, non-limiting examples: —OH; $C_{1-20}$ alkyl; $C_{1-20}$ acyl; halogen silyl; sulfonate; sulfonyl; unsubstituted or substituted amino; $C_{7-20}$ aryl or aryloxy; squaric acid and salts thereof; phosphonate; or a 5 or 6 membered heterocycle. Formula XV illustrates only a few of the possible anti-cancer drug stuctures; many more structures can be realized by changing stereochemistry, regiochemistry and substitution.

The preparation and characterization of the dimeric formaldehyde conjugate of daunorubicin and the dimeric formaldehyde conjugate of doxorubicin are described in Fenick et al. (197) J. Med. Chem. 40, 2452–2461, as well as in Examples 1–47 below. The structures of both conjugates were determined from spectroscopic data, including positive ion electrospray mass spectra of the dimeric formaldehyde conjugate of daunorubicin and the dimeric formaldehyde conjugate of doxorubicin. $_1$H NMR spectra established the structures as bis(3'-N-(3',4'-O-methylenedaunorubicinyl)) methane and bis(3'-N-(3',4'-O-methylenedoxorubicinyl) methane (the dimeric formaldehyde conjugate of daunorubicin and the dimeric formaldehyde conjugate of doxorubicin, respectively, Scheme III).

The dimeric formaldehyde conjugate of daunorubicin was stable for a period of days in dry deuteriochloroform. Addition of a drop of deuterium oxide to the deuteriochloroform solution resulted in the formation of a mixture of the dimeric formaldehyde conjugate of daunorubicin with the mono-oxazolidine (3'-N,4'-O-methylenedaunorubicin) as established by periodic monitoring of the $_1$H NMR spectrum. The structure for the oxazolidine was determined by $_1$H NMR.

The dimeric formaldehyde conjugate of daunorubicin and formaldehyde react with the self complementary DNA, (GC)$_4$, to yield four drug-DNA conjugates bearing virtual cross-links, denoted conjugates A–D (as described in Taatjes, D. J. et al. (1996) J. Med. Chem. 39:4135–4138 and in Taatjes, D. J. et al. (1997) J. Med. Chem. 40, 1276–1286). UV-vis absorption and electrospray mass spectrometry indicated that two conjugates (A and B) contained one molecule of daunorubicin per double stranded DNA (dsDNA), and two other conjugates (C and D) contained two molecules of daunorubicin per dsDNA. Reaction of (GC)$_4$ with the dimeric formaldehyde conjugate of daunorubicin in pH 7.4 phosphate buffer gave the same four drug-DNA conjugates (A–D) plus a significant amount of a fifth conjugate (E) which appeared at longer retention time in the reverse phase HPLC. The fifth conjugate (E) was observed in the earlier experiments with daunorubicin and formaldehyde but was not produced in sufficient quantities for characterization. UV-vis absorption indicated that the fifth contains three molecules of daunorubicin per dsDNA.

The term "virtual cross-link" as used herein refers to a nucleic acid, (mitochondrial, nuclear, or synthetic DNA, or RNA in which the nucleic acid has at least a portion of double strandedness, e.g., a section of RNA which has folded back on itself and has complementrary base pairs aligned for base-pairing) and in which one strand is covalently bound to an anti-cancer drug, e.g., anthracycline, molecule, for example by a methylene (derived from an anlehyde, e.g., formaldehyde) on the 3'-amino group of an anthracycline sugar, and the other strand of the nucleic acid is hydrogen bonded to the anti-cancer drug. The term "virtual cross-link" is distinghished from the term "cross-link," in which both strands of the nucleic acid are covalently bound to the anti-cancer molecule.

The term "drug-DNA conjugates" refers to a DNA which is covalently bound to a drug, and includes "covalent adducts," as well as "virtual cross-links."

The rate of reaction of (GC)$_4$ with the dimeric formaldehyde conjugate of daunorubicin in pH 7.4 phosphate buffer was also compared to the rate of its reaction with a mixture of daunorubicin and formaldehyde. These experiments were performed at much lower concentrations of the dimeric formaldehyde conjugate of daunorubicin (55 μM) such that the major drug-DNA conjugates were A and B. The amount of daunorubicin and formaldehyde employed was equivalent to that present in the dimeric formaldehyde conjugate of daunorubicin experiment. Formation of the. DNA conjugates as a function of time for the two reactions at 25° C. is shown in FIG. 1. After approximately 1 min, the dimeric formaldehyde conjugate of daunorubicin had reacted with four times as much (GC)$_4$ as the equivalent amount of daunorubicin and formaldehyde. The difference in rate of conjugate formation in these two experiments most likely reflects a difference in the overall mechanism. Three possible reaction sequences for the formation of drug-DNA conjugates from daunomycin+dsDNA+formaldehyde are outlined in Scheme VII.

Scheme VII daunorubicin + formaldehyde:

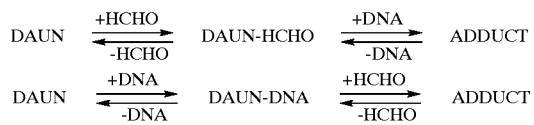

DAUNF:

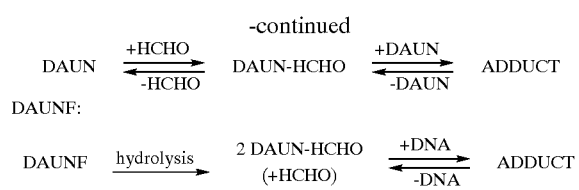

For all of these mechanisms, two sequential bimolecular reactions must occur. In the case of the dimeric formaldehyde conjugate of daunorubicin+dsDNA, the mechanism of drug-DNA conjugate formation probably involves a first order decay followed by one bimolecular reaction (Scheme VII). Thus, the enhanced rate of drug-DNA conjugate formation for the the dimeric formaldehyde conjugate of daunorubicin+dsDNA system is presumably a reflection of the fact that one less bimolecular reaction needs to occur.

The biological activities of the dimeric formaldehyde conjugate of daunorubicin and the dimeric formaldehyde conjugate of doxorubicin were determined by their in vitro cytotoxicity against MCF-7 and MCF-7/ADR cell lines. MCF-7 is a sensitive human breast carcinoma line whereas MCF-7/ADR is its doxorubicin-resistant counterpart (Cowan, K. H. et al. (1986) Proc. Natl. Acad. Sci. USA 83:9328–9332). IC$_{50}$ values for the dimeric formaldehyde conjugate of daunorubicin, the dimeric formaldehyde conjugate of doxorubicin, daunorubicin, and doxorubicin are shown in Table 1:

TABLE 1

| Cell Type | IC$_{50}$ Values (nmol equiv/L) | | | |
|---|---|---|---|---|
| | DOX | DOXF | DAUN | DAUNF |
| MCF-7 | 300 | 2 | 60 | 8 |
| MCF-7-ADR | 10,000 | 1 | 2,000 | 10 |

DOX = doxorubicin;
DOXF = the dimeric formaldehyde conjugate of doxorubicin;
DAUN = daunorubicin;
DAUNF = the dimeric formaldehyde conjugate of daunorubicin.

The term IC$_{50}$ as used herein refers to the concentration of drug which inhibits cell growth by 50%, i.e., 50% of cells are viable at the IC$_{50}$ concentration relative to a no-drug control.

Cells were incubated with drug for 3 h in RPMI (Roswell Park Memorial Institute) 1640 media containing 10% fetal bovine serum and 1% DMSO. Plates, were developed using the crystal violet assay. The units are nmol equiv/L because the dimeric formaldehyde conjugate of doxorubicin and the dimeric formaldehyde conjugate of daunorubicin each contain two anthracycline equivalents. In all cases percent survival was determined by the extent of colony formation six days after drug treatment. The dimeric formaldehyde conjugate of daunorubicin and the dimeric formaldehyde conjugate of doxorubicin were 7 and 150 times more cytotoxic against the MCF-7 cell line than daunorubicin and doxorubicin, respectively. The dimeric formaldehyde conjugate of doxorubicin showed a dramatic 10,000-fold higher cytotoxicity against the MCF-7/ADR cell line relative to doxorubicin, and the dimeric formaldehyde conjugate of daunorubicin showed a 200-fold higher cytotoxicity relative to daunorubicin. Control experiments established that neither formaldehyde nor 1% DMSO were cytotoxic to MCF-7 or MCF-7/ADR cells in the concentration ranges employed in the experiments.

Figure 2:
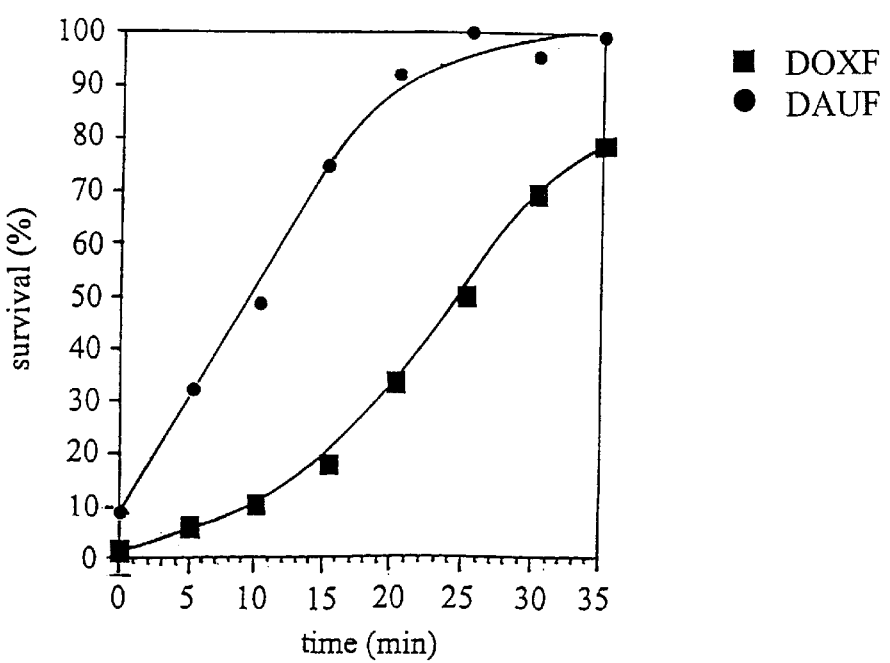
FIG. 2 is a graph of cell survival versus time of pre-incubation of the dimeric formaldehyde conjugate of daunorubicin and the dimeric formaldehyde conjugate of doxorubicin in cell media. Cytotoxicity of 1 $\mu$mol equiv./L of the dimeric formaldehyde conjugate of daunorubicin and the dimeric formaldehyde conjugate of doxorubicin to MCF-7/ADR cells as a function of the time allowed for drug hydrolysis, in serum-free media containing 10% DMSO, prior to treatment is shown.

The observed cytotoxicity of the dimeric formaldehyde conjugate of daunorubicin and the dimeric formaldehyde conjugate of doxorubicin represent a lower limit due to their rapid hydrolysis in an aqueous environment. To demonstrate this point, the survival of the dimeric formaldehyde conjugate of doxorubicin and the dimeric formaldehyde conjugate of daunorubicin treated MCF-7/ADR cells was measured as a function of time during which the drugs were allowed to stand in an aqueous environment at 25° C. for various time periods prior to addition to the cells. The results of these experiments are illustrated in FIG. 2. For both drugs at t=0 min, cells showed a survival rate of less than 10%. However, the dimeric formaldehyde conjugate of daunorubicin completely lost its effectiveness within 25 min of standing in an aqueous solution. The dimeric formaldehyde conjugate of doxorubicin showed a somewhat longer lifetime and a curious biphasic survival curve. This biphasic curve is probably due to the decay mechanism of the dimeric formaldehyde conjugate of doxorubicin to doxorubicin in aqueous solution. Although the $IC_{50}$ values reported in Table 1 were obtained using a 3 h incubation time, the actual exposure time to the cytotoxic component of the dimeric formaldehyde conjugate of daunorubicin and the dimeric formaldehyde conjugate of doxorubicin was much shorter.

The 4'-epimer of doxorubicin (epidoxorubicin, also known in the art as epirubicin) is a diastereoisomer of doxorubicin with the alcohol at the 4'-position epimerized. It is a broad spectrum drug similar to doxorubicin and is marketed worldwide except in the U.S. (Sweatman, T. W.; Israel, M. Anthracyclines. In: Teicher B A, ed. Cancer Therapeutics, Experimental and Clinical Agents. Totowa, N.J.: Humana Press, 1997:113–135). The primary pharmacological difference between doxorubicin and epidoxorubicin is that epidoxorubicin is converted to a glucuronide derivative, at the 4'-hydroxyl group. Glucuronides have been observed in the urine of patients receiving epidoxorubicin but not in the urine of patients receiving doxorubicin (Weenen, H. et al. (1984) Eur. J. Cancer Clin. Oncol. 20, 919–926). Glucuronide conjugation leads to faster drug clearance. Like doxorubicin, epidoxorubicin intercalates in DNA, forms DNA crosslinks in HeLa S3 cells, and causes topoisomerase II-mediated strand breaks (Skladanowski, A. and Konopa, J. Biochem. Pharmacol. (1994) 47, 2269–2278; d'Estaintot, B. L. et al. Nucleic Acids Res. (1992) 20, 3561–3566; Cantonio, O. et al. Cancer Chemother. Pharmacol. (1990) 27, 47–51).

Epidoxorubicin reacts with formaldehyde at its amino alcohol functionality to produce an anthracycline formaldehyde conjugate, the dimeric formaldehyde conjugate of epidoxorubicin, whose structure consists of two molecules of epidoxorubicin bound together with three methylene groups in a 1,6-diaza-4,9-dioxabicyclor[4.4.1]undecane ring system, as described in Taatjes, D. J. et al. J. Med. Chem. in press. See Example 15 and Scheme VI. The structure was established from spectroscopic data. The dimeric formaldehyde conjugate of epidoxorubicin hydrolyzes at pH, 7.3 to an equilibrium mixture with dimeric and monomeric epidoxorubicin-formaldehyde conjugates without release of formaldehyde or epidoxorubicin. The hydrolysis follows the rate law (A⇌B)⇌C+D where A (the dimeric formaldehyde conjugate of epidoxorubicin) is in rapid equilibrium with B, and B is in slow equilibrium with C and D. The forward rate constant for A⇌B going to C+D gives a half-life of approximately 2 h at 37° C. At equilibrium the mixture is stable for at least 2 days. At pH 6.0, hydrolysis proceeds with first order kinetics to epidoxorubicin and formaldehyde with a half-life of 15 min at 37° C. The dimeric formaldehyde conjugate of epidoxorubicin, and epidoxorubicin plus formaldehyde, react with the self-complementary DNA octamer $(GC)_4$ to yield 5 drug-DNA conjugates bearing virtual cross-links which have structures analogous to the doxorubicin-DNA conjugates from reaction of the dimeric formaldehyde conjugate of doxorubicin with $(GC)_4$. The dimeric formaldehyde conjugate of epidoxorubicin is 3-fold more toxic to MCF-7 human breast cancer cells and greater than 120-fold more toxic to MCF-7/ADR resistant cells than epidoxorubicin. The dimeric formaldehyde conjugate of epidoxorubicin in equilibrium with its hydrolysis products is greater than 25-fold more toxic to resistant cells with respect to epidoxorubicin.

Figure 3:
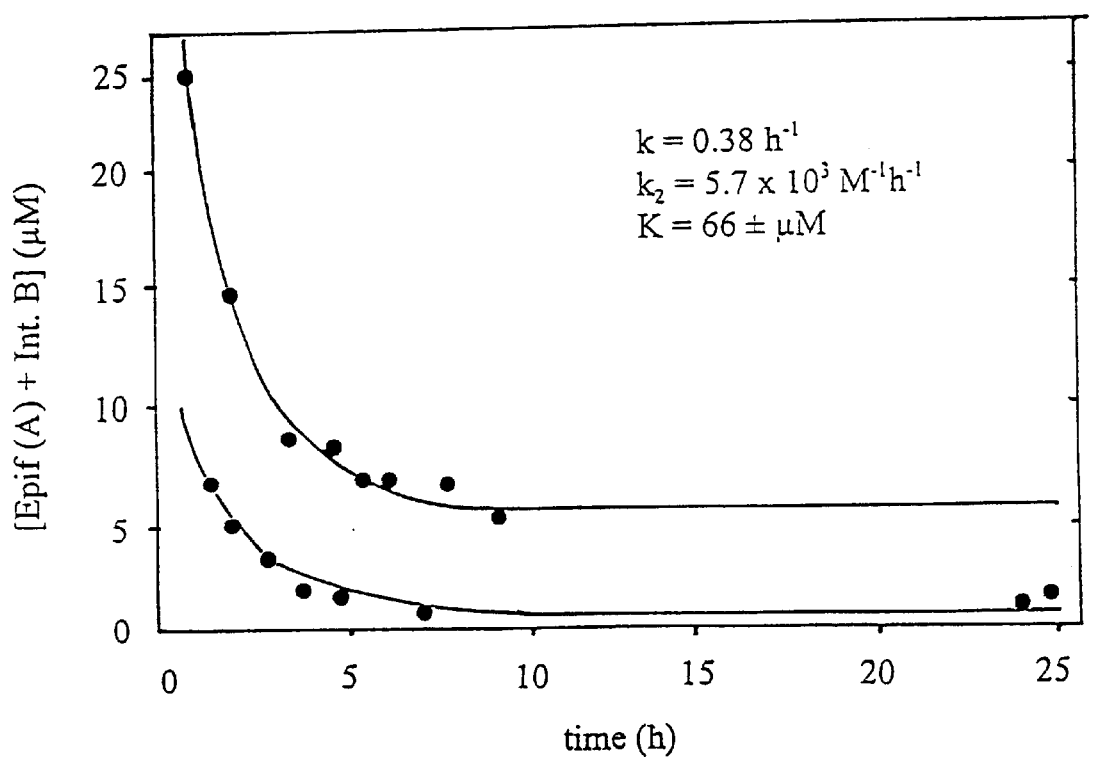
FIG. 3 is a graph showing disappearance of the equilibrium mixture of the dimeric formaldehyde conjugate of epidoxorubicin and Intermediate B as a function of time and initial concentration of the dimeric formaldehyde conjugate of epidoxorubicin in pH 7.3 phosphate buffer at 37° C. The dots represent the data and the solid lines represent the fit of the data to the kinetic mechanism $(A \rightleftharpoons B) \rightleftharpoons C + D$ as shown in Scheme VI using the program Mathematica for numerical integration.

The dimeric formaldehyde conjugate of epidoxorubicin is very stable with respect to hydrolytic loss of formaldehyde. See Example 16. Hydrolysis of the dimeric formaldehyde conjugate of epidoxorubicin at 37° C. in pH 7.3 phosphate buffer containing 4% DMSO was monitored by reverse phase HPLC. The DMSO was present to increase solubility. The disappearance as a function of time is shown in FIG. 3 starting with 25 $\mu$M and 10 $\mu$M the dimeric formaldehyde conjugate of epidoxorubicin. Surprisingly, the reaction does not proceed to completion but comes to an equilibrium.

The hydrolysis was also examined by $^1$H NMR spectroscopy in DMSO-$d_6$. The dimeric formaldehyde conjugate of epidoxorubicin was indefinitely stable in dry DMSO-$d_6$; however, upon addition of 7% $D_2O$, it rapidly formed a 2:1 equilibrium mixture with an intermediate with loss of no more than a trace of formaldehyde. The structure for the intermediate is the ten membered ring-structure (intermediate B) shown in Scheme VI as determined on the basis of the NMR spectral data and the kinetic data which require a mechanism with one species slowly equilibrating with two species. In this case the one species is intermediate B which is in rapid equilibrium with the dimeric formaldehyde conjugate of epidoxorubicin, and the two species are intermediates C and D. The equilibrium mixture of the dimeric formaldehyde conjugate of epidoxorubicin with intermediate B in 93% DMSO-$d_6$/7% $D_2O$ was stable for days as indicated by $^1$H NMR monitoring.

The $^1$H NMR spectrum of the hydrolysis reaction mixture resulting from equilibration of approximately 25 $\mu$M the dimeric formaldehyde conjugate of epidoxorubicin in 96% $D_2O$/4% DMSO-$d_6$ at 37° C. was also observed. This reaction mixture was analogous to the mixture present at equilibrium in the kinetic experiment shown in FIG. 3, except for deuterium isotope effects and the effect of no buffer. The NMR spectrum indicates that intermediates C and D (Scheme VI) are actually the products of the reaction. They are called intermediates because they still bear formaldehyde. Intermediate C is in equilibrium with intermediate D and formaldehyde, and intermediate D is in equilibrium with epidoxorubicin and formaldehyde. These latter equilibria must favor intermediates C and D, respectively, at the experimental concentrations because epidoxorubicin was not apparent in the $^1$H NMR.

The kinetics of hydrolysis of the dimeric formaldehyde conjugate of epidoxorubicin were also observed in pH 7.4 RPMI 1640 media containing 10% fetal bovine serum and in pH 8.1 fetal bovine serum, both at 37° C. with HPLC monitoring. In both cases the reaction kinetics were similar to those shown in FIG. 3 for the reaction in pH 7.3 phosphate buffer. The data suggest that the half-life of the equilibrium mixture of the dimeric formaldehyde conjugate of epidoxorubicin and intermediate B will be at least 2 h in serum at 37° C. with respect to formation of intermediates C and D. The half-lives of intermediates C and D may be even longer but could not be determined with the available techniques. This is substantial when compared with an estimated half-life for the dimeric formaldehyde conjugate of daunorubicin and the dimeric formaldehyde conjugate of doxorubicin of less than 10 min.

The effect of acid on the hydrolysis of the dimeric formaldehyde conjugate of epidoxorubicin was also studied. First, the equilibrium mixture of the dimeric formaldehyde conjugate of epidoxorubicin and intermediate B in 93% DMSO-$d_6$/7% $D_2O$ was titrated with aliquots of HCl ranging from 0.5 to 2.0 mol equiv. Upon each addition of HCl, equivalent amounts of epidoxorubicin and formaldehyde were released as indicated by the $^1H$ NMR spectrum and no additional intermediates were observed. Second, the kinetics of hydrolysis were measured in pH 6.0 phosphate buffer. Under these conditions the reaction proceeded to completion with formation of epidoxorubicin with simple first order kinetics as shown in Scheme VIII. The half-life at 37° C. is only 15 min. In both experiments the reaction is driven toward epidoxorubicin and formaldehyde most likely because of the protonation of the 3'-amino group of epidoxorubicin.

the dimeric formaldehyde conjugate of epidoxorubicin yielded 5 drug-DNA conjugates as indicated by reverse phase HPLC. UV-visible absorption indicated that the drug-chromophore was intercalated between base pairs and that conjugates with shorter HPLC retention times contained one drug molecule pet dsDNA (conjugates 1 and 2) and that conjugates with longer retention times contained two drug molecules per dsDNA (conjugates 3, 4, and 5). Like doxorubicin and daunorubicin-DNA conjugates, all of the epidoxorubicin-DNA conjugates were hydrolytically unstable with respect to release of the drug from the DNA. With careful control of pH, the conjugates were collected individually as they eluted from the HPLC column and analyzed by negative ion electrospray mass spectrometry. The mass spectra showed the appearance of peaks corresponding to one drug molecule bound to a single strand of DNA via one methylene group as well as peaks for DNA. It also shows a small peak for ssDNA bound to 2 molecules of epidoxorubicin with methylene groups. The same 5 drug-DNA conjugates were observed from reaction of $(GC)_4$ with

SCHEME VIII

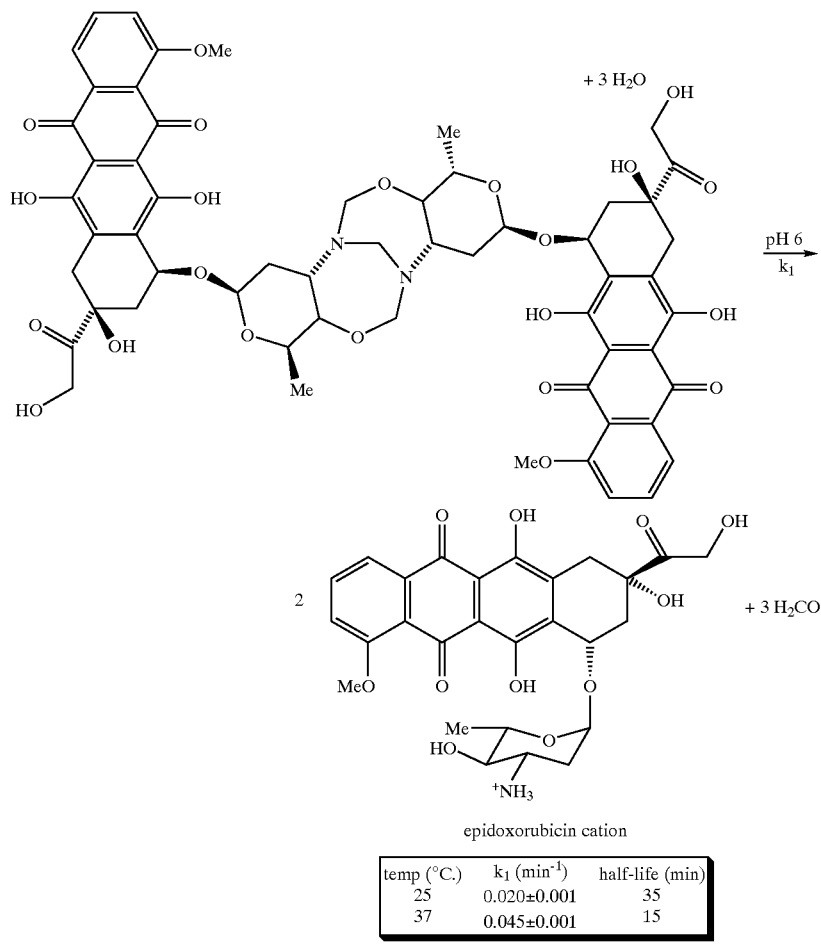

| temp (°C.) | $k_1$ (min$^{-1}$) | half-life (min) |
|---|---|---|
| 25 | 0.020±0.001 | 35 |
| 37 | 0.045±0.001 | 15 |

Reaction of the dimeric formaldehyde conjugate of epidoxorubicin and epidoxorubicin with DNA is described next. See Examples 17–20. The self-complementary 2'-deoxyoligonucleotide (GC), was used for reactions with the dimeric formaldehyde conjugate of epidoxorubicin and epidoxorubicin plus formaldehyde. Reaction of $(GC)_4$ with epidoxorubicin plus an equivalent amount of formaldehyde. Structures analogous to those of doxorubicin and daunorubicin bonded to $(GC)_4$ are proposed for the conjugates of epidoxorubicin bound to $(GC)_4$. In these structures, the chromophore of the drug is intercalated between 5'-CpG-3' of 5'-CpGpC-3' and the amino sugar in the minor groove is covalently linked via a methylene group from its 3'-amino substituent to the 2-amino substituent of the third G base of the opposing strand.

Toxicity of the dimeric formaldehyde conjugate of epidoxorubicin to MCF-7 human breast cancer cells and their doxorubicin resistant counterpart (MCF-7/ADR cells) relative to the toxicity of epidoxorubicin was determined as described previously for the dimeric formaldehyde conjugate of doxorubicin and the dimeric formaldehyde: conjugate of daunorubicin. The resulting $IC_{50}$ values are compared in Table 2.

TABLE 2

| | $IC_{50}$ Values (nmol equiv./L) | | | | | | | |
|---|---|---|---|---|---|---|---|---|
| Cell Type | EPI | EPIF | EPIF/ DMSO | EPIF/ $H_2O$ | DOX | DOXF | DAUN | DAUNF |
| MCF-7 | 200 | 65 | — | — | 300 | 2 | 60 | 8 |
| MCF-7-ADR | >10,000 | 70 | 300 | 400 | 10,000 | 1 | 2,000 | 10 |

EPI = epidoxorubicin;
EPIF = the dimeric formaldehyde conjugate of epidoxorubicin;
DOX = doxorubicin;
DOXF = the dimeric formaldehyde conjugate of doxorubicin;
DAUN = daunorubicin;
DAUNF = the dimeric formaldehyde conjugate of daunorubicin.

The dimeric formaldehyde conjugate of epidoxorubicin is approximately 3-fold more toxic to sensitive cells (MCF-7) than is epidoxorubicin and greater than 120-fold more toxic to resistant cells (MCF-7/ADR). The $IC_{50}$ values show the dimeric formaldehyde conjugate of epidoxorubicin to be about equally toxic to sensitive and resistant cells. These toxicity levels place the dimeric formaldehyde conjugate of epidoxorubicin approximately 7-fold less toxic than the dimeric formaldehyde conjugate of daunorubicin which is approximately 7-fold less toxic than the dimeric formaldehyde conjugate of doxorubicin to both sensitive and resistant breast cancer cells. All three drug formaldehyde conjugates are more toxic to sensitive cells than the bench mark, doxorubicin, and significantly more toxic to resistant cells than doxorubicin.

Because the dimeric formaldehyde conjugate of epidoxorubicin hydrolyzes to an equilibrium mixture with the 10-membered ring (intermediate B) and two hydroxylmethylene conjugates (intermediates C and D) (Scheme VI) in $H_2O$/DMSO, an $IC_{50}$ value versus resistant MCF-7/ADR cells was also determined with this equilibrium mixture of compounds. The mixture was established by preincubation of the dimeric formaldehyde conjugate of epidoxorubicin in 90% $H_2O$/10%,DMSO at 37° C. for 20 h. As an additional control MCF-7/ADR cells were also treated with the dimeric formaldehyde conjugate of epidoxorubicin stored in DMSO (not dried over molecular sieves) for 20 h at ambient temperature. Both of these solutions gave $IC_{50}$ values only 5-fold higher than a fresh solution of the dimeric formaldehyde conjugate of epidoxorubicin, as shown in Table 2.

Comparing the cytotoxicity of the three drugs after being subjected to hydrolysis places them in the following order of activity: the dimeric formaldehyde conjugate of epidoxorubicin>> the dimeric formaldehyde conjugate of doxorubicin> the dimeric formaldehyde conjugate of daunorubicin. This ordering suggests that the stereochemistry of the hydroxyl at the 4'-position and the presence of a hydroxyl at the 14-position are relevant to the stabilization of drug-formaldehyde conjugates. Thus, the dimeric formaldehyde conjugate of epidoxorubicin provides an active agent against resistant cancer with a much longer lifetime in the vascular system than the dimeric formaldehyde conjugate of doxorubicin and the dimeric formaldehyde conjugate of daunorubicin.

A metabolic pathway which inactivates the anti-tumor drug epidoxorubicin is glucuronidation which conjugates the drug at its 4'-hydroxyl to glucuronic acid (Weenen, H. et al. (1984) Eur. J. Cancer Clin. Oncol. 20:919–926). The glucuronic acid conjugate is excreted in the urine. This metabolic pathway does not affect doxorubicin, and glucuronidation may be the reason that epidoxorubicin shows lower animal toxicity than doxorubicin (Sweatman, T. W. and Israel, M. (1997), "Anthracyclines," Cancer Therapeutics, Experimental and Clinical Agents, Teicher, B. A., ed. Totowa, N.J.: Humana Press, pp. 113–135).

Epidoxorubicin was incubated in 10% DMSO/90% RPMI 1640 cell culture media containing 10% fetal bovine serum for 6 h at 37° C. prior to addition to human breast cancer cells (MCF-7 cells). The preincubation increased the $IC_{50}$ value by more than a factor of 50. Corresponding preincubation of the dimeric formaldehyde conjugate of epidoxorubicin increased the $IC_{50}$ value for MCF-7 cells as well as for doxorubicin resistant MCF-7/ADR cells by only a factor of about 5 to 6 (Table 3).

TABLE 3

| | $IC_{50}$ Values (nmol equiv./L) for | | | |
|---|---|---|---|---|
| Cell Type | EPI | EPIF | EPI/ Media/Serum | EPIF/Media/ Serum |
| MCF-7 | 200 | 65 | >10,000 | 400 |
| MCF-7/ADR | >10,000 | 70 | — | 300 |

EPI = epidoxorubicin;
EPIF = the dimeric formaldehyde conjugate of epidoxorubicin.

The enhanced stability of the dimeric formaldehyde conjugate of epidoxorubicin in cell culture media containing serum, compared to epidoxorubicin, with respect to metabolic deactivation indicates that the dimeric formaldehyde conjugate of epidoxorubicin is more stable in the vascular system. The combination of hydrolytic stability, stability in serum and toxicity to doxorubicin resistant and multi-drug resistant tumor cells makes the dimeric formaldehyde conjugate of epidoxorubicin preferred over the dimeric formaldehyde conjugate of doxorubicin and the dimeric formaldehyde conjugate of daunorubicin.

The dimeric formaldehyde conjugate of epidoxorubicin and the dimeric and monomeric epidoxorubicin formaldehyde conjugates from its partial hydrolysis show significant toxicity to resistant breast cancer cells (MCF-7/ADR). Resistance in these cells is proposed to result from a combination of overexpression of enzymes which scavenge reactive oxygen species, overexpression of glutathione transferase, and overexpression of the P-170 glycoprotein efflux pump (Fairchild, C R. et al. Cancer Res 1987, 47, 5141–8). Anthracycline formaldehyde conjugates overcome at least some of these resistance mechanisms. The MCF-7/ADR cell line exhibits decreased intracellular accumulation of doxorubicin compared to its parental line (MCF-7) due to P-glycoprotein (P-GP) overexpression. P-GP works best on positively charged anthracyclines. Doxorubicin analogs with increased lipophilicity have been shown to be retained by cells overexpressing P-glycoprotein, presumably because they are poorer substrates for the efflux pump (Lampidis, T. J. et al. Biochem. 1997, 36, 2679–2685). Because anthracycline aldehyde conjugates, e.g. the dimeric formaldehyde conjugate of doxorubicin, the dimeric formaldehyde conjugate of daunorubicin, and the dimeric formaldehyde conjugate of epidoxorubicin, are more lipophilic than their parent compounds due to their tertiary amine functionality bearing electron withdrawing groups, they can effectively fight this resistance mechanism. For example, empirical rules for predicting pKa's of aminoalcohols give pKa's=8.5, 5.8, 5.8, and 3.1 for epidoxorubicin, intermediate B, intermediate D, and intermediate C, respectively (Inouye, S. Chem. Pharm. Bull. 1968, 16, 1134–1137). These rules suggest that the pKa of the dimeric formaldehyde conjugate of epidoxorubicin is about 3. Hence, at physiological pH, only epidoxorubicin is significantly protonated. Correspondingly, P-glycoprotein is most effective against epidoxorubicin and significantly less effective against the dimeric formaldehyde conjugate of epidoxorubicin and epidoxorubicin formaldehyde conjugates (intermediates B, C, and D).

However, P-glycoprotein overexpression is not the dominant mechanism of drug resistance in MCF-7/ADR cells. The MCF-7/ADR cell line shows only a 2–3 fold difference in drug uptake as compared to the MCF-7 cell line, which is not sufficient to explain the observed drug resistance of up to 200 fold relative to MCF-7 (Batist, G. et al. (1986) J. Biol. Chem. 261:15,544–15,549). Thus, the mechanism thought to be largely responsible for anthracycline drug resistance in MCF-7/ADR cells is reduced production and/or increased scavenging of reactive oxygen species (Sinha, B. K. and Mimnaugh, E. G. (1990) Free Radicals Biol. Med. 8:567–581). Xenografts of the resistant tumor cells in nude mice show overexpression of superoxide dismutase and glutathione peroxidase which neutralize oxidative stress and underexpression of cytochrome P450 reductase which induces oxidative stress in the presence of the anthracyclines (Mimnaugh, E. G. et al. (1991) Biochem. Pharmacol. 42: 391–402). A consequence of this resistance mechanism is the slow production of aldehyde(s), e.g. formaldehyde, through oxidation of intracellular components. Because the anthracycline aldehyde conjugates "carry their own aldehyde" (are covalently bound to a carbon from an aldehyde) reactive oxygen species are not required for the production of an aldehyde. Thus, anthracycline formaldehyde conjugates such as the dimeric formaldehyde conjugate of epidoxorubicin, the dimeric formaldehyde conjugate of daunorubicin and the dimeric formaldehyde conjugate of doxorubicin, which can skip formaldehyde production, effectively bypass this resistance mechanism as well.

An additional mechanism for tumor cell resistance is overexpression of glutathione transferase and formation of glutathione-drug conjugates (Serafino, A. (1998) Anti-Cancer Res. in press). In fact, overexpression of glutathione transferase has been observed in MCF-7/ADR cells (Batist, G. et al. (1986) J. Biol. Chem. 261:15, 544–15, 549). Because the dimeric formaldehyde conjugate of doxorubicin and the dimeric formaldehyde conjugate of daunorubicin hydrolyze to their parent drugs so rapidly, they must be reaching their intracellular target within a very short period of time. Hence, glutathione transferase may not have sufficient time to transform the dimeric formaldehyde conjugate of doxorubicin and the dimeric formaldehyde conjugate of daunorubicin into the less toxic drug-glutathione conjugates.

MCF-7/ADR cells have a mutated p53 gene (Gudas, J. M. et al. (1996) Carcinogenesis 17:1417–1427). The p53protein is part of a complex signaling pathway which slows the growth of normal cells with damaged DNA to allow for DNA repair (Hartwell, L. H. and Kastan, M. B. (1994) Science 266:1821–1828). It also appears to trigger apoptosis in tumor cells with damaged DNA. Consequently, the prognosis is poor for treatment of patients with malignancies having mutated p53 genes using chemotherapeutic agents which attack DNA (Linn, S. C et al. (1996) Br. J. Cancer 74:63–68). Because MCF-7/ADR cells have a mutated p53 gene, anthracycline aldehyde conjugates must be causing tumor cell death by a mechanism which does not require a functioning p53 protein.

The compounds, compositions and methods of this invention are useful in the treatment of cancer in general, and breast and prostate cancer in particular. Prostate cancer is the most common malignant disease of men in the United States causing more than 30,000 deaths per year (Silverberg, E. et al. (1990) CA Cancer J. Clin. 40:9–26). First line treatment is hormone manipulation; however, upon relapse tumors are hormone-resistant. Clinical trials have shown that doxorubicin and mitomycin C are the most effective chemotherapeutics for the treatment of hormone-resistant prostate cancer but that these drugs do not increase survival (Mahler, C & Denis, L. (1992) Cancer 70: 329; Slack, N. H. & Murphy, G. P. (1983) Urology 22: 1). Three prostate cancer cell lines, LNCaP, DU-145, and PC-3, are commonly used to evaluate chemotherapeutic drugs. All are derived from metastatic, hormone-refractory disease. PC-3 and DU-145 are completely hormone-resistant and highly resistant to doxorubicin with $IC_{50}$ values exceeding by several orders of magnitude achievable clinical plasma concentrations of 1 to 0.5 ng/mL (Theyer, G. et al. (1993) J. Urology 150: 1544–1547). LNCaP are relatively hormone-resistant and significantly more sensitive to doxorubicin. Expression of P-glycoprotein efflux pump has been detected in PC-3 and DU-145 cells; however, drug efflux by P-glycoprotein does not appear to be a dominant mechanism for doxorubicin-resistance (Theyer, G. et al. (1993) J. Urology 150: 1544–1547). The effect of conjugation of daunorubicin, doxorubicin, and epidoxorubicin with formaldehyde upon toxicity to all three prostate cancer cell lines is described next.

$IC_{50}$ values for daunorubicin, doxorubicin, and epidoxorubicin are compared with those for the respective anthracycline formaldehyde conjugates, the dimeric formaldehyde conjugate of daunorubicin, the dimeric formaldehyde conjugate of doxorubicin, and the dimeric formaldehyde conjugate of epidoxorubicin, in Table 4.

TABLE 4

IC$_{50}$ Values in nmol equiv./L

| Cell Type/Media | DAU | DAUF | DOX | DOXF | EPI | EPIF |
|---|---|---|---|---|---|---|
| LNCaP/RPMI-1640 | 20 | 6 | 20 | 1 | 20 | 7 |
| DU-145/RPMI-1640 | 100 | 10 | 300 | 4 | 300 | 30 |
| PC-3/RPMI-1640 | 20 | 5 | 30 | 1 | 30 | 7 |
| LNCaP/DMEM | 8 | 3 | 15 | 1 | 20 | 2 |
| DU-145/DMEM | 25 | 8 | 60 | 3 | 40 | 8 |
| PC-3/DMEM | 20 | 1 | 60 | 9 | 60 | 30 |

Toxicity to the three prostate cancer cell lines, LNCaP, DU-145, and PC-3 were measured in two different media, RPMI-1640 and DMEM (Dulbecco's Modified Eagle Medium), both supplemented with 10% fetal bovine serum. RPMI-1640 contains glutathione and DMEM does not. In all cases the anthracycline formaldehyde conjugates were more cytotoxic than the parent drugs. The difference was larger in RPMI-1640 than in DMEM. The anthracycline formaldehyde conjugates were one to two orders of magnitude more toxic to the doxorubicin-resistant cell lines, DU-145 and PC-3 and approximately one order of magnitude more toxic to the doxorubicin-sensitive cell line, LNCaP. Of the three anthracycline formaldehyde conjugates, the dimeric formaldehyde conjugate of doxorubicin was the most, cytotoxic in general. IC$_{50}$ values for all of the anthracycline formaldehyde conjugates were generally within one order of magnitude of the achievable clinical plasma concentration.

The data in Table 4 indicate that anthracycline formaldehyde conjugates overcome prostate cancer cell resistance. This indicates that some resistance originates with expression of enzymes responsible for drug-induced oxidative stress leading to formaldehyde production. This includes overexpression of enzymes which scavenge superoxide and hydrogen peroxide such as superoxide dismutase and glutathione peroxidase and underexpression of enzymes which produce superoxide through reduction of anthracyclines such as cytochrome P450 reductase.

The uptake of 1 micro equiv/L of daunorubicin, doxorubicin, and epidoxorubicin versus the dimeric formaldehyde conjugate of daunorubicin, the dimeric formaldehyde conjugate of doxorubicin, and the dimeric formaldehyde conjugate of epidoxorubicin, by human breast cancer cells was measured by flow cytometry. Concentration of drug is given in micro equiv/L because the dimeric formaldehyde conjugate of daunorubicin, the dimeric formaldehyde conjugate of doxorubicin, and the dimeric formaldehyde conjugate of epidoxorubicin are dimeric in active drug. Both doxorubicin-sensitive MCF-7 cells and doxorubicin-resistant MCF-7/ADR cells were studied. Relative drug uptake was established as a function of time using the cells' mean fluorescence at 570–600 nm as a measure of drug concentration in cells. The methodology was as described earlier by Durand and Olive (Durand, R. E. & Olive, P. L. (1981) Cancer Res. 41: 3489–3494).

Figure 4A:
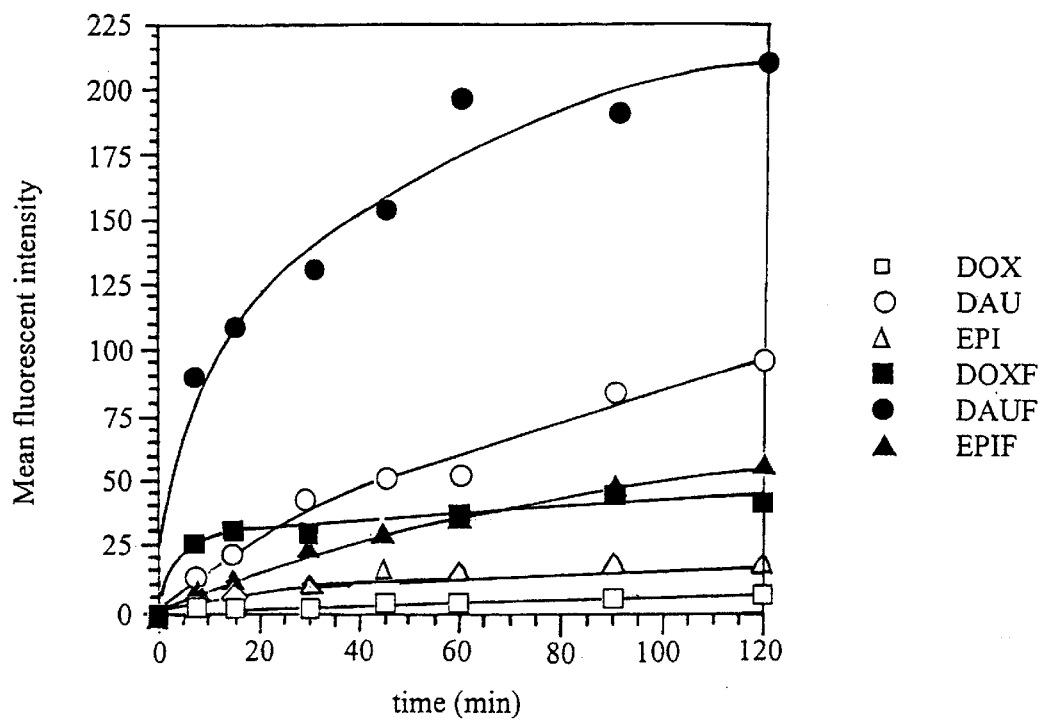
FIGS. 4A and 4B are graphs of drug fluorescence intensity in cells versus time, indicating drug uptake for MCF-7 cells (A) and MCF-7/ADR cells (B).
Figure 4B:
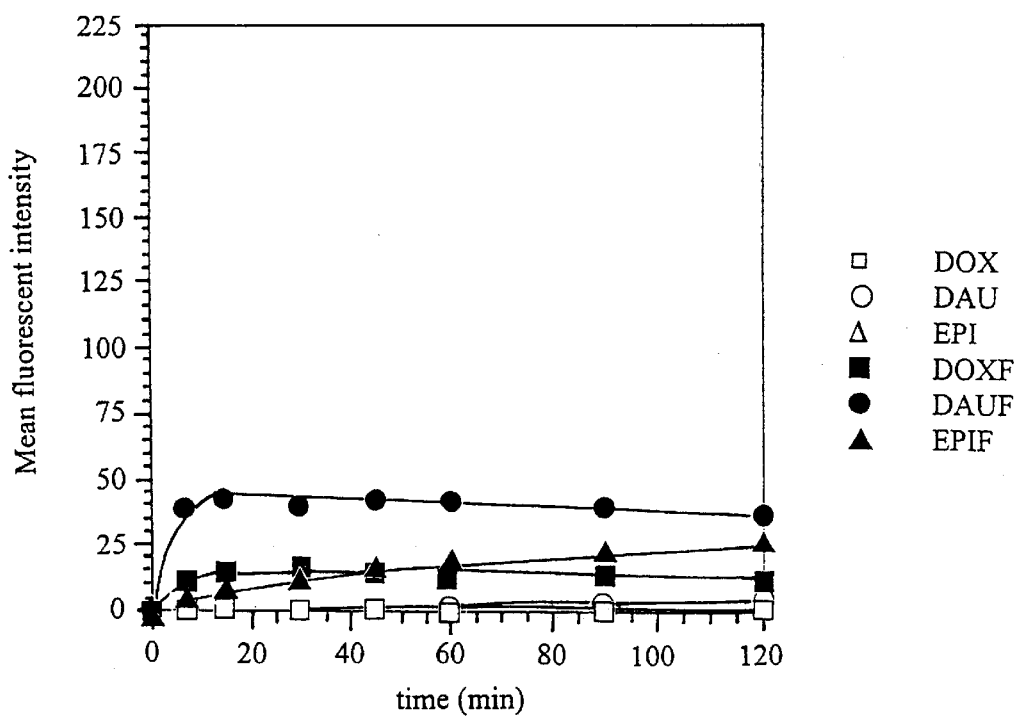

Drug uptake was monitored over a 2 h time period, and the results are plotted in FIGS. 4A and 4B. FIGS. 4A and 4B show the results of flow cytometric measurements of relative drug uptake by (A) doxorubicin-sensitive MCF-7 human breast cancer cells and by (B) doxorubicin-resistant MCF-7/ADR cells in RPMI 1640 media as a function of drug exposure time. For each experiment cells were treated with 1 micro equiv/L of drug. After 2 h, the dimeric formaldehyde conjugate of daunorubicin was taken up the most by both MCF-7 and MCF-7/ADR cells followed by daunorubicin, the dimeric formaldehyde conjugate of epidoxorubicin, the dimeric formaldehyde conjugate of doxorubicin, epidoxorubicin, and doxorubicin. The sensitive cells took up approximately twice as much of the anthracycline formaldehyde conjugates as the respective parent drug. In resistant cells, less of every drug was taken up; however, the ratio of uptake by anthracycline formaldehyde conjugates to parent drug was substantially higher. In fact, very little of the parent drugs were taken up by the resistant cells. The initial rate of uptake by the dimeric formaldehyde conjugate of daunorubicin and the dimeric formaldehyde conjugate of doxorubicin was substantially higher than by the dimeric formaldehyde conjugate of epidoxorubicin. This may reflect the observed difference in the rate of hydrolysis of the the dimeric formaldehyde conjugate of daunorubicin and the dimeric formaldehyde conjugate of doxorubicin versus the dimeric formaldehyde conjugate of epidoxorubicin.

The location of drug in doxorubicin-sensitive and doxorubicin-resistant MCF-7 cells was observed by confocal microscopy, again relying on drug fluorescence as a measure of drug concentration. All six drugs were investigated as a function of drug dose and time of exposure. (Table 5)

TABLE 5

Drug Location

| Drug | Cell Line | 5 min treatment/ 0 min. Recovery | 1 h treatment/ 0 h Recovery' | 1 h treatment/ 3 h Recovery' | 1 h treatment/ 7 h Recovery |
|---|---|---|---|---|---|
| DAU | MCF-7 | Faint nuclear/faint cytoplasm | Nuclear | Nuclear/punctate | Faint nuclear/punctate |
| DAU | MCF-7-ADR | Faint nuclear/faint cytoplasm | Faint cytoplasmic punctate | Faint cytoplasmic punctate | Faint cytoplasmic punctate |
| DAUF | MCF-7 | Faint cytoplasm/Faint nuclear | Nuclear/Faint cytoplasm | Nuclear/cytoplasm/cytoplasmic punctate | Faint nuclear/cytoplasmic punctate |
| DAUF | MCF-7-ADR | Nuclear/punctate | Faint cytoplasmic punctate | Faint cytoplasmic punctate | Faint cytoplasmic punctate |
| DOX | MCF-7 | BDL* | Nuclear | Faint nuclear | Faint nuclear |
| DOX | MCF-7-ADR | BDL* | Faint nuclear | BDL* | BDL* |
| DOXF | MCF-7 | Nuclear | Nuclear | Nuclear | Faint nuclear |
| DOXF | MCF-7- | Nuclear/ | Nuclear/ | Faint cytoplasmic | Faint cytoplasmic |

TABLE 5-continued

| | | Drug Location | | | |
|---|---|---|---|---|---|
| Drug | Cell Line | 5 min treatment/ 0 min. Recovery | 1 h treatment/ 0 h Recovery' | 1 h treatment/ 3 h Recovery' | 1 h treatment/ 7 h Recovery |
| EPI | ADR MCF-7 | cytoplasmic punctate Cytoplasm | cytoplsmic punctate Nuclear/cytoplasm/ plasmic punctate | punctate Nuclear | punctate — |
| EPI | MCF-7-ADR | Cytoplasm punctate | Cytoplasm | Faint cytoplasmic | — |
| EPIF | MCF-7 | Cytoplasm | Nuclear/cytoplasmic punctate | Nuclear/cytoplasmic punctate | — |
| EPIF | MCF-7-ADR | Faint cytoplasmic punctate | Faint nuclear/cytoplasmic punctate | Cytoplasmic punctate | — |

*BDL = Below Detection Limit

In general, more drug appeared in cells treated with anthracycline formaldehyde conjugates. Further, anthracycline formaldehyde conjugates appeared in the nucleus of both sensitive and resistant cells, whereas parent drugs did not appear in the nucleus of resistant cells or appeared in only small amounts. Again, for these experiments, the dose (1 or 5 micro equiv/L) required for drug detection was substantially higher than the IC$_{50}$ values except with resistant cells treated with parent drugs. For resistant cells treated with parent drugs, the dose was near or below the IC$_{50}$ values. Cytoplasmic drug with a punctate pattern, usually near the nucleus, appeared with all of the cell/drug combinations. The appearance of drug in the nucleus correlated with IC$_{50}$ values. The higher the percentage of drug that appeared in the nucleus, the more toxic the drug.

Table 5 shows qualitative interpretation of confocal micrographs of doxorubicin-sensitive MCF-7 and doxorubicin-resistant MCF-7/ADR cells treated with 5 micro equiv/L of doxorubicin, the dimeric formaldehyde conjugate of doxorubicin, daunorubicin, the dimeric formaldehyde conjugate of daunorubicin, epidoxorubicin, and the dimeric formaldehyde conjugate of epidoxorubicin, as a function of treatment time and recovery time.

The above data and discussion illustrate the utility of the compounds of this invention. The preparation of dimeric drug aldehyde conjugates of this invention can yield conjugates with two or more of the same drug cores; alternatively, they can comprise different drug cores and/or different amino alcohol functionality containing components, such as different amino glycosides. See Formulas III–VI. Mixed formaldehyde conjugates combine the properties of various drugs. For example, a mixed formaldehyde conjugate comprising one molecule of doxorubicin and one molecule of epidoxorubicin, has the advantages of both the dimeric formaldehyde conjugate of doxorubicin (high cytotoxicity) and the dimeric formaldehyde conjugate of epidoxorubicin (high stability to hydrolysis). See Scheme IX.

SCHEME IX

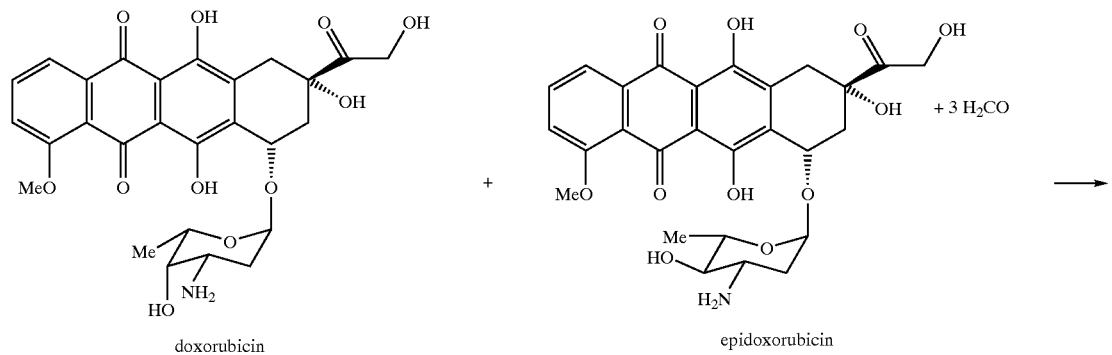

-continued

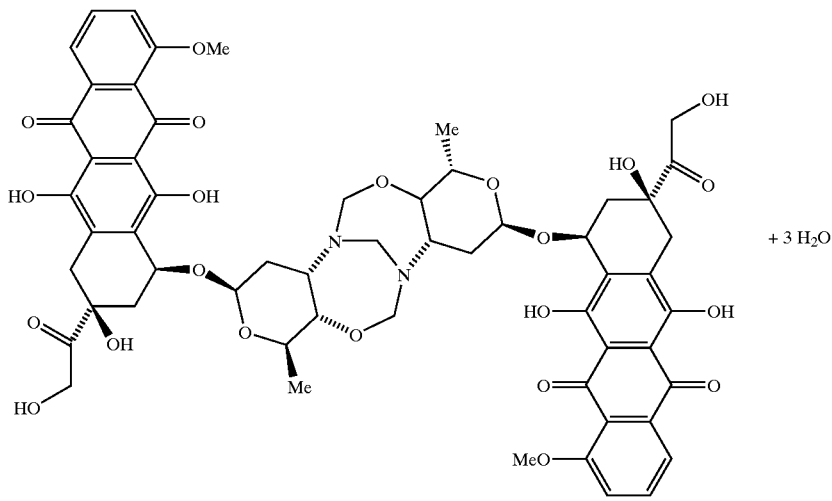

+ 3 H₂O

Anthracycline aldehyde conjugates can be prepared by reaction of an aldehyde with anthracyclines which bear an unsubstituted, free amino alcohol group. Anthracycline formaldehyde conjugates can be prepared by reaction of formaldehyde with anthracyclines which bear an unsubstituted, free amino alcohol group (—NH$_2$), preferably on the sugar at position-7, e.g., the 3'-amino group. Alternatively, a drug which has a functionalized amino group, which can be biologically transformed into an unsubstituted (free) amino group, can be reacted with formaldehyde to form the formaldehyde conjugates of this invention. For example, the dimethyl amino group of menogaril can be oxidatively demethylated, yielding a drug with a free amino group.

Other anthracycline formaldehyde conjugates can be formed by reaction of formaldehyde and various anthracyclines. For example, in the daunorubicin family, Idarubicin (4-demethoxydaunorubicin) can be reacted with formaldehyde. In the aclacinomycin family N-demethylated or N,N-didemethylated aclacinomycin A, and in the nogalamycin family N-demethylated or N,N-didemethylated nogalamycin can be reated with formaldehyde to form formaldehyde conjugates. Oxidative demethylation of aclacinomycin A and nogalamycin yields hydroxylmethylene compounds as intermediates.

As has been noted above and is discussed further below, after reaction of an anthracycline, e.g., daunorubicin or doxorubicin, with formaldehyde, the product dimeric formaldehyde conjugate can be treated by first hydrolyzing it to the mono-oxazolidine and then protecting the amino group of the oxazolidine ring, yielding a pro-drug The term "pro-drug" as used herein refers to a compound which is biologically, i.e., in vivo, transformed to an active form of the drug. To prepare the anthracycline formaldehyde conjugates a free amino group on the anthracycline is needed; however, after the product oxazolidine compound is formed, then its amino group in the oxazolidine ring can be functionalized and/or protected.

This invention provides pro-drugs which are more stable to hydrolysis than are the dimeric formaldehyde conjugate of daunorubicin and the dimeric formaldehyde conjugate of doxorubicin and other anthracycline formaldehyde conjugates and which can be biologically activated, e.g., via enzymatic hydrolysis, to an active form of the drug, an anthracycline formaldehyde conjugate. Pro-drugs can be prepared by adding functional groups and/or protecting groups to the amino group of the oxazolidine ring. Useful functional groups include, but are not limited to, acyl groups, alkoxyformyl, alkenyl, alkylaryl, aralkyl, nitrites, ureas and alkyl groups. Functional groups are chosen so that the amino group is protected and the rate of hydrolysis of the oxazolidine is decreased. The functional group added to protect the amino group does not need to be removed in vivo, unless it is conjugated with the nitrogen in an electron withdrawing manner. In this latter case, the functional group needs to be removable in vivo so that the oxazolidine rings opens up to bind to DNA. Methods and materials for protecting the amino group by adding a functional group can be determined by routine choice by those of ordinary skill in the art. The rate of transformation of the pro-drug into the active form of the drug can be determined by the type of functional group added to protect the amino group, as is understood by those of ordinary skill in the art.

As shown in Scheme X, reaction of the dimeric formaldehyde conjugate of daunorubicin with acetic anhydride or ethyl chloroformate yielded the mono-oxazolidine conjugates N-acetyl-3'-N,4'-O-methylenedaunorubicin or N-(ethoxyformyl)-3'-N,4'-O-methylenedaunorubicin, respectively. The reactions are proposed to occur via initial hydrolysis of the dimeric formaldehyde conjugate of daunorubicin to 3'-N,4'-O-methylenedaunorubicin followed by acylation or ethoxyformylation of the amine function. The acetylated and alkoxyformylated oxazolidines are significantly more stable with respect to hydrolysis to daunorubicin than is the dimeric formaldehyde conjugate of daunorubicin. The resulting amide and carbamate functional groups are believed to be susceptible to hydrolysis in vivo to release the active mono-oxazolidine.

SCHEME X

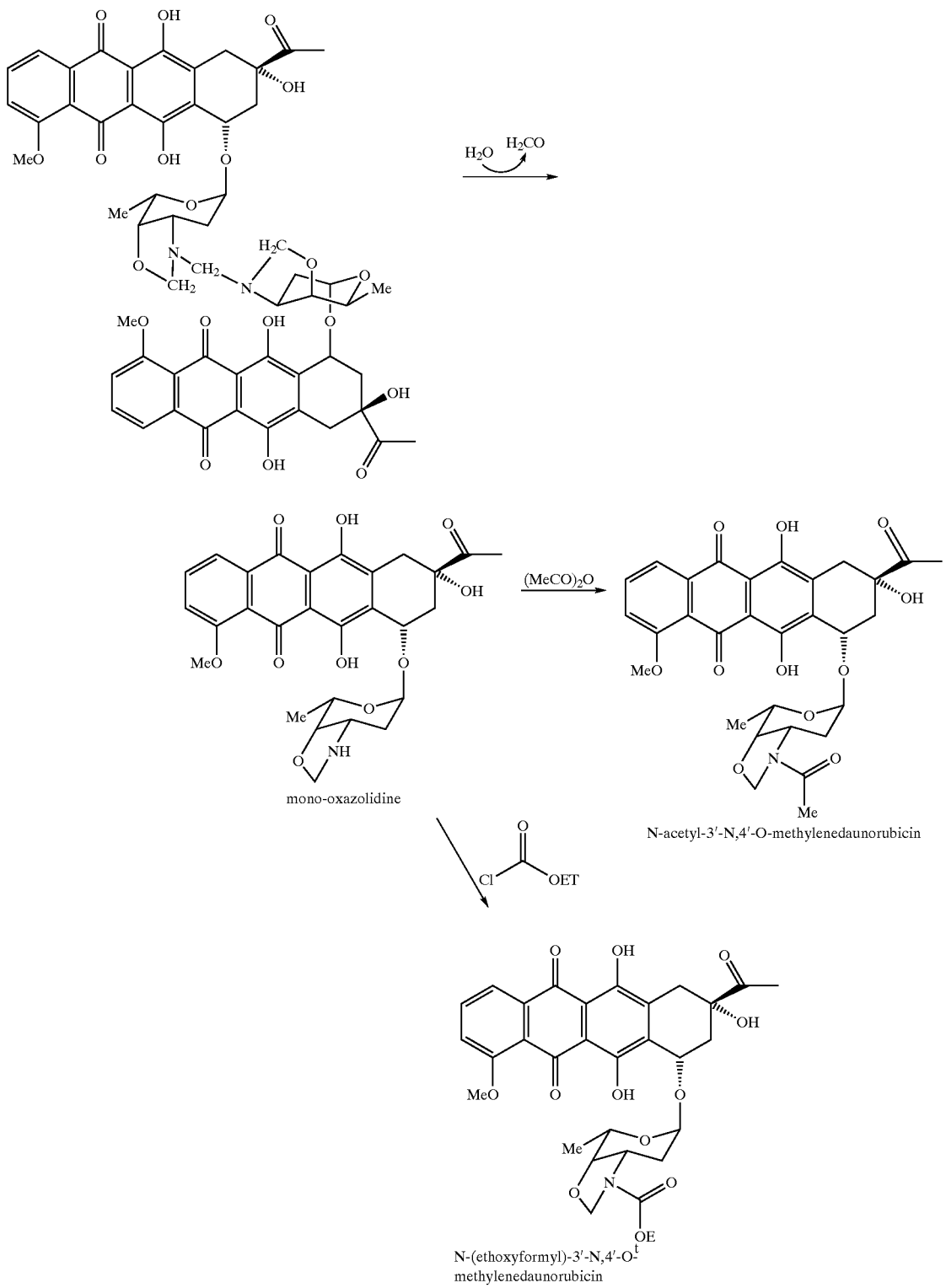

mono-oxazolidine

N-acetyl-3'-N,4'-O-methylenedaunorubicin

N-(ethoxyformyl)-3'-N,4'-O-methylenedaunorubicin

As is known to those in the art, amino groups may be protected using any conventional amino protecting group, for example, as described in "Protective Groups in Organic Chemistry," Ed. J. F. W. McOmnic (Plenum Press, 1973) or "Protective Groups in Organic Synthesis," 2nd edition, by Theodora W. Greene (John Wiley and Sons, 1991). Examples of suitable amino protecting groups include groups selected from alkyl (e.g., methyl, t-butyl or methoxymethyl), aralkyl (e.g., benzyl diphenylmethyl or triphenylmethyl), heterocyclic groups such as tetrahydropyranyl, acyl, (e.g., acetyl or benzoyl) and silyl groups such as trialkylsilyl (e.g., t-butyldimethylsiyl). The amino protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may be similarly removed by solvolysis, e.g., by hydrolysis under acidic conditions. Aralkyl groups such as benzyl may be cleaved, for example, by treatment with $BF_3$/etherate and acetic anhydride followed by removal of acetate groups.

As shown in Scheme XI, the functional group can be chosen so that it confers certain properties to the compound, e.g., lipophilicity. For example, a carbamate with a t-butyl group or a hydrocarbon chain (represented as R* in Scheme XII) has increased lipophilicity, which may be preferable if the compound is to be incorporated into a liposome for drug delivery.

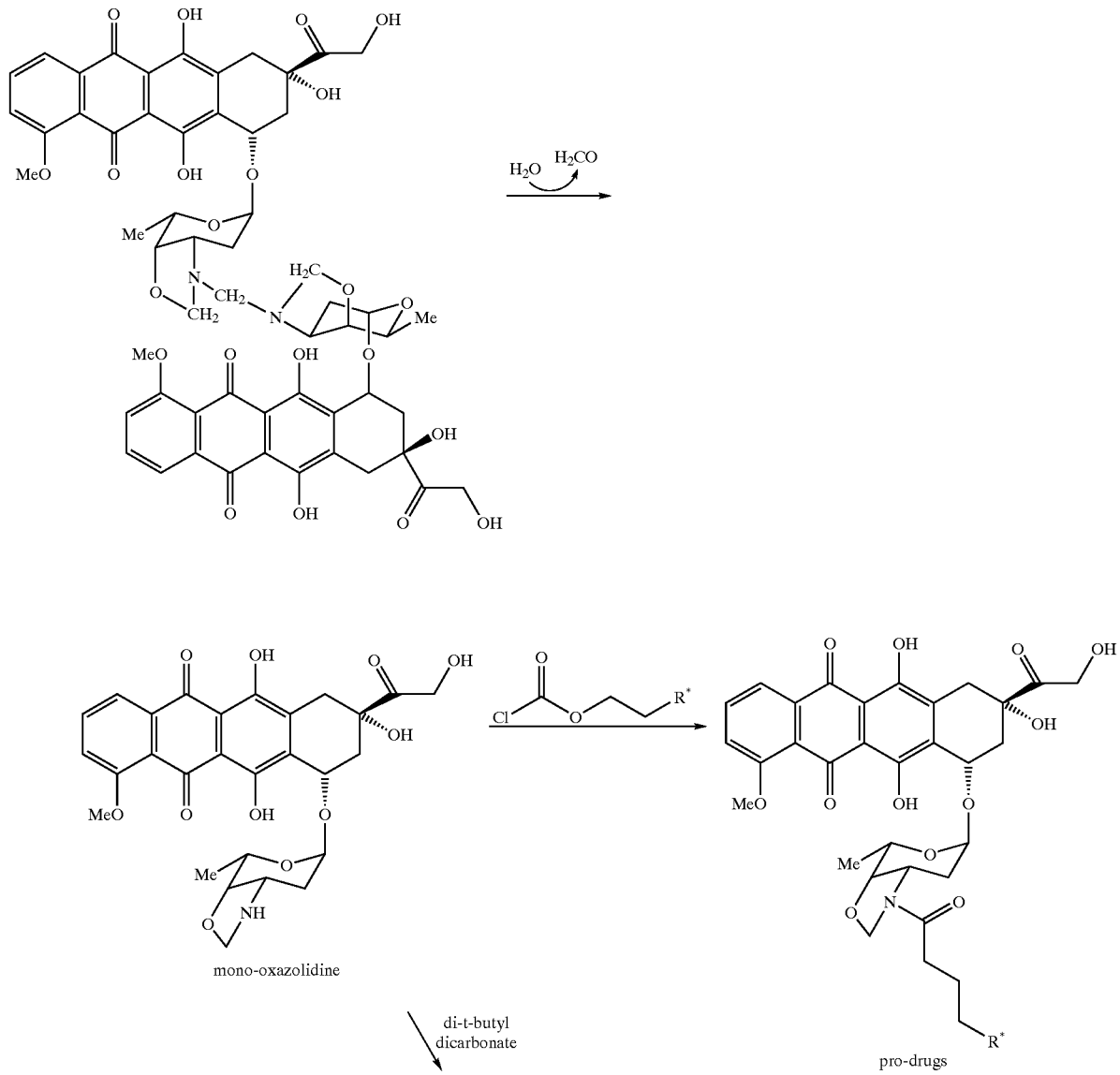

-continued

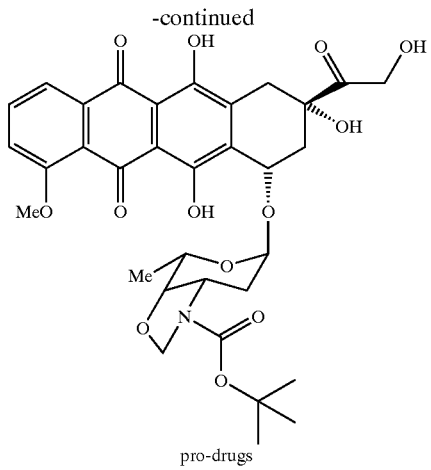

pro-drugs

The anthracycline formaldehyde conjugates of this invention can be stabilized for clinical use by incorporating them into liposomes. Doxorubicin in a stealth liposome is marketed by Sequus Pharmaceuticals, Menlo Park, Calif., as "DOXIL" (Gabizon, A., et al. (1994) Cancer Res. 54, 987–992; Lasic, D. D. & Papahadjopoulos, D. (1995) Science, 1275–1276). Daunorubicin in a conventional liposome is marketed by NeXstar Pharmaceuticals, Boulder, Colo. as "DAUNOXOME" (Guaglianone, P. et al. Investigational New Drugs 12, 103–110). Both products seem to minimize some of the side effects of chemotherapy (including cardiotoxicity) and seem to target tumor cells. A current hypothesis for targeting of tumor cells by "DAUNOXOME" relates to the size of the liposome which causes it to locate at leaky vasculature of developing micrometastases.

"DOXIL" and "DAUNOXOME" have recently been approved by the FDA for the delivery of doxorubicin and daunorubicin, respectively, to tumor cells. These liposomal formulations use a pH gradient to actively load the drug into the liposome. Because the dimeric formaldehyde conjugate of daunorubicin and the dimeric formaldehyde conjugate of doxorubicin are not very basic, they cannot be loaded using an active pH gradient. The liposome is still an attractive drug delivery system because the dimeric formaldehyde conjugate of daunorubicin and the dimeric formaldehyde conjugate of doxorubicin are stable in organic solvents and are stable in the bilayer of a liposome. They are more hydrophobic than daunorubicin and doxorubicin, and consequently dissolve better in the bilayer. Loading of drug aldehyde conjugates is lower and the drugs diffuse from the liposome more readily. A lower drug load is acceptable because the dimeric formaldehyde conjugate of doxorubicin is 150-fold more toxic to MCF-7 cells than is doxorubicin and the dimeric formaldehyde conjugate of daunorubicin is 7-fold more toxic than is daunorubicin. An experiment with liposomes identical to those used in the manufacture of "DAUNOXOME" and the dimeric formaldehyde conjugate of daunorubicin (formed in situ from daunorubicin and formaldehyde) produced liposomes, which were separated from daunorubicin and non-liposomal the dimeric formaldehyde conjugate of daunorubicin by ion exchange column chromatography. Approximately 80% of the daunorubicin was trapped in the liposome as the dimeric formaldehyde conjugate of daunorubicin. The loading was determined by measuring the optical density of the non-liposomal fraction and was found to be approximately 350 molecules of the dimeric formaldehyde conjugate of daunorubicin per, liposome. This load contrasts with the 10,000 molecules of drug per liposome in DOXIL and DaunoXome, which is only 14 times lower.

Liposomal dimeric formaldehyde conjugate of daunorubicin is stabilized for storage indefinitely by lyophilization in the presence of sucrose, which helps maintain the integrity of the liposomes. Lyophilized liposomes can be reconstituted with phosphate buffered saline immediately before use.

The stability of liposomal dimeric formaldehyde conjugate of daunorubicin was established in three different media: pH 7.4 phosphate buffer, pH 7.4 phosphate buffer containing 9% sucrose as a liposomal stabilizer, and fetal bovine serum. Hydrolysis to daunorubicin in phosphate buffer and in phosphate buffer containing sucrose was measured at 25° C. and in serum, at 37° C. The results show biexponential decay with the major portion of the the dimeric formaldehyde conjugate of daunorubicin (70 to 85%) undergoing more rapid hydrolysis to daunorubicin. The half-life for the faster decay is approximately a factor of three longer than for decay of free the dimeric formaldehyde conjugate of daunorubicin, with the half-life in serum at 37° C. approximately 15 min. The slower decay occurs with a half-life of hours and is most apparent for hydrolysis in serum at 37° C. where it accounts for 30% of the dimeric formaldehyde conjugate of daunorubicin hydrolysis.

A sample of the liposomal dimeric formaldehyde conjugate of daunorubicin upon collection at −78° C. in phosphate buffer containing sucrose followed by lyophilization was stable for at least 3 months upon storage at −20° C. This is a preferred method for preparation of liposomal drug for long term storage. The liposomal drug can then be reconstituted by addition of distilled-deionized water just prior to injection.

Although any 1,2-dihetero-subtstituted anti-cancer drug can be reacted with aldehydes to form the drug aldehyde conjugates of this invention, there are many considerations as to which 1,2-dihetero-substituted anti-cancer drugs are preferable. Anthracyclines, in general, are preferred 1,2-dihetero-substituted anti-cancer drugs. Within the class of anthracyclines, doxorubicin, daunorubicin and epirubicin are preferred. Anthracyclines which are redox-compromised may be preferable.

As discussed above, the reductive activation of anthracyclines leads to the production of reactive oxygen species, superoxide radical anion, hydrogen peroxide and hydroxyl radical, via redox-cycling. Superoxide radical anion and hydrogen peroxide oxidize cellular constituents, possibly spermine and cell membrane lipids, to aldehydes, e.g. formaldehyde. The resulting aldehyde reacts with the anthracycline to form anthracycline aldehyde conjugates. However, in addition to oxidation of cellular constituents to aldehydes, these reactive oxygen species created by redox-cycling are believed to cause undesirable side-effects. These side-effects include lipid peroxidation and cardiotoxicity. Thus, it may be preferable to employ anthracycline aldehyde conjugates prepared from redox-compromised anthracyclines in the treatment of cancer. The term redox-compromised anthracyclines as used herein refer to anthracyclines which are harder to reduce (have a more negative reduction potential) and/or are anthracyclines which in reduced form are harder to reoxidize, and therefore do not redox cycle as much as non-redox-compromised anthracyclines, e.g. epidoxorubicin, doxorubicin and daunorubicin.

An example of a redox-compromised anthracycline is 5-Iminodaunorubicin, wherein the oxygen bound to position-5 of the C ring is replaced with an NH (Lown, W. et al. (1982) Biochem. Pharmac. 31:575–581). 5-Iminodaunorubicin is more difficult to reduce, and reduced 5-iminodaunorubicin is much more difficult to reoxidize (Lown, W et al. (1979) Biochem. Pharmac., pp. 2563–2568; Pollakis, G. et al. (1983) FEBS Letters 155(2):267–282; Davies, J. et al. (1983) FEBS Letters 153(1):227–230; Bird, D. et al. (1987) J. Am. Chem. Soc. 109: (13):4046–4053). 5-Iminodaunorubicin leads to virtually no redox-cycling and no production of reactive oxygen species. Thus, there is decreased lipid peroxidation. This analog is much less cardiotoxic and yet retains about the same anti-cancer effectiveness (Johnston, J. et al. (1983) Biochem. Pharmac. 32(14):2255–2258). 5-Iminodoxorubicin and 5-deoxydaunorubicin are other redox-compromised anthracyclines (Acton, E. and Tong, G. (1981) J. Med. Chem. 24(6):669–673; Schweitzer, B. and Koch, T. (1993) J. Am. Chem. Soc. 115:5440–5446).

Redox-compromised anthracycline aldehyde conjugates offer increased cytotoxicity to cancer cells while conferring fewer undesirable side-effects. Such conjugates are prepared by reaction of an aldehyde, e.g. formaldehyde, with a redox-compromised anthracycline. For example, 5-iminodaunorubicin is reacted with formaldehyde as described above in the discussion of the preparation of the dimeric formaldehyde conjugate of daunorubicin and the dimeric formaldehyde conjugate of doxorubicin.

As discussed above, we believe that anthracycline aldehyde conjugates also exert their effects through alkylation of protein, in particular protein kinase C. We believe that anthracycline aldehyde conjugates affect the activity of various proteins. Protein kinase C is a key protein in signal transduction and cell regulation. The doxorubicin-iron(III) complex was shown by Hannun and co-workers to be a potent inhibitor of protein kinase C, and the inhibition was reversible (Hannun, Y. A. et al. (1989) J. Biol. Chem. 264:9960–6). Acetylation of the amino group of doxorubicin did not preclude formation of a ferric complex but resulted in total loss of inhibitory activity. The reaction conditions of these studies included Tris buffer and a thiol stabilizing agent (Hannun, Y. A. et al. (1985) J. Biol. Chem. 18:10039). These are ideal conditions for doxorubicin catalyzed production of formaldehyde. We believe that the actual inhibitor of protein kinase C in the experiments of Hannun and co-workers was the mono-oxazolidine, which also results from partial hydrolysis of the dimeric formaldehyde conjugate of doxorubicin, and that the mono-oxazolidine created a covalent linkage to a nucleophilic amino acid residue, possibly a cysteine residue, of protein kinase C This is consistent with the loss of inhibition upon acetylation of the amino group of doxorubicin because acetylation would block formation of a Schiff base and/or oxazolidine. It is also consistent with reversible inhibition because of the instability of the, formaldehyde covalent linkage.

As discussed above, the therapeutic activity of the anthracycline formaldehyde conjugate compounds of this invention is believed to result from the formation of drug-DNA conjugates, as well as covalent adducts with proteins, e.g. protein kinase C, and possibly covalent adducts with lipids, e.g., phosphatidylethanolamine. The term covalent adduct as used herein refers to a product formed by reaction of two or more molecules which become covalently bound to one another. A covalent adduct formed by reaction of nucleic acid with an anti-cancer drug is similar to a virtual cross-link in that they both contain a covalent bond between the drug and one strand of nucleic acid; a covalent adduct is distinguished from a virtual cross-link in that the former is not stabilized by hydrogen bonding to the other strand of the nucleic acid.

This invention provides pharmaceutical and/or therapeutic compositions which are those possessing anti-cancer/anti-tumor activity and which are useful in the treatment of malignant diseases.

This invention further provides pharmaceutical compositions comprising a 1.2-dihetero-substituted anti-cancer drug aldehyde conjugate, and preferably an anthracycline formaldehyde conjugate, in an amount effective for inhibiting growth of malignant cells, and optionally a pharmaceutically acceptable carrier. Preferred aldehyde conjugate compounds and compositions of this invention are those which are effective for treatment of tumors in mammals, and most preferred are those effective for treatment of tumors in humans. A variety of dosage forms can be employed with the compounds and compositions of this invention.

For injectable use, the pharmaceutical composition forms include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol, chremophor-el, tween 80, glycerol, dimethyl sulfoxide (DMSO), propylene glycol, and liquid polyethylene glycol, and the like suitable mixtures thereof, and vegetable oils. The proper fluidity can be maintained for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the active ingredient or ingredients in the required amount in the appropriate solvent with various of the other ingredients enumerated above, as required followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

Pharmaceutical compositions suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well-known in the art. Oral liquid preparations may be in the form of, for example, aqueous or oily suspensions, solutions, emulsions, syrups, or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

As used herein, the expression "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the conjugate compounds of this invention, its use in the present compositions is contemplated. Supplementary active ingredients can be incorporated into the inventive compositions.

It is especially advantageous to formulate compositions in dosage unit form for case of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification.

The dosage of the principal active ingredient (the conjugate compounds of this invention) for the treatment of the indicated conditions depends upon the age, weight and condition of the subject being treated the particular condition and its severity; the particular form of the active ingredient, the potency of the active ingredient, and the route of administration. A daily dose of from about 0.001 to about 100 mg/kg of body weight given singly or in divided doses of up to 5 times a day or by continuous infusion embraces the effective range for the treatment of most conditions for which the novel compounds are effective and substantially non-toxic. For a 75 kg subject, this translates into between about 0.075 and about 7500 mg/day. If the dosage is divided, for example, into three individual dosages, these will range from about 0.25 to about 2500 mg of the active ingredient. The preferred range is from about 0.1 to about 50 mg/kg of body weight/day with about 0.2 to about 30 mg/kg of body weight/day being more preferred.

The principal active ingredient (the conjugate compounds of this invention) is compounded for convenient and effective administration in effective amounts with a suitable pharmaceutically acceptable carrier in dosage unit form as hereinbefore disclosed. A unit dosage form can, for example, contain the principal active ingredient in amounts ranging from about 0.1 to about 1000 mg, with from about 1.0 to about 500 mg being preferred. Expressed in proportions, the active ingredient is generally present in from about 0.1 to about 500 mg/ml of carrier. In the case of compositions containing supplementary active ingredients, the dosages are determined by reference to the usual dose and manner of administration of the said ingredients.

Anti-cancer treatment comprises the administration of any of the compounds of this invention in an acceptable pharmaceutical formulation/composition at an effective therapeutic dosage. It is understood that chemotherapy can require the use of any of the compounds of this invention bound to an agent which facilitates targeting the compound to the tumor cells. The agent may be chosen from, for example, monoclonal or polyclonal antibodies, nucleic acids, peptides, proteins and liposomes. The compounds of this invention could also be administered as monomeric, dimeric or oligomeric metal chelate complexes with, for example, iron, magnesium or calcium. An effective therapeutic dosage is one which leads to improvement in a patient's symptoms, e.g., slower increase in growth of tumor; decrease in size of tumor; less pain, malaise or fever; increased survival time; improved quality of life; and any other conditions which a physician would typically consider beneficial in an anti-cancer drug.

The compounds of the invention exhibit antitumor or anticancer activity, most notably, antitumor or anticancer activity with human breast cancer, leukemia, colon cancer, prostate cancer, lung cancer, renal cancer, ovarian cancer, CNS cancer and melanoma. Any of these malignancies may be metastatic or non-metastatic. This list of conditions is however not exclusive, and it is believed that the compounds of the invention will exhibit activity against other tumors and cancers, such as for example pancreatic cancer and bladder cancer.

The compounds of the invention may also be used for ex vivo treatment of patients before bone marrow transplant or other sorts of treatments to get rid of cancerous cells outside of the body.

Certain of the above-described intermediates which result from hydrolysis of the conjugate compounds of this invention are also of interest from a pharmacological standpoint. For example, intermediate B in the hydrolysis of the dimeric formaldehyde conjugate of epidoxorubicin, is of interest. The intermediates are preferably administered as a pharmaceutical composition for the treatment of the conditions listed above, and may be administered in the dosages noted above. Moreover, the intermediates may be administered as pharmaceutically acceptable salts or as metal chelate complexes where appropriate, and may be administered as a mixture with other of the intermediate compounds, and/or with the conjugate compounds of this invention, and/or with one or more of the therapeutic agents or agents targeting cancer or tumor cells.

This invention further provides methods for making the anthracycline formaldehyde conjugate compounds as described herein. There are two general methods provided for making these compounds. The starting materials, solvents, buffers, reagents, reaction conditions, reaction procedures and purification techiniques can be modified without undue experiementation by one of ordinary skill in the art, and all such variations fall within the scope of this invention.

In one method, a 1,2-dihetero-substituted anti-cancer drug is added to an aldehyde (preferably an excess of aldehyde) in the presence of an aqueous volatile buffer. Such buffers are known to those or ordinary skill in the art and include but are not limited to triethylammonium acetate, ammonium acetate and ammonium carbonate. The pH can range from about 3 to about 10, more preferably from about 4 to about 8, and most preferably is about 6. The reaction occurs at atmospheric pressure and room temperature, although varying the pressure and temperature may be preferable to improve yield, decrease unwanted by-products, etc. in some cases. After reaction, the prodict is extracted into an organic solvent, e.g. methylene chloride or chloroform, and the solvent is evaporated.

In a second method, a 1,2-dihetero-substituted anti-cancer drug is added to an aldehyde in the presence of organic solvent containing either a volatile buffer or an inorganic buffer. Inorganic buffers are known to those or ordinary skill in the art and include but are not limited to phosphate buffers. The reaction mixture is stirred. The reaction occurs at atmospheric pressure and room temperature, although varying the pressure and temperature may be preferable in some cases. After extraction of the aqueous phase, the organic layer is collected, and the aqueous layer is extracted a second time. The organic layers contain the desired drug aldehyde conjugate and are pooled, dried, and evaporated.

This invention further provides methods for treating cancer comprising administering the conjugates and/or compositions comprising such conjugates in a therapeutically effective amount to animals, preferably mammals, and most preferably humans.

Numerous embodiments besides those mentioned herein will be readily apparent to those skilled in the art and fall within the range and- scope of this invention. The following examples illustrate the invention, but are in-no way intended to limit the invention.

All references cited in this specification are incorporated in their entirety by reference herein.

EXAMPLES

General remarks for Experiments with the dimeric formaldehyde conjugate of doxorubicin and the dimeric formaldehyde conjugate of daunorubicin. UV-vis spectra were recorded with a Hewlett-Packard 8452A diode array spectrometer and $^1$H NMR spectra, with a Bruker Model Am-400 spectrometer. Mass spectra of the dimeric formaldehyde conjugate of daunorubicin and the dimeric formaldehyde conjugate of doxorubicin were obtained with a Hewlett-Packard 5989B single quadrupole electrospray mass spectrometer, samples were introduced by direct infusion of chloroform/methanol solutions. Mass spectra of drug-DNA virtual cross-links were obtained with an API-III triple quadrupole mass spectrometer (Sciex) equipped with a nebulization-assisted electrospray (ES) ion source and a high-pressure collision- cell; samples were introduced by direct infusion of water/methanol (75/25, v/v) solutions. Daunorubicin and doxorubicin as their hydrochloride salts or as clinical samples were received as gifts from Nexstar Pharmaceuticals, Inc, San Dimas, Calif. and Pharmacia-Upjohn-Farmitalia, Milan, Italy. Formaldehyde was obtained from Mallinckrodt as a 37% by weight solution in water containing 10–15% methanol. Water was distilled and purified with a Millipore Q-UF Plus purification system to 18 Mohm-cm; water so purified is sometimes referred to as "Millipore water". Phosphate buffer, pH 7.4, was 77.4 mM $Na_2HPO_4$ and 22.6 mM $NaH_2PO_4$. Triethylamine for preparation of triethylammonium acetate buffer was 99+% from Aldrich, and tris(hydroxymethyl)aminomethane (Tris) was from Boehringer Mannheim. HPLC analyses were performed with a Hewlett-Packard 1090 liquid chromatograph equipped with a diode array. UV-vis detector and workstation; chromatographies were performed with a Hewlett-Packard 5-μm $C_{18}$ microbore column, 2.1 mm i.d. ×100 mm, eluting at 0.5 mL/min with gradients of pH 6 triethylammonium acetate ($Et_3NHOAc$) (0.02 M)/acetic acid. (AcOH) buffer and acetonitrile and detecting at 260 and 480 nm.

Example 1

Synthesis of the Dimeric Formaldehyde Conjugate of Daunorubicin: Amorphous Dimeric Formaldehyde Conjugate of Daunorubicin.

A solution containing 1 mM daunorubicin and 50 mM formaldehyde in 100 mL of pH 6 triethylammonium acetate (20 mM)/acetic acid buffer was allowed to react in the dark at 25° C. for 21 h. The buffer was then removed by high-vacuum rotary evaporation at 0.1 Torr for 5 h. The dry product was dissolved in chloroform and placed in a 15 mL centrifuge tube. The solvent was removed by rotary evaporation, and the dry sample was washed with 3×10 mL of water by centrifugation at 1550 rpm and removal of the water with a pipette. After the final wash, the sample was dried under vacuum at 0.02 Torr for 10 h to yield an amorphous red solid. A positive ion ESI mass spectrum with the sample in chloroform/methanol (5/1, v/v) was obtained. A $^1$H NMR spectrum in deuteriochloroform solvent established that the product was pure and together with the MS spectrum, indicated that it had the structure, bis-(3'-N-(3'-N,4'-O-methylenedaunorubicinyl))methane (the dimeric formaldehyde conjugate of daunorubicin). The yield of the dimeric formaldehyde conjugate of daunorubicin was established by visible absorption at 480 nm because the sample could not be accurately weighed. A solution was prepared by dissolving the entire product in 5 mL of chloroform followed by a 400× serial dilution. The absorbance at 480 nm established a, yield of 49 μmol (67%), using the molar extinction coefficient 9900 $M^{-1}$ $cm^{-1}$ for the daunorubicin chromophore. A similar experiment using 10 equiv of formaldehyde generated the same product in 70% yield. In this case the reaction time was 67 h.

Example 2

Crystalline the Dimeric Formaldehyde Conjugate of Daunorubicin.

To a solution of 40 mg (70.9 μmol) of daunorubicin hydrochloride in 40 mL of pH 6 triethylammonium acetate buffer was added 80 mL of chloroform and 0.8 mL of aqueous methanolic formaldehyde (37% formaldehyde). The solution was stirred vigorously until extraction of the aqueous phase was complete (about 30 min). The organic layer was collected and the aqueous layer was extracted a second time with 80 mL of chloroform in a similar manner. The organic layers were pooled, dried over sodium sulfate, and the solvent removed by rotary evaporation yielding crude the dimeric formaldehyde conjugate of daunorubicin as a red film. The crude product was redissolved in 0.8 mL of chloroform. The solution volume was brought to 16 mL by addition of ethyl acetate and the solution mixed thoroughly. The solution was dispensed in 3 mL aliquots into five 5 mL vials and allowed to stand undisturbed, stoppered, and in the dark for 3 days. The resulting crystals grew as red needles on the glass. The crystals were washed with n-hexane, collected, and dried under vacuum (0.1 Torr) to yield 20 mg (51%) of the dimeric formaldehyde conjugate of daunorubicin Anal. ($C_{57}H_{58}N_2O_{18}$)C, H, N. The crystalline material showed the same $^1$H NMR spectral properties as the amorphous material prepared as in Example 1. $^{13}$C NMR and positive ion ESI mass spectrum with the sample in chloroform/methanol (5/1, v/v) supported the structure in Scheme III for the dimeric formaldehyde conjugate of daunorubicin. A significant difference between the amorphous and crystalline materials was the rate at which each dissolved in dimethylsulfoxide; the amorphous material dissolved instantly to at, least 20 mg/mL, whereas the crystalline material dissolved very slowly.

Example 3
Synthesis of the Dimeric Formaldehyde Conjugate of Doxorubicin: Amorphous Dimeric Formaldehyde Conjugate of Doxorubicin.

A clinical sample containing doxorubicin hydrochloride and lactose was used as the starting material. Most of the lactose was removed by extraction with chloroform. A doxorubicin/lactose mixture containing 40 mg of doxorubicin was dissolved in 75 mL of pH 8, 0.1 M potassium chloride, 40 mM tris(hydroxymethyl)aminomethane (Tris), 100 mM ethylenediaminetetraacetic acid (EDTA) buffer. To this was added 100 mL of chloroform, and the mixture was stirred vigorously for 30 min. The chloroform layer was then removed and a second extraction using 50 mL of chloroform performed. The chloroform extracts were combined and the chloroform removed by rotary evaporation yielding doxorubicin as the free base A solution of 1 mM doxorubicin and 50 mM formaldehyde in 68 mL of pH 6, tyiethylammonium acetate (20 mM)/acetic acid buffer was allowed to react in the dark at 25° C. for 15 h. The buffer was then removed by high-vacuum (0.1 Torr) rotary evaporation for 5 h. The product was dissolved in chloroform and placed in a 15 mL centrifuge tube. The solvent was removed by rotary evaporation and the dry sample was washed with 3×10 mL portions of water by centrifugation at 1550 rpm. After the final wash, the sample was again dried under vacuum at 0.02 Torr for 15 h. The $^1$H NMR spectrum in deuteriochloroform solvent established that the product was pure and together with the MS spectrum of crystalline material, indicated that it had the structure, bis-(3'-N-(3'-N,4'-O-methylenedoxorubicinyl))methane. (the dimeric formaldehyde conjugate of doxorubicin) (Scheme III). The isolated yield was determined to be 70% by visible absorption at 480 nm of a chloroform solution as described above for the dimeric formaldehyde conjugate of daunorubicin.

Example 4
Crystalline Dimeric Formaldehyde Conjugate of Doxorubicin.

Crystalline dimeric formaldehyde conjugate of doxorubicin was prepared in a similar manner as was crystalline dimeric formaldehyde conjugate of daunorubicin except for the crystallization step. For a procedure starting with 40 mg, the crude product was dissolved in 1.3 mL of chloroform diluted with 27 mL of 3:1 ethyl acetate:hexane. The resulting solution was dispensed in 3 mL aliquots into nine 5 mL vials and allowed to stand undisturbed and stoppered in the dark for 3 days. The resulting crystals grew as red hexagonal tubes on the glass. The crystals were washed with ethyl acetate, collected, and dried under vacuum (0.1 Torr) to yield 14.5 mg (37%) of pure dimeric formaldehyde conjugate of doxorubicin. Anal. ($C_{57}H_{58}N_2O_{22}$)C, H, N. The crystalline material showed the same $^1$H NMR spectral properties as the amorphous material. The positive ion ESI mass spectrum of a sample in chloroform/methanol supported the structure in Scheme III for the dimeric formaldehyde conjugate of doxorubicin.

Example 5
Dilution of a Deuteriochloroform Solution of the Dimeric Formaldehyde Conjugate of Daunorubicin.

A sample of the dimeric formaldehyde conjugate of daunorubicin was dissolved in 500 μL of deuteriochloroform and the solution was analyzed by $^1$H NMR spectroscopy. The sample was then diluted to volumes of 750 μL, 1000 μL, 1250 μL, and 1500 μL with deuteriochloroform. At each new volume the $^1$H NMR spectrum was obtained and integrated using the chloroform signal as an internal standard. The spectra showed conversion of the dimeric formaldehyde conjugate of daunorubicin to an equilibrium mixture of the dimeric formaldehyde conjugate of daunorubicin with 3'-N, 4'-O-methylenedaunorubicin (mono-oxazolidine). The composition of the solutions at each dilution was tabulated in terms of the areas for the phenolic OH signals relative to the area for the chloroform signal.

Example 6
The Dimeric Formaldehyde Conjugate of Daunorubicin Stability in DMSO.

Crystalline dimeric formaldehyde conjugate of daunorubicin (2.8 mg, 2.6 μmol) was dissolved in 500 μL of DMSO-$d_6$ (stored over 3 A molecular sieves) and analyzed by 400 MHz, $^1$H NMR. NMR analysis showed that the dimeric formaldehyde conjugate of daunorubicin was stable in DMSO for at least 14 h. Upon addition of 25 μL of $D_2O$ to the 500 μL DMSO-$d_6$ sample, the dimeric formaldehyde conjugate of daunorubicin reacted over a 24 h period to form an equilibrium mixture consisting of 67% dimeric formaldehyde conjugate of daunorubicin and 32% of an intermediate. Because of the complexity of the spectrum, a structure could not be assigned to the intermediate; however, the intermediate appeared to have an oxazolidine ring. Upon addition of 3 equiv of hydrochloric acid in 130 μL of deuterium oxide, hydrolysis to daunorubicin-HCl was complete. The hydrochloric acid solution was prepared by the addition of 10 μL of concentrated HCl to 990 μL of $D_2O$. The formaldehyde released from the dimeric formaldehyde conjugate of daunorubicin was detected as its hydrate. The final product was identified as daunorubicin by comparison of the NMR spectrum with that of a sample of daunorubicin plus 3 equiv of HCl. Further, the final product was isolated by removal of all volatile components under vacuum (0.1 Torr), and its $^1$H NMR spectrum was identical to that of daunorubicin-HCl.

Example 7

Amorphous dimeric formaldehyde conjugate of daunorubicin, when worked up in methylene chloride, was stable in DMSO for at least 4 days. It hydrolyzed with added $D_2O$ and hydrochloric acid in a manner similar to that of the crystalline material. When worked up in chloroform, amorphous dimeric formaldehyde conjugate of daunorubicin had less stability in DMSO, presumably due to traces of HCl from the chloroform.

Example 8
Reaction of the Dimeric Formaldehyde Conjugate of Daunorubicin with $(GC)_4$.

A solution containing 317 μM $(GC)_4$ and 357 μM of the dimeric formaldehyde conjugate of daunorubicin in 150 μL of pH 7.4 phosphate buffer was allowed to react 41 h in the dark at 25° C. The DNA had completely reacted to form drug-DNA conjugates A, B+C, D, and E in a 2:19:68:11 peak area ratio as indicated by HPLC. The C18 HPLC column was eluted with the following gradient created with Solvent A'=CH$_3$CN, Solvent B'=20 mM aqueous triethylammonium acetate pH 6: Solvent A': Solvent B', 0:100 to 7:93 at 1 min, to 9:91 at 10 min, to 70:30 at 13 min, isocratic until 15 min and to 0:100 at 17 min. The retention times for conjugates A–E were 7.4, 8.3, 8.6, 9.7, 12.3 min. HPLC peaks for conjugates B and C were not resolved and were integrated together. Conjugates A–D were isolated and characterized by UV-vis absorption and negative ion ESMS; the spectral data showed them to be identical to conjugates A–D (called #1–#4 in Fenick, D. J. et al. (1997) *J. Med. Chem.* 40, 2452–2461) from reaction of daunorubicin with (GC)$_4$ and formaldehyde described elsewhere (Fenick, D. J. et al. (1997), J. Med. Chem. 40, 2452–2461). Conjugate E was isolated by preparative reverse phase HPLC as described earlier for conjugates A–D (#1–#4 in Fenick, D. J. et al. (1997) *J. Med. Chem.* 40, 2452–2461). The UV-vis spectrum of conjugate E indicated that it was a drug-DNA conjugates containing 3 molecules of covalently bound, intercalated drug per dsDNA. The negative ion, electrospray mass spectrum confirmed this structural assignment.

Example 9

Drug-DNA Conjugate Formation in the Presence of the Dimeric Formaldehyde Conjugate of Daunorubicin or Daunorubicin Plus Formaldehyde as a Function of Time.

Reaction mixtures containing 33 $\mu$M (GC)$_4$ and 55 $\mu$M of the dimeric formaldehyde conjugate of daunorubicinin pH 7.4 phosphate buffer were monitored periodically by HPLC over a 1 h time period. The reaction mixtures were maintained at 25° C. and contained 2% DMSO to facilitate the solubilization of the dimeric formaldehyde conjugate of daunorubicin. The amount of "virtual" formaldehyde in this reaction was 165 $\mu$M (3×55 $\mu$M). Virtual formaldehyde refers to the amount of formaldehyde contained in the dimeric formaldehyde conjugate of daunorubicin, e.g., each molecule of the dimeric formaldehyde conjugate of daunorubicin contains 3 equivalents of formaldehyde. Similar reaction mixtures containing 33 $\mu$M (GC)$_4$, 110 $\mu$M daunorubicin, and 165 4$\mu$M formaldehyde in pH 7.4 phosphate buffer were prepared and monitored periodically by HPLC as described above. The reaction mixtures were maintained at 25° C. and contained 2% DMSO. The formation of drug-DNA conjugates With respect to time for the daunorubicin and the dimeric formaldehyde conjugate of daunorubicin reactions is compared in FIG. 1.

Example 10

Cell Experiments.

All tissue culture materials were obtained from Gibco Life Technologies (Grand Island, N.Y.) unless otherwise stated. MCF-7 breast cancer cells were obtained from American Type Culture Collection (Rockville, Md.). MCF-7/ADR doxorubicin resistant breast cancer cells (Batist, G. et al. (1986), "Overexpression of a novel anionic glutathione transferase in multi-drug-resistant human breast cancer cells," J. Biol. Chem. 261:15, 544–15, 549) were a gift of Dr. William W. Wells (Michigan State University). Both cell lines were maintained in vitro by serial culture in phenol red-free RPMI Media 1640 supplemented with 10% fetal bovine serum (Gemini Bio-Products, Calbasas, Calif.), L-glutamine (2 mM), HEPES buffer (10 mM), penicillin (100 units/mL), and streptomycin (100 $\mu$g/mL). The MCF-7/ADR cell line media was additionally supplemented with 5 $\mu$M doxorubicin (Nexstar Pharmaceuticals, San Dimas, Calif.). Cells were maintained at 37° C. in a humidified atmosphere of 5% CO$_2$ and 95% air.

Cells were dissociated with trypsin-EDTA, counted, and suspended in growth media to a concentration of 5×10$^3$ cells/mL. Cell suspensions were dispensed in 200 $\mu$L aliquots into 96-well tissue culture plates. Plates were then incubated for 24 h at 37° C. in a humidified atmosphere of 5% CO$_2$ and 95% air. The media was replaced with 180 $\mu$L of growth media prior to addition of the cytotoxic agents.

Cytotoxic agents (daunorubicin, doxorubicin, and the dimeric formaldehyde conjugate of daunorubicin, and the dimeric formaldehyde conjugate of doxorubicin) were dissolved in DMSO at a concentration of 10 mmol equiv./L, sonicated to facilitate solvation, and sterile filtered through a 0.2 $\mu$m nylon syringe filter. Concentrations were then corrected by measuring the solution absorbance at 480 nm ($\epsilon$=11,500/mole anthracycline). The solutions were then serially diluted in DMSO to give a series of 100× working concentration solutions. For each concentration, the 100× solution was diluted 1:10 in serum-free RPMI Media 1640. 20 $\mu$L of the resulting 100× solution was immediately added to the appropriate lane. Additionally, one lane was treated with 20 $\mu$L of 10% DMSO in serum-free RPMI (no drug) and one lane replaced with 200 $\mu$L of 1.5 M Tris buffer (no cells). The cells were incubated at 37° C. for 3 h. The drug solutions were removed and 200 $\mu$L of fresh growth media was added to each well. The cells were then incubated for 6 days at 37° C. in a humidified atmosphere of 5% CO$_2$ and 95% air (approximately 60% confluence for the no drug lane).

The extent of colony formation was determined by use of a crystal violet staining assay (Gilles, R. J. et al. (1986), "Determination of cell number in monolayer cultures," Anal. Biochem. 159:109–113; Reile, H. et al. (1990), "Computerized determination of growth kinetic curves and doubling times from cells in microcultures," Anal. Biochem. 187:262–267). Cells were treated with 200 $\mu$L of 1% glutaraldehyde in Hank's Balanced Salt Solution for 15 min. The cells were then stained with 75 $\mu$L of 0.1% crystal violet in deionized water for 30 min. The plates were then rinsed with deionized water and allowed to soak in a beaker of running deionized water (1L/min) for 15 min. The plates were blotted dry and 200 $\mu$L of 70% ethanol in water was added to each well to solublize the dye. The plates were stored at 4° C. until solubilization was complete (about 4 h). The optical density of each well was measured on an ELISA plate reader at 588 nm. Relative colony sizes were determined by comparison of the drug treated lanes to the control lanes. The results are reported in Table 1.

Control experiments established that the IC$_{50}$ value for formaldehyde was in excess of 200 $\mu$M with MCF-7 and MCF-7/ADR cells. Additional control experiments established that 3 h incubation of cells with 1% DMSO in growth media did not alter the survival of MCF-7 or MCF-7/ADR cells.

Example 11

Cytotoxicity of the Dimeric Formaldehyde Conjugate of Daunorubicin and the Dimeric Formaldehyde Conjugate of Doxorubicin Versus Time of Addition.

Cells were dissociated with trypsin-EDTA, counted, and suspended in growth media to a concentration of 5×10$^3$ cells/mL. Cell suspensions were dispensed in 200 $\mu$L aliquots into 96-well tissue culture plates. Plates were then incubated for 24 h at 37° C. in a humidified atmosphere of 5% CO$_2$ and 95% air. The media was replaced with 180 $\mu$L of growth media prior to addition of the cytotoxic agents. The drug being investigated (the dimeric formaldehyde conjugate of doxorubicin or the dimeric formaldehyde conjugate of daunorubicin) was dissolved in DMSO at a concentration of 0.5 mM (1 mmol equiv/L), sonicated to facilitate solvation, and sterile filtered through a 0.2 μm nylon. syringe filter. Concentrations were then corrected by measuring the solution absorbance at 480 nm ($\epsilon$=11,500/mole anthracycline). The drug solution was diluted 1:100 with DMSO, then 1:10 in serum-free RPMI media 1640. A volume of 20 μL of the resulting 0.5 μM (1 μmol equiv/L) drug solution was immediately added to the t=0 min lane. The remaining lanes were treated at 5 min intervals with 20 μL of the remaining drug solution, which was held at 25° C. between additions. Additionally, one lane was treated with 20 μL/well of serum-free RPMI media containing 10% DMSO (no drug) and one lane replaced with 200 μL/well of 1.5 M Tris buffer (no cells). Each lane was incubated at 37° C. for 3 h. The drug solutions were removed and 200 μL of fresh growth media was added to each well. The cells were then incubated for six days at 37° C. in a humidified atmosphere of 5% $CO_2$ and 95% air. The extent of colony formation was determined by use of a crystal violet staining assay described above and relative colony sizes determined by comparison of the drug treated lanes to the control lanes.

Example 12
Synthesis and Characterization of N-acetyl-3'-N,4'-O-methylenedaunorubicin.

A solution containing 73 μmol equiv of the dimeric formaldehyde conjugate of daunorubicin and 1.46 mmol (20 equiv) of acetic anhydride in 14 mL of methylene chloride was allowed to react 3 h in the dark at 25° C. The solvent was then removed by evaporation with a stream of nitrogen, and the dried product was washed with 3×10 mL of Millipore water. The product was then placed under vacuum (0.1 Torr) for 17 h to remove residual water. The yield was established as 83% based upon the optical density at 480 nm of a standard solution. $^1$H NMR analysis of the product revealed a 46:54 mixture of two different rotamers, A and B, of N-acetyl-3'-N,4'-O-methylenedaunorubicin. This was confirmed by heating the NMR sample to 40° C. and observing the paired signals begin to coalesce. Negative ion, electrospray mass spectrometry in chloroform/methanol (5/1, v/v) supported the structure. The N-acetylated product was similarly synthesized using methanol or chloroform as the solvent.

Example 13
Stability of N-Acetyl-3'-N,4'-O-methylenedaunorubicin in DMSO and DMSO/H$_2$O Solution.

A 1.3 mg sample of N-acetyl-3'-N,4'-O-methylenedaunorubicin was dissolved in 300 mL of DMSO and analyzed over time by HPLC. After 2 h, no degradation had occurred in the DMSO solution. At this time, 300 mL of water was added to the DMSO/N-acetyl monomeric formaldehyde conjugate of daunorubicin solution, establishing a 50:50 DMSO:water mixture (v/v). In this solution, the N-acetyl-3'-N,4'-O-methylenedaunorubicin remained 91% intact (9% degradation to daunorubicin) over a period of 6 days, based upon the HPLC analysis.

Example 14
Synthesis and Characterization of N-(Ethoxyformyl)-3'-N, 4'-O-methylenedaunorubicin.

A chloroform solution containing 8.2 μmoles 4-dimethylamino pyridine (DMAP) and 8.2 μmoles ethyl chloroformate was added to 2.1 μmol of the dimeric formaldehyde conjugate of daunorubicin (total volume: 650 μL). This mixture was allowed to react 3 h in the dark at 25° C. The sample was then extracted with 4×1 mL of Millipore water. The chloroform was then removed by N$_2$ evaporation and subsequently washed with 5×2 mL of Millipore water. After the final wash, the sample was placed under vacuum (1 Torr, 2 h) to remove residual water. NMR analysis of the purified product, together with ESMS analysis, confirmed the product to be N-(ethoxyformyl)-3'-N,4'-O-methylenedaunorubicin. ESMS samples were dissolved in chloroform/methanol (4:1 v:v) and directly infused into the ionization chamber of the mass spectrometer.

General remarks for Experiments with the dimeric formaldehyde conjugate of epidoxorubicin. UV-vis spectra were recorded with a Hewlett-Packard. 8452A diode array spectrometer and $^1$H NMR spectra, with a Bruker Am-400 or Varian Unity Inova 500 spectrometer. Mass spectra of the dimeric formaldehyde conjugate of epidoxorubicin and. drug-DNA virtual cross-links were obtained with an API-III triple quadrupole mass spectrometer (Sciex) equipped with a nebulization-assisted electrospray (ES) ion source and a high-pressure collision cell; samples were introduced by direct infusion of water/methanol (75/25, v/v) solutions unless stated otherwise. Epidoxorubicin was received as gifts from Pharmacia-Upjohn-Farmitalia (Milan, Italy) and Sicor, Inc. (Milan, Italy). DNA oligonucleotides were obtained from Integrated DNA Technologies, Coralville, Iowa. and purified as described earlier; concentrations are reported as single stranded DNA (ssDNA). Formaldehyde was obtained from Mallinckrodt as a 37% by weight solution in water containing 10–15% methanol. Water was distilled and purified with a Millipore Q-UF Plus purification system to 18 Mohm-cm. Phosphate buffer, pH 7.3, was 77.4 mM Na$_2$HPO$_4$ and 22.6 mM NaH$_2$PO$_4$; phosphate buffer, pH 6.0 was 12 mM Na$_2$HPO$_4$ and 88 mM NaH$_2$PO4. Triethylamine for preparation of triethylammonium acetate buffer was 99+% from Aldrich. Deuterium oxide ("100%") was obtained from Cambridge Isotope Laboratories; DMSO-d$_6$ was also obtained from Cambridge Isotope Laboratories and stored over 3 Å molecular sieves. HPLC analyses were performed with a Hewlett-Packard 1090 liquid chromatograph equipped with a diode array UV-vis detector and workstation; chromatographies were performed with a Hewlett-Packard 5-μm C18 microbore column, 2.1 mm i.d. ×100 mm, eluting at 0.5 mL/min with gradients of triethyl ammonium acetate (Et$_3$NHOAc) (20 mM)/acetic acid (AcOH) buffer and acetonitrile and detecting at 260 and 480 nm. The methods employed were Method I: A=CH$_3$CN, B=pH 7.4 buffer, A:B, 0:100 to 70:30 at 10 min, isocratic until 12 min, 0:100 at. 15 min and Method II: A=CH$_3$CN, B=pH 6 buffer, A:B, 0:100 to 7:93 at 1 min, to 9:91 at 10 min, to 70:30 at 13 min, isocratic until 15 min, and to 0:100 at 17 min.

Example 15
The Dimeric Formaldehyde Conjugate of Epidoxorubicin.

A pH 6 triethyl ammonium acetate solution containing 13.1 μmol of epidoxorubicin-HCl and 6.6 mmol of f6formaldehyde was allowed to react in the dark at 25° C. for 30 min. The mixture was then extracted with chloroform with vigorous stirring for 20 min. The chloroform solution was dried over sodium sulfate and the chloroform removed by rotary evaporation. The resulting dry solid was redissolved in 1.0 mL of chloroform. To this was added 10 mL of n-hexane. After 2 days, a large amount of precipitate had formed, which was washed with 3×5 mL of n-hexane, followed by 4×1 mL of water. The material was then placed-under vacuum (0.01 Torr) for 6 h to remove residual water to yield 3.83 μmol (59%) of the dimeric formaldehyde conjugate of epidoxorubicin. Anal. as the dihydrate ($C_{57}H_{58}N_2O_{22}\cdot2H_2O$) C, H, N. The dimeric formaldehyde conjugate of epidoxorubicin was characterized from $^1H$ NMR data and positive ion electrospray mass spectrometry. The sample for mass spectrometry was prepared by dissolving the dimeric formaldehyde conjugate of epidoxorubicin in chloroform and diluting an aliquot of the chloroform solution with 200 parts of methanol v/v. The solution gave the following mass spectral peaks at m/z (assignment, relative intensity) 1219.5 (M+1+3MeOH, 15), 1:155.3 (M+1+MeOH, 27), 1143.4 (M+1−1C+MeOH, 23), 1123.3 (M+1, 30), 1111.3 (M+1−1C, 33), 1099.3 (M+1−2C, 20), 1086.5 (M+1−3C, 12), 698.3 (27), 654.2 (35), 600.3 (epidoxorubicin+1+2C+MeOH, 70), 588.3 (epidoxorubicin+1+1C+MeOH, 55), 572.3 (55), 556.3 (epidoxorubicin+1+1C, 100), 544.3 (epidoxorubicin+1, 73). The dimeric formaldehyde conjugate of epidoxorubicin was stable in dry DMSO-$d_6$ for at least 4 days, as determined by $^1H$ NMR analysis.

Example 16
Stability of the Dimeric Formaldehyde Conjugate of Epidoxorubicin in Aqueous Media.

A 960 μL solution of pH 7.3 phosphate buffer was heated to 37° C. The dimeric formaldehyde conjugate of epidoxorubicin was then introduced (40 μL in DMSO) such that the final concentration was 25 μM in 96% buffer/4% DMSO. The degradation of the dimeric formaldehyde conjugate of epidoxorubicin to epidoxorubicin was monitored by HPLC using Method I. The triethylammonium acetate/acetic acid (TEAA) buffer was adjusted to pH 7.4 to eliminate sample degradation on the column during analysis. No change in the chromatography was observed if pH, 7.3 phosphate buffer was used as the eluent in place of pH 7.4 TEAA buffer. The retention times for epidoxorubicin and the dimeric formaldehyde conjugate of epidoxorubicin were 7.4 and 11.1 min, respectively. The above procedure was also carried out with 10 μM the dimeric formaldehyde conjugate of epidoxorubicin. Additional experiments were run in pH 6.0 phosphate buffer (25° C. and 37° C.), pH 7.4 RPMI Media 1640 containing 10% fetal bovine serum (37° C.), and pH 8.1 fetal bovine serum (37° C.), all with 25 μM the dimeric formaldehyde conjugate of epidoxorubicin.

Hydrolysis of the dimeric formaldehyde conjugate of epidoxorubicin was also observed by $^1H$ NMR spectroscopy. A sample containing 3.6 mM the dimeric formaldehyde conjugate of epidoxorubicin in 93% DMSO-$d_6$/7% $D_2O$ (v/v) was prepared. It showed 32% intermediate B in equilibrium with the dimeric formaldehyde conjugate of epidoxoribicin within 5 min based upon integration of characteristic resonances. The sample was maintained at ambient temperature for 2 h; after this period no change in the spectrum was observed. The amount of $D_2O$ was then increased to 10% (v/v) and the amount of intermediate B increased to 45%; this solution showed no additional change during a subsequent 2-day period. Another sample containing 3.9 mM the dimeric formaldehyde conjugate of epidoxorubicin was prepared in DMSO-$d_6$. A stock 122 mM solution of HCl in $D_2O$ was prepared by adding concentrated hydrochloric acid to $D_2O$. The HCl solution was periodically added in 0.5 mol equiv aliquots to the DMSO-$d_6$ solution of the dimeric formaldehyde conjugate of epidoxorubicin. Hydrolysis to epidoxorubicin and formaldehyde occurred within 5 min. upon each addition. Complete hydrolysis occurred upon addition of ca. 2–3 equiv of HCl. A similar experiment was performed using HCl in H2O. A third sample of the dimeric formaldehyde conjugate of epidoxorubicin was prepared in $D_2O$ ("100%") containing 4% DMSO-$d_6$ to a concentration of ca. 25 μM. This solution was incubated at 37° C. for 24 h prior to NMR analysis. The spectrum showed evidence for the dimeric formaldehyde conjugate of epidoxorubicin in equilibrium with intermediates B, C, and D (Scheme VI). A control spectrum of epidoxorubicin in 96% $D_2O$/4% DMSO-$d_6$ was also obtained.

Example 17
Drug-DNA Conjugate Formation with the Dimeric Formaldehyde Conjugate of Epidoxorubicin.

A mixture containing 33 μM $(GC)_4$ and 33 μM the dimeric formaldehyde conjugate of epidoxorubicin in pH 7.3 phosphate buffer containing 4% DMSO to facilitate the dimeric formaldehyde conjugate of epidoxorubicin solubilization was prepared. The amount of available formaldehyde was 99 μM (3×33 μM). The formation of drug-DNA conjugates at 25° C. was monitored by HPLC (Method II)., After 24 h, 68% of the DNA had reacted to form a mixture of 5drug-DNA conjugates. The ratio of the conjugates, based upon HPLC peak areas, was 7:20:12:11:18, respectively. The experiment was also run at 25° C. in pH 6.0 phosphate buffer containing 4% DMSO. After 5 h, 64% of the DNA reacted to form drug-DNA conjugates. The ratio of drug-DNA conjugates 1–5 was 8:18:5:10:23, respectively. For all the dimeric formaldehyde conjugate of epidoxorubicin and epidoxorubicin-$(GC)_4$ reactions, the $A_{260}A_{480}$ ratios for the drug-DNA conjugates 2–5 were ca. 24:1, 15:1, 12:1, and 13:1, respectively. The ratio for conjugate 1 was assumed to be 24:1, based upon the value for conjugate 2. Conjugate 1 was often poorly resolved as a shoulder on the DNA peak. Under these circumstances, the conjugate 1 area was estimated based upon its 480 nm absorbance, assuming the 24:1 ratio for $A_{260}:A_{480}$. For each of the drug-DNA conjugates, 1–5, $A_{510}>A_{480}$, The retention times for the HPLC peaks were 6.4 min (DNA), 6.7 min (conjugate 1), 7.9 min (conjugate 2), 9.1 min (conjugate 3), 11.0 min (conjugate 4), and 12.1 min (conjugate 5). Conjugate 4 contained a shoulder which was included as part of the conjugate 4 peak area.

Example 18
Large-Scale Reaction of the Dimeric Formaldehyde Conjugate of Epidoxorubicin with $(GC)_4$ for Electrospray Mass Spectral (ESMS) Analysis.

A reaction mixture containing 398 μM $(GC)_4$ and 796 μM of the dimeric formaldehyde conjugate of epidoxorubicin in pH 7.3 phosphate buffer was allowed to react in the dark at 25° C. for 5 h. At this time, the DNA had formed 91% drug-DNA conjugates, according to HPLC analysis (Method II). The ratios of the drug-DNA conjugates were 1:5:10:22:53 for conjugates 1–5, respectively. Some of the dimeric formaldehyde conjugate of epidoxorubicin precipitated out of solution, as it was present in high concentration. The drug-DNA conjugates were isolated by HPLC as described previously for DNA-daunomycin and -doxorubicin conjugates and analyzed by ESMS.

Example 19
Drug-DNA Conjugate Formation with Epidoxorubicin and Formaldehyde.

A reaction mixture containing 33 μM $(GC)_4$, 66 μM epidoxorubicin, and 99 μM formaldehyde in pH 7.3 phosphate buffer containing 4% DMSO was prepared. The formation of drug-DNA conjugates at 25° C. was monitored by HPLC (Method II). After 5 h, 75% of the DNA had reacted to form drug-DNA conjugates. The ratios of drug-DNA conjugates 1–5 were 11:24:8:8:26, respectively. The experiment was also run in pH 6.0 phosphate buffer containing 4% DMSO. After 5 h, 51% of the DNA reacted to form drug-DNA conjugates. The ratios for conjugates 1–5 were 11:16:4:7:13.

Example 20
Large-Scale Reaction of Epidoxorubicin and Formaldehyde with $(GC)_4$ for ESMS Analysis.

A reaction mixture containing 166 $\mu$M $(GC)_4$, 664 $\mu$M epidoxorubicin, and 996 $\mu$M HCHO in pH 7.3 phosphate buffer (4% DMSO) was allowed to react in the dark at 25° C. for 5 h. At this time 93% of the DNA had reacted to form drug-DNA conjugates. The conjugate ratios were 1:6:5:31:49 for conjugates 1–5, respectively. The conjugates were isolated by HPLC as described previously for DNA-daunomycin and -doxorubicin conjugates and analyzed by ESMS.

Example 21
Cell Experiments.

MCF-7 breast cancer cells were obtained from American Type Culture Collection (Rockville, Md.). MCF-7/ADR adriamycin resistant breast cancer cells were a gift of Dr. William W. Wells (Michigan State University). Both cell lines were maintained in vitro by serial culture in phenol red-free RPMI Media 1640 supplemented with 10% fetal bovine serum (Gemini Bio-Products, Calbasas, Calif.), L-glutamine (2 mM), HEPES buffer (25 mM), penicillin (100 units/mL), and streptomycin (100 $\mu$g/mL). The MCF-7/ADR cell line media was additionally supplemented with 5 FM doxorubicin (Nexstar Pharmaceuticals, San Dimas, Calif.). Cells were maintained at 37° C. in a humidified atmosphere of 5% $CO_2$ and 95% air. Determination of the cytotoxicity of epidoxorubicin and the dimeric formaldehyde conjugate of epidoxorubicin was accomplished using the procedure described earlier. The results are reported in Table 2.

Control experiments established that the $IC_{50}$ value for formaldehyde was in excess of 200 $\mu$M with MCF-7 and MCF-7/ADR cells. Additional control experiments established that 3 h incubation of cells with 1% DMSO in growth media did not alter the survival of MCF-7 or MCF-7/ADR cells.

Example 22
Toxicity of Hydrolyzed Dimeric Formaldehyde Conjugate of Epidoxorubicin.

The following stock solutions of the dimeric formaldehyde conjugate of epidoxorubicin in DMSO were prepared: 1 $\mu$M, 500 $\mu$M, 100 $\mu$M, 50 $\mu M_{10}$ $\mu$M, 5 $\mu$M, 1 $\mu$M, and 100 $\mu$M. These were then diluted 10× with autoclaved Millipore water. The resulting solutions in 90% water/10% DMSO (v/v) were incubated at 37° C. for 20 h. A 20 $\mu$L aliquot of each solution containing hydrolyzed the dimeric formaldehyde conjugate of epidoxorubicin was then added to each of the appropriate wells of a 96-well plate each containing 1000 cells in 180 $\mu$L of RPMI 1640 media. At this point the experiment was conducted as previously described for $IC_{50}$ measurements with the dimeric formaldehyde conjugate of doxorubicin and the dimeric formaldehyde conjugate of daunorubicin. As an additional control, the $IC_{50}$ value for the dimeric formaldehyde conjugate of epidoxorubicin, stored for 20 h in DMSO at ambient temperature, was simultaneously determined. The results are reported in Table 2.

Example 23
Toxicity of the Dimeric Formaldehyde Conjugate of Epidoxorubicin and Epidoxorubicin after 6 hours Incubation in RPMI 1640 Media.

Stock solutions (1 mM) of epidoxorubicin and the dimeric formaldehyde conjugate of epidoxorubicin were prepared in DMSO and diluted 10× in RPMI. 1640 media containing 10% fetal bovine serum. The resulting 90% media/10% DMSO solutions (v/v) were incubated at 37° C. for 6h. The 100 $\mu$M solutions were then diluted to concentrations of 50 $\mu$M, 10 $\mu$M, 5 $\mu$M, 1 $\mu$M, 500 nM, 100 nM and 10 nM in RPMI 1640 media, each time supplementing the solutions with the proper volume of DMSO such that each solution composition remained 90% media/10% DMSO. A 20 $\mu$L aliquot of the resulting 8 solutions was then added to the appropriate wells of a 96-well plate containing 1000 cells in 18.0. $\mu$L of RPMI 1640-media. At this point the experiment was conducted as previously described for $IC_{50}$ measurements with the dimeric formaldehyde conjugate of doxorubicin and the dimeric formaldehyde conjugate of daunorubicin. The results are reported in Table 3.

Example 24
Prostate Cancer Cell Experiments: DU-145, PC-3, LNCaP.

Cell lines were maintained in vitro in RPMI 1640 media or DMEM, each supplemented with 10% fetal bovine serum, 2 mM L-glutamine, 10 mM HEPES buffer, penicillin (100 units/mL) and streptomycin (100 $\mu$g/mL).

Cells were dissociated with trypsin/EDTA, counted, and suspended in growth media (RPMI or DMEM) to a concentration of 5.6×103 cells/mL. Cell suspensions were dispensed in 180 $\mu$L aliquots into 96-well tissue culture plates. The plates were then incubated 24 h at 37° C. in a humidified atmosphere of 5% $CO_2$ and 95% air, Cytotoxic agents (doxorubicin (DOX), the dimeric formaldehyde conjugate of doxorubicin (DOXF), daunorubicin (DAU), the dimeric formaldehyde conjugate of daunorubicin (DAUF), epidoxorubicin (EPI), the dimeric formaldehyde conjugate of epidoxorubicin (EPIF)) were dissolved in DMSO to a concentration of 1 mM; sonicated to facilitate solvation, and serially diluted in DMSO to provide eight 100× DMSO drug solutions. Each 100× solution was diluted 10× in growth media (RPMI or DMEM), and a 20 $\mu$L aliquot of the resulting 10× solution was immediately (<10s) added to-the appropriate lane. Additionally, one lane was treated with 20 $\mu$L of 10% DMSO in growth media (no drug) and one lane was treated with 200 $\mu$L of 1.5 M Tris buffer (no cells). The cells were incubated with the drugs for 3 h at 37° C. The drug solutions were then removed and replaced with 200 $\mu$L of fresh media. The cells were incubated for 4 days (7 days for PC-3 cells in DMEM) at 37° C. in a humidified atmosphere of 5% $CO_2$ and 95% air. Cell survival was determined using a crystal violet assay as described earlier (Fenick, D. J. et al (1997) J. Med. Chem. 40: 2452–2461). The results are reported in Table 4.

Example 25
Uptake Experiments.

All tissue culture materials were obtained from Gibco Life Technologies (Grand Island, N.Y.) unless otherwise stated. MCF-7 breast cancer cells were obtained from American Type Culture Collection (Rockville, Md.). MCF-7/ADR and MCF-7 cell lines were maintained in vitro by serial culture in RPMI Media 1640 supplemented with 10% fetal bovine serum (Gemini Bio-Products, Calbasas, Calif.), L-glutamine (2 mM), HEPES buffer (10 mM), penicillin (100 units/mL), and streptomycin (100 mg/mL). Cells were maintained at 37° C. in a humidified atmosphere of 5% $CO_2$ and 95% air.

Measurement of drug uptake was performed by flow cytometry. Cultured cells were dissociated with trypsin-EDTA, counted, and suspended in growth media to a concentration of 1×10⁵ cells/mL. Cell suspensions were dispensed in 10 mL aliquots into 100 mm petri dishes. The petri dishes were then incubated for 24 h at 37° C. in a humidified atmosphere of 5% CO2 and 95% air. The petri dishes were determined to contain 1.5×10⁶–2.5×10⁶ cells immediately prior to drug treatment.

Cytotoxic agents (DAU, DOX, DAUF, DOXF, EPI, EPIF) were dissolved in DMSO at a concentration of 1 milli equiv/L and sonicated to facilitate solvation. Concentrations were confirmed by measuring the solution absorbance at 480 nm ($\epsilon$=11,500/mol anthracycline). The drug solution was then diluted in RPMI 1640 (–) phenol red to give a 1 micro equiv/L solution. Immediately following this dilution, the growth media of 7petri dishes was replaced with 10 mL of the 1 micro equiv/L drug solution. The petri dishes were incubated at 37° C. for various amounts of time (7.5, 15, 30, 45, 60, 90, and 120 min). For each time point, the drug solutions were removed from the petri dish and the cells dissociated with trypsin-EDTA. The resulting cell suspension was centrifuged (5 min, 800 RPM) and resuspended in 1 mL of RPMI (–) phenol red. The cell suspension was held at 4° C. until analysis (up to 2h). Control experiments indicated no appreciable loss of fluorescence in samples held at 4° C. for the time course of the experiment.

The extent of drug uptake was determined by flow cytometry as previously described (Durand & Olive, 1981). All flow cytometry measurements were made with a Becton Dickinson FACScan flow cytometer, using a Hewlett-Packard 9000 Series Model 340 computer for data storage and analysis. Drug-treated cells were analyzed with excitation at 488 nm (15 mW Ar-ion laser), with emission monitored between 570–600 nm. Instrument settings were held constant for all experiments. The emission of drug-free cells was similarly measured to determine background fluorescence. The progressive increase in fluorescence with increasing incubation time is indicated by the movement of the mean value of the histogram to progressively higher channel numbers. The final data are plotted as mean channel number (as determined by computer data analysis) vs. drug incubation time for ease of data representation and appear in FIGS. 4A and B.

Measurement of intracellular drug distribution was performed by laser confocal microscopy. Cultured cells were dissociated With trypsin-EDTA, counted, and suspended in growth media to a concentration of 1×10⁴ cells/mL. Cell suspensions were dispensed in 2 mL aliquots into two-well chambered coverslips (Nunc) to allow observation of living cells with an inverted microscope. The coverslips were then incubated for 24 h at 37° C. in a humidified atmosphere of 5% $CO_2$ and 95% air.

Cytotoxic agents (DAU, DOX, DAUF, DOXF, EPI, EPIF) were dissolved in DMSO at a concentration of 1 milli equiv/L and sonicated to facilitate solvation. Concentrations were confirmed by measuring the solution absorbance at 480 nm ($\epsilon$=11,500/mole anthracycline). The drug solution was then diluted in RPMI 1640 (–) phenol red to the final desired drug concentration. Immediately following this dilution, the growth media of the chambered coverslip was replaced with 2 mL of the drug solution. The coverslips were incubated at 37° C. for various amounts of time. At the end of the. incubation, the media was replaced with 2 mL of RPMI 1640 (–) phenol red. In some experiments, the coverslips were again allowed to incubate at 37° C. for various amounts of time prior to observation.

Intracellular drug distribution was observed using a Molecular Dynamics Multiprobe 2001 confocal laser scanning microscope fitted with a Nikon inverted microscope. All data acquisitions were recorded through a 60X oil immersion objective lens. Data acquisitions were performed using a Silicon Graphics IRIS Indigo workstation with ImageSpace software (Molecular Dynamics). Excitation and emission wavelengths for all experiments were 488 nm and 535 nm, respectively The recorded acquisitions were converted to TIFF format and processed using Adobe Photoshop LE (Adobe Systems) on a 7100/66 Power Macintosh. The results are summarized in Table 5.

Example 26

Liposomal Stabilization of the Dimeric Formaldehyde Conjugate of Daunorubicin.

The liposomes used in this study were obtained from NeXstar Pharmaceuticals (Boulder, Colo.) and consisted of 2:1 (mol:mol) distearoylphosphatidylcholine (DSPC) :cholesterol. They had a diameter of 0.054 $\mu$m. The liposomes were in a solution of 9% sucrose, 25 mM sodium phosphate, pH 7.4. The solution contained 50 mg. liposome/mL. Each liposome contained approximately 50,000 lipids (DSPC and cholesterol), and each milliliter of solution contained ca. 8.91×10⁴liposomes.

Daunorubicin (1.48 $\mu$mol) and formaldehyde (148 $\mu$mol) were mixed in pH 7.4 sodium phosphate buffer (25 mM) at 25° C. The total volume was 150 $\mu$L. This solution was then added to 1 mL of liposomes and incubated at 65° C. for 45 min. This facilitated the dimeric formaldehyde conjugate of daunorubicin (generated in situ) incorporation into the liposome. The liposomes were allowed to cool to 25° C. for 15 min. They were then eluted on an NAP-25 column (Sephadex G-25, Pharmacia Biotech) using pH 7.4 sodium phosphate buffer (25 mM) as the eluent. The first liposomes containing the dimeric formaldehyde conjugate of daunorubicin eluted off the column after ca. 5 min. After the liposomes were collected the elution was continued and the free daunorubicin was collected. UV-vis analysis of the free daunorubicin solution indicated that 81% of the daunorubicin was incorporated into the liposomes. The liposomes were analyzed by HPLC to determine the stability of the dimeric formaldehyde conjugate of daunorubicin in the liposome at 25° C. The above procedure: was repeated using the same buffer supplemented with 9% sucrose as the eluent. The results from that experiment show similar stability. In addition, the above procedure was repeated using serum (fetal bovine serum, pH 8.1) as the column eluent. The column was equilibrated with serum prior to elution of the liposomal dimeric formaldehyde conjugate of daunorubicin. Upon elution from the column, the liposomes were collected in preheated (37° C.) Eppendorf tubes and maintained at 37° C. HPLC analysis of the liposomes at different time points showed corresponding stability for liposomal the dimeric formaldehyde conjugate of daunorubicinin serum at 37° C. considering the higher temperature.

A sample of the liposomal dimeric formaldehyde conjugate of daunorubicin eluted with 25 mM sodium phosphate/9% sucrose was stable for at least 3 months upon collection at –78° C. (dry ice/isopropyl alcohol), lyophilization, and storage at –20° C.

Liposomes were analyzed by reverse phase HPLC with a Hewlett-Packard 1090 LC equipped with a diode array UV-vis detector and workstation. Chromatographies were performed with a Hewlett-Packard 5 $\mu$m C18 microbore column, 2.1 mm i.d. ×10 cm, eluting at 0.5 mL/min using the following gradient (A: HPLC grade acetonitrile and B: pH 6.0 triethylammonium acetate buffer (20 mM)): A:B, 0:100 to 7,0:30 at 10 min, isocratic until 12 min, 70:30 to 0:100 at 15 min. The dimeric formaldehyde conjugate of daunorubicin was shown to degrade 43% on the column (to daunorubicin), based upon five injections of the dimeric formaldehyde conjugate of daunorubicin (100% pure in DMSO) and 2 injections of liposomal dimeric formaldehyde conjugate of daunorubicin. HPLC retention times for the dimeric formaldehyde conjugate of daunorubicin and dauorubicin were 8.2 and 7.4 min, respectively.

We claim:

1. A dimeric drug aldehyde conjugate compound which is an anti-cancer drug, or a pharmaceutically acceptable salt thereof, of the formula:

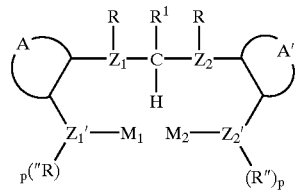

wherein $Z_1$, $Z_2$, are N;

$Z_1'$ and $Z_2'$ are the same or different heteroatoms, selected from the group consisting of N or O;

each R and R″ is, independent of each other R and R″, selected from the group consisting of —H, —OH, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

each p is 0 or 1 depending on the identity of $Z_1'$ and $Z_2'$;

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

$M_1$ and $M_2$ are each a methylene, either or both of which can be substituted with, independently of one another, one or more members of the group selected from: lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

each of $M_1$ and $M_2$ being bonded to one of $Z_1$ or $Z_2$;

and wherein A and A' independently of one another, but in combination with the 1,2-diheteroatom substituents and two carbons to which the substituents are attached, have the structure of an anthracycline.

2. A compound of claim 1 wherein $M_1$ is bonded to $Z_1$ and $M_2$ is bonded to $Z_2$.

3. A compound of claim 1 wherein $Z_1$ and $Z_2$ are N, and $Z_1'$ and $Z_2'$ are O.

4. A dimeric drug aldehyde conjugate compound which is an anti-cancer drug, or a pharmaceutically acceptable salt thereof, of the formula:

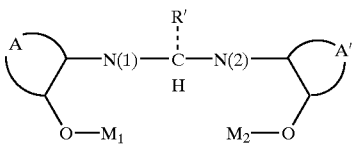

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

$M_1$ and $M_2$ are each a methylene, either or both of which can be substituted, independently of one another, with one or more members of the group selected from: lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

each of $M_1$ and $M_2$ is bonded to one of N(1) or N(2); and wherein A and A' independently of one another, but in combination with the 1,2-diheteroatom substituents and two carbons to which the substituents are attached, have the structure of an anthracycline.

5. The compound of claim 4 wherein $M_1$ is bonded to N(1) and $M_2$ is bonded to N(2).

6. The compound of claim 4 wherein $M_1$ is bonded to N(2) and $M_2$ is bonded to N(1).

7. A dimeric drug aldehyde conjugate compound which is an anti-cancer drug, or a pharmaceutically acceptable salt thereof, of the formula:

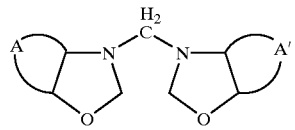

wherein A and A' independently of one another, but in combination with the 1,2-diheteroatom substituents and the two carbons to which the substituents are attached, have the structure of an anthracycline.

8. A compound of claim 2 of the formula:

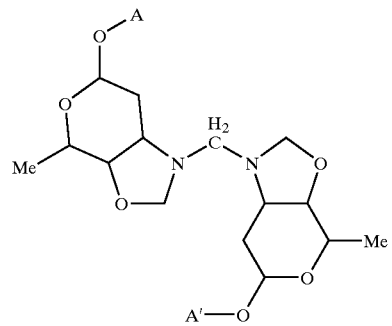

wherein A and A' have the structure of an anthracycline aglycon.

9. The compound of claim 8 wherein A and A' are anthracycline 7-deoxyaglycon-7-yls.

10. The compound of claim 8 wherein A and A' are both 7-deoxydaunorubicinon-7-yl.

11. The compound of claim 8 wherein A and A' are both 7-deoxydoxorubicinon-7-yl.

12. The compound of claim 8 wherein A is 7-deoxydaunorubicinon-7-yl and A' is 7-deoxydoxorubicinon-7-yl.

13. A compound of claim 8 wherein A=A' and A has the formula:

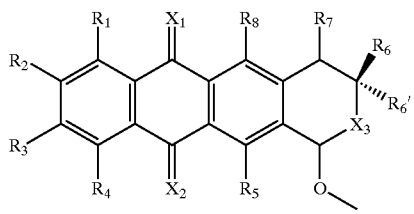

wherein:
- $X_1$ and $X_2$, independently of one another, are O; S; or substituted or unsubstituted amino;
- $X_3$ is a substituted or unsubstituted C, O, or S atom or an SO, $SO_2$ or substituted or unsubstituted amino;
- $R_1$, $R_2$, $R_3$, $R_4$, $R_5$ and $R_8$, independently of one another, are H, —OH, —SH, —O-alkyl, —O-acyl, $C_{1-20}$ alkyl, $C_{1-20}$ acyl, halogen, silyl, sulfonate, or unsubstituted or substituted amino;
- $R_6$ is H, $C_{1-20}$ alkyl or alkoxy, $C_{1-20}$ acyl or acyloxy, hydroxymethylcarbonyl, alkoxymethylcarbonyl, acyloxymethylcarbonyl, $C_{7-20}$ aryl or aryloxy, squaric acid or salts thereof, phosphonate, or a 5 or 6 membered heterocycle;
- $R_6'$ is H, halogen, $C_{1-20}$ alkyl or alkoxy, unsubstituted or substituted amino, —OH, —SH, —CN, sulfide, or a $C_{1-20}$ acyl or acyloxy; and
- $R_7$ is H, halogen, —OH, alkoxy, $C_{1-20}$ alky, —CN, amino, a $C_{1-20}$ acyl or acyloxy, or a saccharide or modified saccharide.

14. A dimeric drug aldehyde conjugate compound of claim 1 which is an anticancer drug, or a pharmaceutically acceptable salt thereof, of the formula:

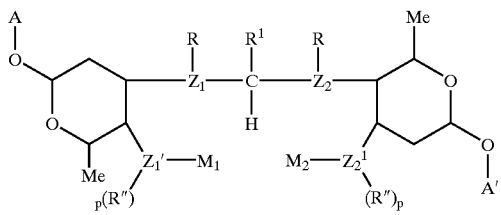

wherein $Z_1$, $Z_2$, are N;
- $Z_1'$ aid $Z_2'$ are the same or different heteroatomns, selected from the group consisting of N, or O;
- each R and R" is, independent of each other R and R", selected from the group consisting of —H, —OH, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;
- each p is 0, 1 or 2 depending on the identity of $Z_1'$ and $Z_2'$;
- R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;
- $M_1$ and $M_2$ are each a methylene, either or both of which can be substituted with, independently of one another, one or more members of the group selected from:
  lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl alkoxyalkyl, polyalkoxyalkyl, alkoxycarbonyl, carboxyalkyl, and aminocarbonyl;
- each of $M_1$ and $M_2$ being bonded to one of $Z_1$ or $Z_2$;
- and wherein A and A' are, independently of one another, anthracycline 7-deoxyaglycon-7-yls.

15. A dimeric drug aldehyde conjugate compound of claim 14 which is an anti-cancer drug, or a pharmaceutically acceptable salt thereof, of the formula:

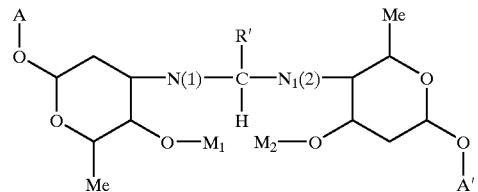

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

$M_1$ and $M_2$ are each a methylene, either or both of which can be substituted, independently of one another, with one or more members of the group selected from: lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

each of $M_1$ and $M_2$ is bonded to one of N(1) or N(2); and wherein A and A' are, independently of one another, anthracycline 7-deoxyaglycon-7-yls.

16. A pharmaceutical composition which comprises a therapeutically effective amount of the compound of claim 1 and a pharmaceutically acceptable carrier.

17. The composition of claim 16 wherein said pharmaceutically acceptable carrier is a liposome.

18. A method of treating cancer in a mammal comprising administering a compound of claim 1 in a therapeutically effective amount.

19. A method of treating cancer in a mammal comprising administering a compound of claim 4 in a therapeutically effective amount.

20. A method for making a compound of claim 1 by reacting a 1,2-dihetero-substituted anti-cancer drug with formaldehyde.

21. A method of treating cancer in a mammal comprising administering in a liposome a therapeutically effective amount of a compound of claim 1.

22. A compound of claim 1 wherein $M_1$ is bonded to $Z_2$ and $M_2$ is bonded to $Z_1$.

23. A compound of claim 1 wherein $M_1$ is bonded to $Z_2$ and $M_2$ is bonded to bonded to $Z_1$ and which has the formula:

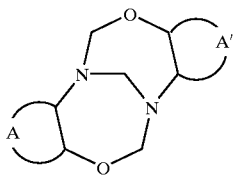

wherein A and A', independently of each other, but in combination with the 1,2-diheteroatom substituents and two carbons to which the substituents are attached, have the structure of an anthracycline.

24. A compound of claim 23 having the formula:

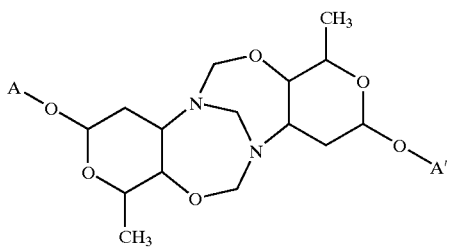

wherein A and A', independently of each other, have the structure of an anthracycline aglycon.

25. A pharmaceutical composition comprising a therapeutically effective amount of the compound of claim 23.

26. The composition of claim 25 wherein the pharmaceutically acceptable carrier is a liposome.

27. A method for treating cancer comprising administering a compound of claim 23 in a therapeutically effective amount to an individual having cancer.

28. A method for treating cancer comprising administering a compound of claim 23 in a therapeutically effective amount in a liposome to an individual having cancer.

29. The compound of claim 24 wherein A and A' are anthracycline 7-deoxyaglycon-7-yls.

30. The compound of claim 24 wherein A and A' are both 7-deoxydaunorubicinon-7-yl.

31. The compound of claim wherein A and A' are both 7-deoxydoxorubicinon-7-yl.

32. The compound of claim 24 wherein A is 7-deoxydaunorubicinon-7-yl and A' is 7-deoxydoxorubicinon-7-yl.

33. The compound of claim 24 of the formula:

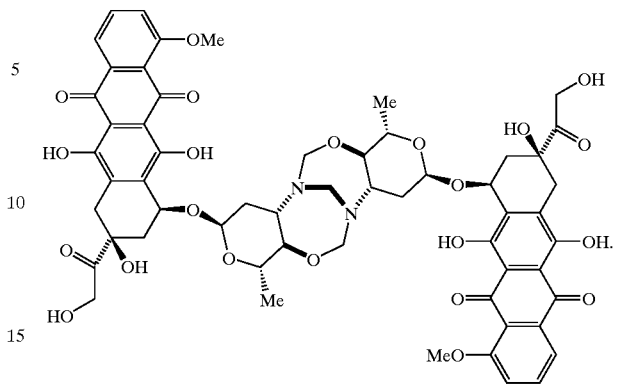

34. The compound of claim 24 of the formula:

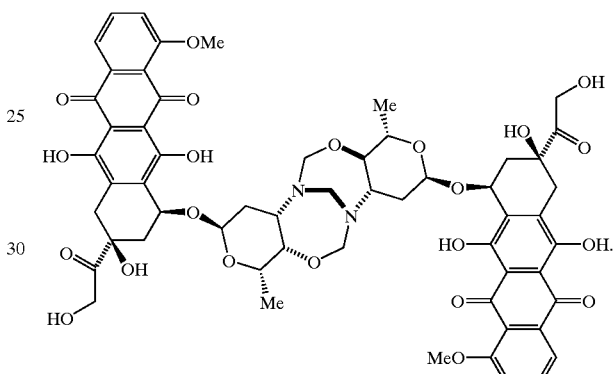

35. A compound of claim 24, having the formula:

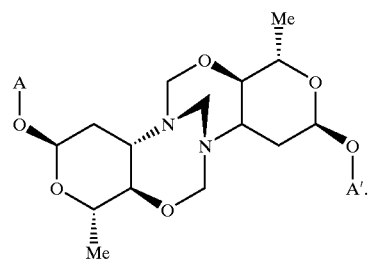

36. A compound of claim 35 wherein A=A' and A has the formula:

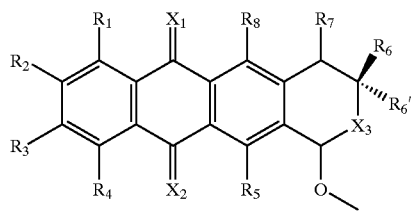

wherein:

$X_1$ and $X_2$, independently of one another, are O; S; or substituted or unsubstituted amino;

$X_3$ is a substituted or unsubstituted C, O, or S atom or an SO, $SO_2$ or substituted or unsubstituted amino;

$R_1$, $R_2$, $R_3$, $R_4$, $R_5$ and $R_8$, independently of one another, are H, —OH, —SH, —O-alkyl, —O-acyl, $C_{1-20}$ alkyl, $C_{1-20}$ acyl, halogen, silyl, sulfonate, or unsubstituted or substituted amino;

$R_6$ is H, $C_{1-20}$ alkyl or alkoxy, $C_{1-20}$ acyl or acyloxy, hydroxymethylcarbonyl, alkoxymethylcarbonyl, acyloxymethylcarbonyl, $C_{7-20}$ aryl or aryloxy, squaric acid or salts thereof, phosphonate, or a 5- or 6-membered heterocycle;

$R_6'$ is H, halogen, $C_{1-20}$ alkyl or alkoxy, unsubstituted or substituted amino, —OH, —SH, —CN, sulfide, or a $C_{1-20}$ acyl or acyloxy; and $R_7$ is H, halogen, —OH, alkoxy, $C_{1-20}$ alkyl, —CN, amino, a $C_{1-20}$ acyl or acyloxy, or a saccharide or modified saccharide.

37. The compound of claim 36 wherein:

$X_1$ and $X_2$, independently of one another, are O or NH;

$X_3$ is $CH_2$ or $CF_2$;

$R_1=R_2=R_3=H$;

$R_4$ is H, OH or methoxy;

$R_5$ is H or OH;

$R_6$ is $C_{1-20}$ acyl or acyloxy, hydroxymethyl carbonyl or alkoxymethylcarbonyl and $R_6'$ is OH.

38. The compound of claim 37 wherein:

$R_7$ is H and $R_8$ is H or OH.

39. The compound of claim 36 wherein:

$X_1$ and $X_2$ are O;

$X_3$ is $CH_2$ or $CF_2$;

$R_1=R_2=R_3=H$;

$R_4$ is H, OH or methoxy;

$R_5$ is H or OH;

$R_6$ is $C_{1-20}$ acyl or acyloxy, hydroxymethyl carbonyl or alkoxymethylcarbonyl;

$R_6'$ is OH;

$R_7$ is H; and $R_8$ is H or OH.

40. The compound of claim 39 wherein:

$R_6$ is —(CO)—$CH_3$ or —(CO)—$CH_2$—OH.

41. A pharmaceutical composition which comprises a therapeutically effective amount of a compound of claim 23 and a pharmaceutically acceptable carrier.

42. A pharmaceutical composition of claim 41 wherein the pharmaceutically acceptable carrier is a liposome.

43. A method for treating cancer comprising the step of administering a compound of claim 23 to an individual in a therapeutically effective amount.

44. A method of claim 43 wherein said compound is administered in a liposome.

45. The compound of claim 7 of the formula:

46. The compound of claim 7 of the formula:

47. The dimeric drug aldehyde conjugate compound of claim 2 which is an anti-cancer drug, or a pharmaceutically acceptable salt thereof, of the formula:

wherein $Z_1$, $Z_2$, are N;

$Z_1'$ and $Z_2'$ are the same or different heteroatoms, selected from the group consisting of N or O;

each R is, independent of other R is selected from the group consisting of: —H, —OH, lower alkyl $C_{1-6}$, lower alkenyl $C_{1-6}$, $C_{1-20}$ alkyl, $C_{1-20}$ alkenyl, aryl, hydroxylated alkyl, hydroxylated alkenyl, halogenated alkyl, halogenated alkenyl, silyl, sulfonatoalkyl, alkylaryl, aralkyl, alkoxyalkyl, polyalkoxyalkyl, and carboxyalkyl;

wherein when $Z_1'$ and $Z_2'$ are O, p is 0;

wherein when $Z_1'$ and $Z_2'$ are N, each R" is, independent of other R" is selected from the group consisting of: —H, —OH, lower alkyl $C_{1-6}$, lower alkenyl $C_{1-6}$, $C_{1-20}$ alkyl, $C_{1-20}$ alkenyl, aryl, hydroxylated alkyl, hydroxylated alkenyl, halogenated alkyl, halogenated alkenyl, silyl, sulfonatoalkyl, alkylaryl, aralkyl, alkoxyalkyl, polyalkoxyalkyl, and carboxyalkyl;

each p is 0 or 1 depending on the identity of $Z_1'$ and $Z_2'$;

R' is selected from the group consisting of —H, lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

$M_1$ and $M_2$ are each a methylene, either or both of which can be substituted with, independently of one another, one or more members of the group selected from: lower alkyl $C_{1-6}$, lower alkenyl $C_{1-6}$, $C_{1-20}$ alkyl, $C_{1-20}$ alkenyl, $C_{1-20}$ acyl, aryl, hydroxylated alkyl, hydroxylated alkenyl, halogenated alkyl, halogenated alkenyl, silyl, sulfonyl, sulfonatoalkyl, alkylaryl, aralkyl, alkoxyalkyl, polyalkoxyalkyl, alkoxycarbonyl, carboxyalkyl, and aminocarbonyl;

each of $M_1$ and $M_2$ being bonded to one of $Z_1$ or $Z_2$;

and wherein A and A' independently of one another, but in combination with the 1,2-diheteroatom substituents and two carbons to which the substituents are attached, have the structure of an anthracycline.

48. A dimeric drug aldehyde conjugate compound which is an anti-cancer drug, or a pharmaceutically acceptable salt thereof, of the formula:

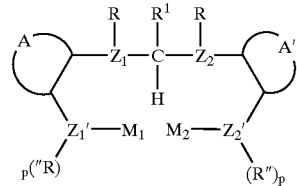

wherein $Z_1$, $Z_2$, are N;

$Z_1'$ and $Z_2'$ are O;

$R_1'$ is H;

R=H;

each p is 0;

$M_1$ and $M_2$ are each a methylene;

each of $M_1$ and $M_2$ being bonded to one of $Z_1$ or $Z_2$;

and wherein A and A' independently of one another, but in combination with the 1,2-diheteroatom substituents and two carbons to which the substituents are attached, have the structure of an anthracycline.

49. A compound which is an anti-cancer drug of the formula:

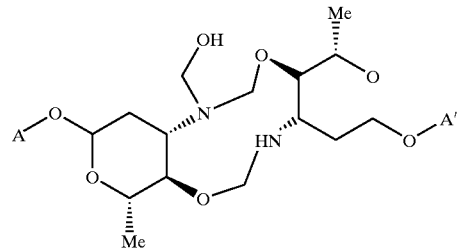

wherein each A and A', independent of each other A and A', have the structure of an anthracycline aglycon.

* * * * *